US012758578B2

(12) United States Patent
Blanzat et al.

(10) Patent No.: US 12,758,578 B2
(45) Date of Patent: Oct. 13, 2026

(54) ANTI-INFLAMMATORY DENDRIMER FORMULATION FOR THE TREATMENT OF PSORIASIS

(71) Applicants: CENTRE NATIONAL DE LA RECHERCHE SCIENTIFIQUE—CNRS, Paris (FR); UNIVERSITE PAUL SABATIER TOULOUSE III, Toulouse (FR); INSERM (INSTITUT NATIONAL DE LA SANTÉ ET DE LA RECHERCHE MÉDICALE), Paris (FR)

(72) Inventors: Muriel Blanzat, Toulouse Cedex (FR); Ranime Jebbawi, Toulouse Cedex (FR); Rémy Poupot, Toulouse Cedex (FR); Cédric-Olivier Turrin, Toulouse Cedex (FR); Michel Simon, Belberaud (FR); Emily Clement, Colomiers (FR); Hélène Labie, Toulouse (FR); Abdelouahd Oukhrib, Toulouse (FR)

(73) Assignees: CENTRE NATIONAL DE LA RECHERCHE SCIENTIFIQUE (CNRS); UNIVERSITE PAUL SABATIER TOULOUSE III, Toulouse (FR); INSERM (INSTITUT NATIONAL DE LA SANTÉ ET DE LA RECHERCHER MÉDICALE, Paris (FR)

( * ) Notice: Subject to any disclaimer, the term of this patent is extended or adjusted under 35 U.S.C. 154(b) by 1119 days.

(21) Appl. No.: 17/787,787

(22) PCT Filed: Dec. 22, 2020

(86) PCT No.: PCT/FR2020/052608
§ 371 (c)(1),
(2) Date: Jun. 21, 2022

(87) PCT Pub. No.: WO2021/130453
PCT Pub. Date: Jul. 1, 2021

(65) Prior Publication Data

US 2023/0085651 A1 Mar. 23, 2023

(30) Foreign Application Priority Data

Dec. 23, 2019 (FR) ...................................... 1915517

(51) Int. Cl.

| | |
|---|---|
| ***A61K 31/80*** | (2006.01) |
| ***A61K 31/66*** | (2006.01) |
| ***A61K 47/30*** | (2006.01) |
| ***A61P 17/06*** | (2006.01) |

(52) U.S. Cl.
CPC .............. *A61K 31/80* (2013.01); *A61K 31/66* (2013.01); *A61K 47/30* (2013.01); *A61P 17/06* (2018.01)

(58) Field of Classification Search
CPC ........ A61K 31/80; A61K 31/66; A61K 47/30; A61P 17/06
See application file for complete search history.

(56) References Cited

U.S. PATENT DOCUMENTS

2010/0173871 A1* 7/2010 Poupot .................. A61K 31/80
514/102

FOREIGN PATENT DOCUMENTS

| | | | |
|---|---|---|---|
| EP | 2341915 | A1 | 7/2011 |
| WO | 2010/013086 | A1 | 2/2010 |

OTHER PUBLICATIONS

A. Boudier, et al., "Polyvalent catanionic vesicles: Exploring the drug delivery mechanisms," International Journal of Pharmaceutics 403 (2011) 230-236. (Year: 2011).*
Rico-Lattes, et al. "Catanionic sugar derived surfactants, polymers and dendrimers: from molecules to targeted self-organized systems," C. R. Chimie 8 (2005) 807-814. (Year: 2005).*
Ielasi, et al. "Influence of PPH dendrimers' surface functions on the activation of human monocytes: a study of their interactions with pure lipid model systems," Phys. Chem. Chem. Phys., 2016, 18, 21871-21880. (Year: 2016).*
Blanzat, et al. "Dendritic Catanionic Assemblies: In vitro Anti-HIV Activity of Phosphorus-Containing Dendrimers Bearing Galb1cer Analogues," Chem BioChem 2005, 6, 2207-2213. (Year: 2005).*
Brun, A. and Etemad-Moghadam, G., "New Double-Chain and Aromatic (-Hydroxyalkyl)phosphorus Amphiphiles", Synthesis No. 10, Jul. 30, 2002.
Caminade, A. et al, "The key role of the scaffold on the efficiency of dendrimer nanodrugs", Nature Communications 6:7722, Jul. 14, 2015.
Castagnos, Pauline, "Thesis", University of Toulouse, Nov. 9, 2011.
Consola, S. et al, "Design of Original Bioactive Formulations Based on Sugar-Surfactant/Non-steroidal Anti-inflammatory Cataniononic Self-Assemblies: A New Way of Dermal Drug Delivery", Chem. Eur. J. 13, 2007.
Portevin, D. et al., "Regulatory activity of azabisphosphonate-capped dendrimers on human CD4+ T cell proliferation enhances ex-vivo expansion of NK cells from PBMCs for immunotherapy", Journal of Translational Medicine 7:82, Sep. 24, 2009.
Poupot, M. et al, "Design of phosphorylated dendritic architectures to promote human monocyte activation", The FASEB Journal 20, Nov. 2006.
Rolland, O. et al., "Tailored Control and Optimisation of the Number of Phosphonic Acid Termini on Phosphorus-Containing Dendrimers for the Ex-Vivo Activation of Human Monocytes", Chem. Eur. J. 14, 2008.

(Continued)

*Primary Examiner* — Michael P Cohen
(74) *Attorney, Agent, or Firm* — WCF IP

(57) ABSTRACT

The present invention relates to sugar-derived catanionic surfactant vesicles comprising anti-inflammatory dendrimers and to their use as a medicament, more particularly in the treatment of psoriasis.

11 Claims, 20 Drawing Sheets

(56) References Cited

OTHER PUBLICATIONS

Hayder, M. et al., “A Phosphorus-Based Dendrimer Targets Inflammation and Osteoclastogenesis in Experimental Arthritis”, Sci Transl Med 3, May 2011.
Klymchenko, A. et al, “Modulation of the solvent-dependent dual emission in 3-hydroxychromones by substituents”, New J. Chem. 27, 2003.
Hayder, M. et al, “Three-Dimensional Directionality Is a Pivotal Structural Feature for the Bioactivity of Azabisphosphate-Capped Poly(PhosphorHydrazone) Nanodrug Dendrimers”, Biomacromolecules 19, 2018.
Fruchon, S. et al, “Biodistribution and Biosafety of a Poly(Phosphorhydrazone) Dendrimer, an Anti-Inflammatory Drug-Candidate”, Biomolecules 9, 2019.
Hayder, M. et al, “Phosphorus-Based Dendrimer ABP Treats Neuroinflammation by Promoting IL-10-Producing CD4+ T Cells”, Biomacromolecules, 2015.
Ielasi, F. et al, “Influence of PPH dendrimers’ surface functions on the activation of human monocytes: a study of their Interactions with pure lipid model systems”, Phys. Chem. Chem. Phys. 18, 2016.
Blanzat, M. et al, “Dendritic Catanionic Assemblies: In vitro anti-HIV Activity of Phosphorus-Containing Dendrimers Bearing Gal[beta]1cer Analogues”, ChemBioChem 6, 2005.
Soussan, Langmuir 2008, 24:2326-2330.

* cited by examiner

G1-X

TRICAT-m

ANTI-INFLAMMATORY DENDRIMER FORMULATION FOR THE TREATMENT OF PSORIASIS

TECHNICAL FIELD

The present invention relates to sugar-derived catanionic surfactant vesicles comprising anti-inflammatory dendrimers and to their use as a medicament, more particularly in the treatment of psoriasis.

PRIOR ART

Psoriasis is a chronic inflammatory skin disease that is the result of accelerated renewal of the epidermis sustained by inflammation and which manifests itself by the appearance of red patches covered with white flakes which are shed from the skin (scales). This disease affects more than 125 million people worldwide and has a major impact on the quality of life of those affected. Today, there is no treatment for psoriasis and the causes of this disease are manifold and still poorly understood.

However, treatments which make it possible to alleviate symptoms have been developed, such as topical application of corticosteroids or vitamin D. These treatments make it possible to relieve the mild symptoms of psoriasis but are only marginally effective in treating the most severe forms. The most severe forms are treated with oral administration of immunosuppressants such as cyclosporine, but the latter have significant side effects. Monoclonal antibodies and soluble receptors targeting pro-inflammatory mediators such as TNF, IL-12, IL-23 and IL-17 have been proposed. These biologic medicaments are expensive and their effectiveness decreases over time. They are also contraindicated in certain co-morbidities associated with psoriasis.

Therefore, there remains a need to develop new treatments for the treatment of psoriasis for topical application, thus limiting side effects.

Dendrimers are macromolecules consisting of monomers combined together to form a three-dimensional multi-branched architecture with a defined structure. Dendrimers have a perfectly defined size and structure thanks to their iterative synthesis. Their multivalence makes them very attractive nano-objects for many applications, especially in biology and medicine.

In particular, Azabisphosphonate surface phosphorus dendrimers (ABP dendrimer) are able to activate monocytes and induce an anti-inflammatory response (WO2010/013086, Portevin D. et al. J Transi Med. 2009; 7:82). More particularly, the anti-inflammatory properties have been validated in animal models of rheumatoid arthritis wherein monocytes are known to play a primary role in inflammation and osteoclastogenesis (Hayder M. et al. 2011; Sci Trans Med. 3(81)). The anti-inflammatory effect of ABP dendrimer has also been validated in uveitis models (Fruchon et al. 2013. Molecules; 18(8):9305-16) and multiple sclerosis (Hayder M. Biomacromolecules 2015; 16, 3425-3433). In contrast, the potential effect of these dendrimers in the treatment of psoriasis has only been suggested in the international application WO2010/013086.

SUMMARY

The treatment of a dermatosis linked to an hyperproliferation of keratinocytes and/or to an inflammatory context, such as psoriasis, by cutaneous route requires the crossing of the stratum corneum which ensures the barrier function of the skin, which makes its crossing by active principles very complex. Thus, to treat psoriasis by the cutaneous route, it is necessary to improve the penetration of the active substances into the skin.

To allow better skin penetration of the dendrimers, the inventors have formulated the aza-bisphosphonate dendrimers with sugar-derived catanionic surfactants. Sugar-derived catanionic surfactants spontaneously associate in the form of vesicles and can encapsulate hydrophobic active ingredients in their membrane bilayer.

While hydrophilicABP dendrimers show a low encapsulation rate with sugar-derived surfactants and a transition temperature of the "solid-fluid" phase of the membrane bilayer of 37° C., the inventors have surprisingly discovered that the complex formed following the combination of the phosphonic acid form of the ABP dendrimer (ABP-OH) with a sugar-derived surfactant leads to a decrease in the transition temperature of the complex to 33° C. Thus, on contact with the skin, this complex becomes fluid and is therefore able to diffuse more easily into the deep layers of the skin, thus improving its anti-inflammatory action. In addition, the encapsulation rate of these phosphonic acid forms is higher than that of hydrophilic ABP dendrimers and the complexes are stable at a pH near that of the skin.

In a first aspect, the invention relates to a vesicle comprising:

- a catanionic surfactant of formula (I) or a mixture of catanionic surfactants of general formula (I):

[Chem. 1]

(I)

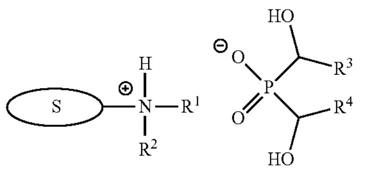

wherein

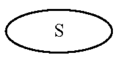

is a sugar,

- $R^1$ is selected from H and a linear or branched, saturated or unsaturated hydrocarbon chain of 1 to 20 links,
- $R^2$ is a linear or branched, saturated or unsaturated hydrocarbon chain of 1 to 20 links,
- $R^3$ and $R^4$ are independently of each other a linear or branched, saturated or unsaturated hydrocarbon chain of 1 to 19 links; and a dendrimer of formula (II):

[Chem. 2]

(II)

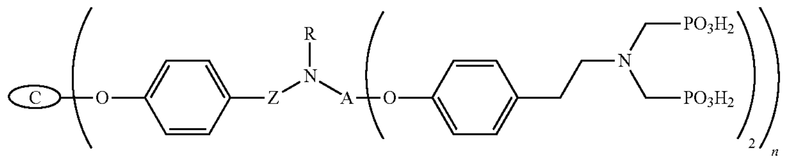

wherein

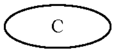

is selected from the pentoses, hexoses and the groups of following formulas:

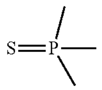

,

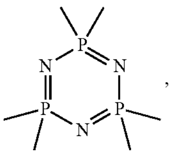

,

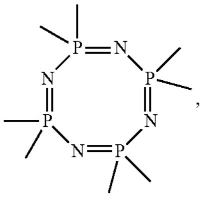

, and

Z is selected from —$CH_2$— and —CH═N—,

R is selected from H and C1-C12-alkyl,

A is selected from

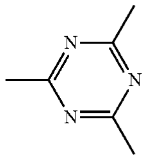

and

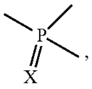

, and 2 where X is selected from S and O, and n is an integer between 3 and 8.

According to another aspect, the invention relates to a pharmaceutical composition comprising at least one vesicle according to the invention and a pharmaceutically acceptable excipient.

According to another aspect, the invention relates to a vesicle according to the invention or a pharmaceutical composition according to the invention for its use in the treatment of psoriasis.

Finally, the invention relates to a method for preparing a vesicle according to the invention.

BRIEF DESCRIPTION OF THE DRAWINGS

[FIG. 1] represents a diagram illustrating the obtaining of the bioactive formulation.

[FIG. 2] shows the phase transition temperature for the TriCat 12/ABP formulation.

[FIG. 3] shows the fluorescence quantification of the amount of ABP-NIR dendrimer (ABP dendrimer in its fluorescent form) formulated or not with TriCat 12, which penetrated into the pig ear skin (Franz cells) after 24 h at 40° C.

[FIG. 4] shows in a) the size distribution measured by DLS of the vesicles formed by the TriCat 12/G1-A (1/0.5) formulation, b) the scanning electron microscopy picture of the vesicles formed by the TriCat 12/G1-A (1/0.5) formulation.

[FIG. 5] shows the phase transition temperature for the TriCat 12/G1-A formulation.

[FIG. 6] shows the measurement of the mean hydrodynamic diameter and of the DLS intensity of the TriCat 12/G1-A formulation over two months at 4° C.

[FIG. 7] shows the measurement of the mean hydrodynamic diameter and of the DLS intensity of the TriCat 12/G1-A formulation over two months at +4° C. and −20° C.

[FIG. 8] shows the fluorescence quantification of the amount of G1A-NIR dendrimer (G1A dendrimer in its fluorescent form) formulated or not with the TriCat 12, that penetrated the pig ear skin (Franz cells) after 24 h at 35° C.

[FIG. 9] shows the confocal microscopy observation of the fluorescence (in white) of the unformulated G1-A-NIR dendrimer (left image) and formulated with the TriCat 12 (right image) that penetrated the pig ear skin (Franz cells) after 24 h at 35° C.

[FIG. 10] shows the confocal microscopy observation of the fluorescence (in white) of the unformulated G1-A-NIR dendrimer (left image) and formulated with the TriCat 12 (right image) that penetrated the human skin (Franz cells) after 24 h at 35° C.

[FIG. 11] shows the flow cytometric analysis of the morphology (size and granulosity) of monocytes (on the graphs, each point is a cell). The top graph shows the non-activated control monocytes. The bottom left graph shows monocytes cultured in the presence of TriCat 12 vesicles alone (no activation). The bottom right graph shows monocytes cultured with TriCat 12 vesicles loaded with the G1-A dendrimer. Activated monocytes are in the ellipse.

[FIG. 12] shows the therapeutic efficacy of the G1-A dendrimer and of the TriCat12 vesicles loaded with the G1-Adendrimer in the Imiquimod (IMQ) induced psoriasis mouse model. The clinical scores (top graph) are given as a function of time expressed in days. The histological scores are given on the lower graph. The "control" mice are the animals that were not treated.

[FIG. 13] shows the antiproliferative effect of compound G1-A, as a function of treatment time, on the N-TERT keratinocyte line (top graphs) and on primary human keratinocytes (bottom graphs).

[FIG. 14] shows in a) the size distribution measured by DLS of the vesicles formed by the TriCat 12/G1-B (1/0.5) formulation, b) the scanning electron microscopy picture of the vesicles formed by the TriCat 12/G1-B (1/0.5) formulation.

[FIG. 15] shows the phase transition temperature of the TriCat 12/G1-B formulation.

[FIG. 16] shows the measurement of the mean hydrodynamic diameter and of the DLS intensity of the TriCat 12/G1-B formulation over two months at 4° C.

[FIG. 17] shows the NMR spectrum $^{31}$P—{$^1$H} in the presence of $D_2O$ and after adjustment of the pH to pH=7 of compound G1-B (B) and the MAS NMR spectrum $^{31}$P—{$^1$H} in the presence of $D_2O$ and after adjustment of the pH to pH=7 of the TriCat 12/G1-B vesicles in a xanthan gel (A) after 3 months storage at pH=4 at 25° C. in water protected from light.

[FIG. 18] shows the evolution of light transmission, after 1 day in water at room temperature, through a sample of TriCat 12/G1-B incorporated (bottom) or not (top) into a xanthan gel (physical stabilization).

[FIG. 19] shows the fluorescence quantification of the amount of G1-B-NIR dendrimer (G1-B dendrimer in its fluorescent form) formulated or not with the TriCat 12, which penetrated the pig ear skin (Franz cells) after 24 h at 35° C.

[FIG. 20] shows the observation by confocal microscopy of the fluorescence (in white) of the G1-B-NIR dendrimer (G1-B dendrimer in its fluorescent form) unformulated (A) and formulated with the TriCat 12 (B) which penetrated the pig ear skin (Franz cells) after 24 h at 35° C.

[FIG. 21] shows the observation by confocal microscopy of the fluorescence (in white) of the G1-B-NIR dendrimer (G1-B dendrimer in its fluorescent form) unformulated (A) and formulated with the TriCat 12+xanthan 1% (B) which penetrated the pig ear skin (Franz cells) after 24 h at 35° C.

[FIG. 22] shows the flow cytometric analysis of the morphology (size and granulosity) of monocytes (on the graphs, each point is a cell). The top graph shows the non-activated control monocytes. The bottom graph shows the monocytes cultured in the presence of the TriCat 12 vesicles loaded with the G1-B dendrimer. The activated monocytes are in the ellipse.

[FIG. 23] shows the therapeutic efficacy of the G1-B dendrimer and of the TriCat12 vesicles loaded with the G1-B dendrimer in the imiquimod-induced psoriasis mouse model. The clinical scores (top graph) are given as a function of time expressed in days. The histological scores are given on the lower graph. The "control" mice are the animals that were not treated.

[FIG. 24] shows the antiproliferative effect of compound G1-B, as a function of treatment time, on the N-TERT keratinocyte line (top graphs) and on primary human keratinocytes (bottom graphs).

[FIG. 25] shows the size distribution measured by DLS of the vesicles formed by the TriCat 12/G1-C (1/0.5) formulation

[FIG. 26] shows the phase transition temperature of the TriCat 12/G1-C formulation.

[FIG. 27] shows the measurement of the mean hydrodynamic diameter measured in DLS of the TriCat 12/G1-C formulation over one month at 4° C.

[FIG. 28] shows the fluorescence quantification of the amount of G1C-NIR dendrimer (G1C dendrimer in its fluorescent form) formulated with the TriCat 12, which penetrated the pig ear skin (Franz cells) after 24 h at 35° C.

[FIG. 29] shows the flow cytometric analysis of the morphology (size and granulosity) of monocytes (on the graphs, each point is a cell). The top graph shows the non-activated control monocytes. The bottom graphs show the monocytes cultured with the G1-C dendrimer at 3 concentrations 0.2 μM, 2 μM, and 20 μM. The activated monocytes are in the ellipse.

[FIG. 30] shows the size distribution measured by DLS of the vesicles formed by the TriCat 8/G1-B (1/0.5) formulation.

[FIG. 31] shows the size distribution measured by DLS of the vesicles formed by the TriCat 16/G1-B (1/0.5) formulation.

[FIG. 32] shows the measurement of the mean hydrodynamic diameter measured in DLS of the TriCat 16/G1-B formulation over 10 days at 4° C.

DESCRIPTION OF THE EMBODIMENTS

Figure 1:
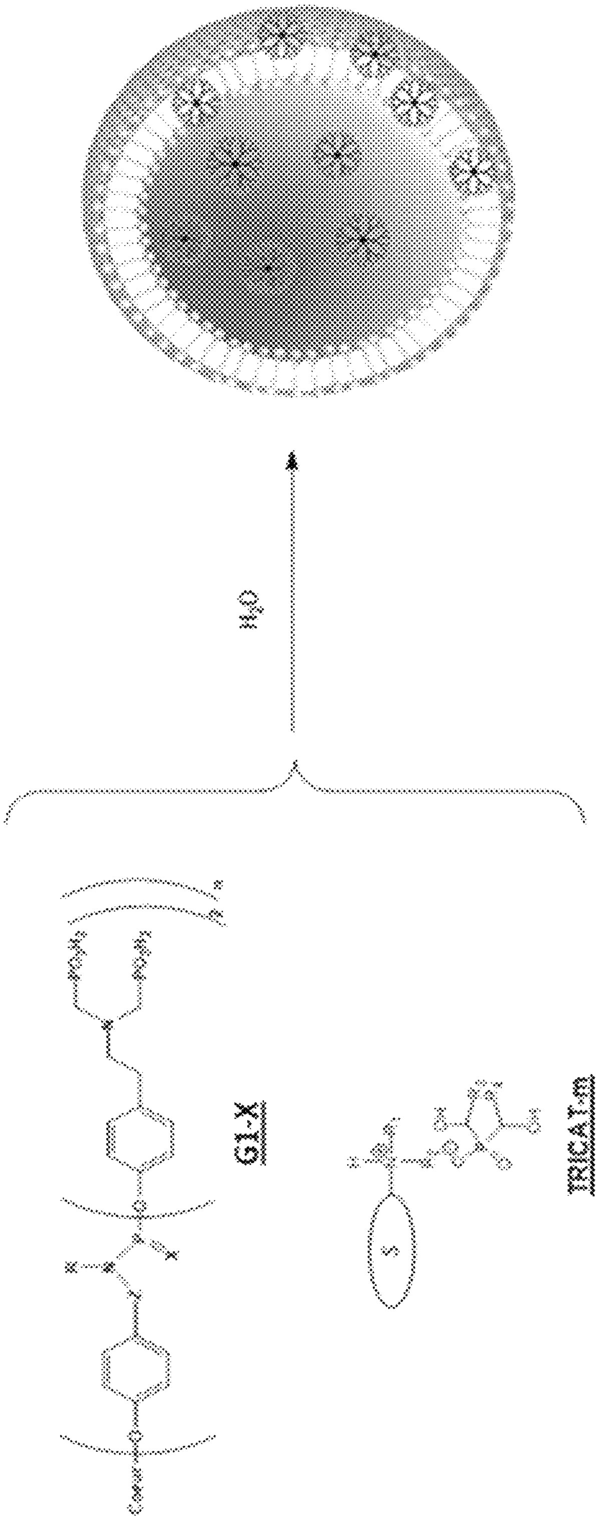
FIG. 1

The inventors have shown that the formulation of azabisphosphonate dendrimers in the phosphonic acid form with sugar-derived catanionic surfactants enhances the penetration of the dendrimer into the skin, thus improving its anti-inflammatory effect for the treatment of psoriasis.

The present invention thus relates to a vesicle comprising:

a catanionic surfactant of general formula (I) or a mixture of catanionic surfactants of general formula (I):

[Chem. 1]

(I)

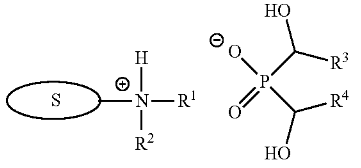

wherein

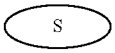

is a sugar, in particular

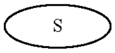

is selected from monosaccharides, disaccharides, polysaccharides and polyols, more particularly

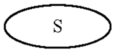

is a disaccharide or a polyol, even more particularly

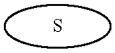

is 1-deoxylactilol, $R^1$ is selected from H and a linear or branched, saturated or unsaturated hydrocarbon chain of 1 to 20 links, in particular $R^1$ is selected from H and C1-C20-alkyl, more particularly $R^1$ is selected from H and C4-C18-alkyl, even more particularly $R^1$ is H, and $R^2$ is a linear or branched, saturated or unsaturated hydrocarbon chain with 1 to 20 links, in particular $R^2$ is $C_1$-C20-alkyl, more particularly $R^2$ is C4-C18-alkyl, even more particularly $R^2$ is C8-C16-alkyl, still more particularly $R^2$ is dodecyl, $R^3$ and $R^4$ are independently of each other a linear or branched, saturated or unsaturated hydrocarbon chain with 1 to 19 links, in particular $R^3$ and $R^4$ are independently of each other C1-C19-alkyl, more particularly $R^3$ and $R^4$ are C3-C17-alkyl, even more particularly $R^3$ and $R^4$ are C7-C15-alkyl, still more particularly $R^3$ and $R^4$ are undecyl; and a dendrimer of formula (II):

[Chem. 2]

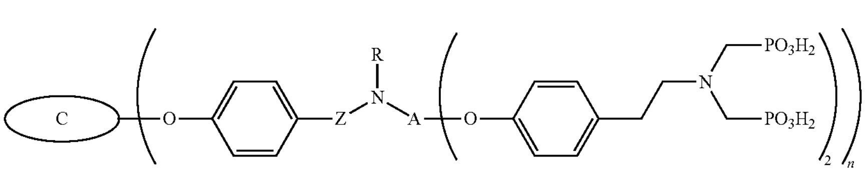

(II)

wherein

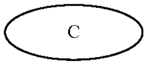

is selected from the pentoses, hexoses and the groups of the following formulas:

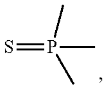
,
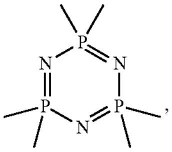
,
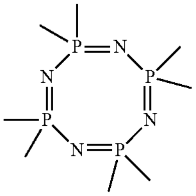
and

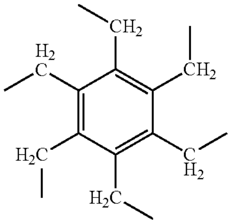

in particular

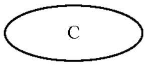

is selected from the groups of the following formulas:

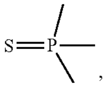
,
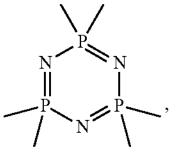
,
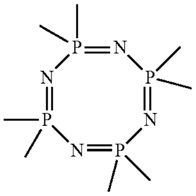
and

-continued

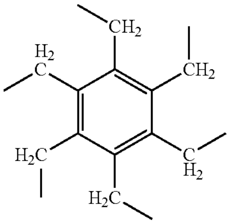
, more particularly

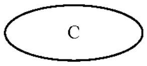

is selected from the groups of following formulas:

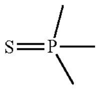,

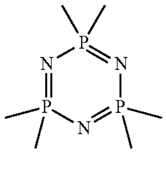

and

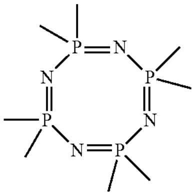, and even more particularly

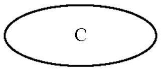

is

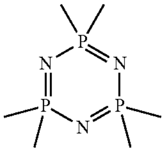;

Z is selected from $-CH_2-$ and $-CH{=}N-$,

R is selected from H and C1-C12-alkyl, in particular R is C1-C12-alkyl, more particularly R is C1-C8-alkyl, even more particularly R is $C_1$-$C_4$-alkyl, still more particularly R is selected from methyl, n-hexyl and n-octyl;

A is selected from

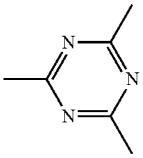

and

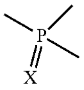, where X is selected from S and O; in particular A is

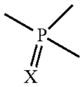, where X is selected from S and O; more particularly X is S, and n is an integer between 3 and 8, in particular n is equal to 6.

For the purposes of the present invention, "alkyl" means a hydrocarbon radical of formula $C_nH_{2n+1}$ wherein n is an integer greater than or equal to 1. The alkyl radicals may be linear or branched, preferably linear. Particular alkyl radicals of the invention are from 1 to 20 carbon atoms, more particularly from 1 to 12 carbon atoms.

For the purposes of the present invention, "sugar" means monosaccharides, disaccharides, polysaccharides, polyols and their derivatives.

Sugar derivatives include sugar-type radicals wherein a hydroxyl function has been removed. A particularly preferred sugar of the invention is 1-deoxylactilol.

In one embodiment, the vesicle according to the invention is characterized in that it comprises a single catanionic surfactant of formula (I).

In another embodiment, the vesicle according to the invention is characterized in that it comprises a mixture of catanionic surfactants of formula (I), in particular a mixture of two different catanionic surfactants of formula (I).

According to this embodiment, the molar ratio between the two different catanionic surfactants of formula (I) may be between 99/1 and 1/99.

In one particular embodiment, the vesicle according to the invention is characterized in that, in the catanionic surfactant of formula (I),

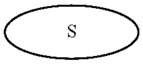

is 1-deoxylactilol.

Thus, according to this embodiment, the catanionic surfactant present in the formulation is that of formula (Ia):

[Chem. 3]

(Ia)

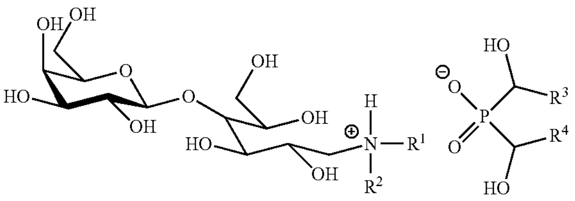

wherein $R^1$, $R^2$, $R^3$ and $R^4$ are as defined in formula (I).

In one embodiment, the vesicle according to the invention is characterized in that, in the dendrimer of formula (II),

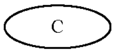

is

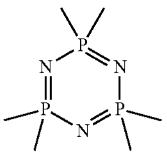.

is

Thus, according to this embodiment, the dendrimer present in the vesicle is that of formula (IIa):

[Chem. 4]

(IIa)

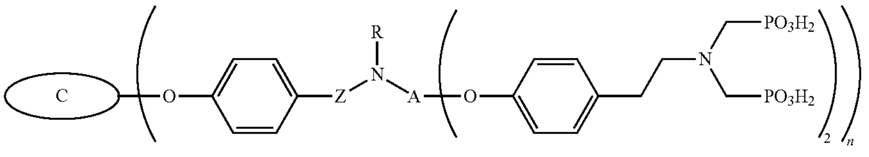

wherein Z, R, X and n are as defined in formula (II).

According to a variant of this embodiment, the dendrimer of formula (IIa) present in the vesicle is the one wherein Z is —CH═N—, According to another variant of this embodiment, the dendrimer of formula (IIa) present in the vesicle is the one wherein Z is —$CH_2$—.

In another variant of this embodiment, the dendrimer of formula (IIa) present in the vesicle is the one wherein A is

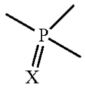

where X is selected from S and O.

According to another variant of this embodiment, the dendrimer of formula (IIa) present in the vesicle is the one wherein A is

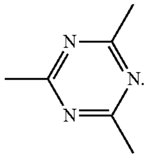

Advantageously, the molar ratio of catanionic surfactant to dendrimer in the vesicle according to the invention is between 50/1 and 1/1, in particular between 30/1 and 1/1, more particularly between 20/1 and 1/1, even more particularly between 10/1 and 1/1, still more particularly between 5/1 and 1/1. Most notably, the molar ratio of catanionic surfactant to dendrimer in the vesicle according to the invention is about 2/1.

The vesicle according to the invention encapsulates the dendrimer in the catanionic surfactant.

Advantageously, the encapsulation rate of the dendrimer of formula (I) in the catanionic surfactant of formula (II) is greater than 50%. In particular, the encapsulation rate of the dendrimer of formula (I) in the catanionic surfactant of formula (II) is between 50% and 95%, more particularly between 60% and 85%, even more particularly between 70% and 80%.

For the purposes of the present invention, "encapsulation rate" means the ratio between the number of mole of dendrimer stabilized in the catanionic surfactant to the number of moles of dendrimer initially used for the preparation of the vesicle. The encapsulation rate can be determined by all methods known to the person skilled in the art, in particular by UV-visible spectrophotometric or fluorescence spectroscopic determination.

Advantageously, the average diameter of the vesicles according to the invention is between 50 and 500 nm, in particular between 100 and 350 nm.

The average diameter can be determined by all methods known to the person skilled in the art, in particular by dynamic light scattering (DLS), especially by means of a He—Ne laser emitting monochromatic light with a wavelength of 633 nm.

Advantageously, the phase transition temperature of the vesicles according to the invention is between 3° and 35° C., in particular is 33° C.

Preparation Method

The present application also relates to a method for preparing the vesicles as previously described.

The catanionic surfactant of formula (I) present in the vesicle according to the invention is formed by the combination of an N-alkylaminosugar of formula (I'):

[Chem. 5]

(I')

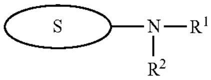

wherein

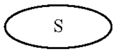

is a sugar $R^1$ is selected from H and a linear or branched, saturated or unsaturated hydrocarbon chain of 1 to 20 members, in particular $R^1$ is chosen from H and C1-C20-alkyl, $R^2$ is a linear or branched, saturated or unsaturated hydrocarbon chain with 1 to 20 links, in particular $R^2$ is C1-C20-alkyl;

and of a phosphinic acid of formula (I"):

[Chem. 6]

(I")

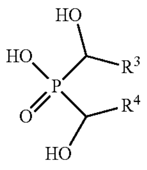

wherein $R^3$ and $R^4$ are independently of each other a linear or branched, saturated or unsaturated hydrocarbon chain with 1 to 19 links, in particular $R^3$ and $R^4$ are independently of each other C1-C19-alkyl.

Thus, the method for preparing a vesicle according to the invention comprises the following steps in succession:

(a) mixing one or more N-alkylaminosugars of formula (I'), in particular an N-alkylaminosugar of formula (I'), a phosphinic acid of formula (I") and the dendrimer of formula (II) as defined previously; and (b) optionally, separating the obtained vesicle from the unencapsulated dendrimer.

Advantageously, the mixing step is carried out in an aqueous solution, in particular in water.

Advantageously, the N-alkylaminosugar, the phosphinic acid and the dendrimer are mixed with a molar ratio between 100/50/1 and 1/1/1. In particular, the mixing step is carried out with a molar ratio of N-alkylaminosugar/phosphinic acid/dendrimer of 2/2/1.

The mixing may be carried out by all techniques known to the person skilled in the art, in particular by magnetic stirring, vortex stirring and/or ultrasonic sonication, more particularly by vortex stirring followed by magnetic stirring or ultrasonic sonication.

The mixing step can be carried out at room temperature or by heating to a temperature between room temperature and 100° C., in particular between 25° C. and 75° C., for a period of between 5 minutes and 72 hours, in particular between 10 minutes and 48 hours.

Once the mixing step is completed, the resulting vesicle can then be separated from the unencapsulated dendrimer.

The separation step may be carried out by all techniques known to the person skilled in the art, in particular by filtration.

Pharmaceutical Composition

The present patent application further relates to a pharmaceutical composition comprising the vesicle as previously described and a pharmaceutically acceptable excipient.

The term "pharmaceutically acceptable" refers only to ingredients of a pharmaceutical composition that are compatible with each other and not deleterious to the patient. In one embodiment, a pharmaceutically acceptable excipient does not produce a side effect, allergic or other adverse reaction when administered to an animal, preferably a human. For human administration, preparations must meet standard criteria for sterility, pyrogenicity, general safety, and purity as required by regulatory agencies, such as the FDA or EMA.

In particular, the pharmaceutical composition as previously described will be for topical or transcutaneous application.

Thus, the pharmaceutical composition as previously described may comprise a pharmaceutically acceptable excipient(s) for a formulation suitable for topical administration.

The pharmaceutically acceptable excipients may in particular be any excipient among those known to the person skilled in the art in order to obtain a composition for topical application in the form of a milk, a cream, a balm, an oil, a lotion, a gel, a foaming gel, an ointment, or a spray, preferably in the form of a gel.

In particular, the pharmaceutical excipients can be gelling agents selected from: carbomers, polysaccharides, such as xanthan gum, guar gum, chitosans, carrageenans, cellulose and its derivatives such as hydroxypropylmethylcellulose in particular or hydroxyethylcellulose available under the name Natrosol, or the family of aluminum and magnesium silicates, the family of acrylic polymers, the family of modified starches and gelling agents of the polyacrylamide family. Preferably, the pharmaceutical excipient comprises hydroxyethyl cellulose, chitosan or xanthan, preferably xanthan.

Therapeutic Use

In the present application, the inventors have shown that the dendrimers according to the invention have, in addition to an anti-inflammatory effect, an anti-proliferative effect on keratinocytes. The formulation of the dendrimers in vesicles according to the invention allows the active ingredient to cross the stratum corneum and reach the region of proliferation of the keratinocytes in the deep epidermis.

The present patent application relates to the vesicle or the pharmaceutical composition of the invention as previously described for use in the treatment or prevention of a dermatosis related to keratinocyte hyperproliferation and/or an inflammatory context, preferably psoriasis, dermatitis such as atopic dermatitis, contact dermatitis, seborrheic dermatitis or ichthyoses, such as erythematous ichthyoses (rare diseases) such as Peeling Skin Syndrome (PSS) of type 1 or 6 or congenital ichthyosiform erythroderma, squamous cell carcinomas, basal or squamous cell carcinomas, or acne.

In particular, the present patent application relates to the vesicle or pharmaceutical composition of the invention as previously described for use in the treatment or prevention of a dermatosis related to keratinocyte hyperproliferation and an inflammatory context, preferably, dermatitis such as atopic dermatitis, contact dermatitis, seborrheic dermatitis or ichthyoses, such as erythematous ichthyoses (rare diseases) such as Peeling Skin Syndrome (PSS) of type 1 or 6, or congenital ichthyosiform erythroderma.

Dermatitis is an irritation of the skin. Dermatitis is a common condition and comes in many forms. It usually manifests itself as itching, dry skin or a rash on swollen and reddened skin. It can also cause blistering, oozing, crusting or scaling.

Preferably, the vesicle or pharmaceutical composition of the invention as previously described is particularly useful for treating atopic dermatitis, contact dermatitis and seborrheic dermatitis.

Atopic dermatitis, also called atopic eczema, is a chronic inflammatory skin disease. It develops preferentially in infants and children, but can persist or even appear sometimes in adolescents and adults. It is characterized by skin dryness associated with eczema-type lesions (redness and itching, vesicles, oozing and crusts) that flare up. Atopic dermatitis is a chronic inflammatory skin disease.

Contact dermatitis is a skin reaction resulting from exposure to allergenic (allergic contact dermatitis) or irritant (irritant dermatitis) substances. The skin reaction usually develops within minutes to hours after exposure to the substance and may last two to four weeks.

Seborrheic dermatitis usually affects the scalp and causes scaly patches, red skin and stubborn dandruff. It can also affect oily areas of the body, such as the face, upper chest and back. Seborrheic dermatitis can be a long-term condition, with periods of improvement and then seasonal flare-ups. In infants, this condition is called "cradle cap".

The vesicle or pharmaceutical composition of the invention as previously described is also particularly useful for treating ichthyosis, preferably erythematous ichthyoses such as Peeling Skin Syndrome (PSS) type 1 or 6 or congenital ichthyosiform erythroderma.

Ichthyosis is a congenital skin disease characterized by extremely dry, rough skin, by the presence of an excessive amount of fine, loose-edged scales that are sometimes arranged like fish scales and are continuously shed. Erythematous ichthyosis is an ichthyosis with a dermatological lesion characterized by diffuse or localized congestive redness of the skin that clears on vitopression.

Peeling skin syndrome of type 1 and 6 are inflammatory forms of ichthyosis characterized by diffuse and superficial scaling of the entire skin surface with underlying erythroderma, pruritus and atopy.

Congenital ichthyosiform erythroderma is characterized by the presence from birth of fine white-grayish scales of various sizes, associated with erythroderma. Some newborns are wrapped in a film of soft collodion (tight, shiny and translucent) and develop a scaly erythroderma after its peeling.

The present patent application is also directed to the vesicle or pharmaceutical composition as previously described for use in the treatment or prevention of a dermatosis related to a hyperproliferation of the keratinocytes, such as basal or squamous cell carcinoma.

Basal cell carcinoma is a type of skin cancer that begins in the basal cells. Basal cell carcinoma often appears as a slightly transparent bump on the skin, although it can take other forms. Basal cell carcinoma most often appears on areas of the skin that are exposed to the sun, such as the head and neck.

Squamous cell carcinoma is a common form of skin cancer that develops in the squamous cells that make up the middle and outer layers of the skin. Squamous cell carcinoma most often occurs on sun-exposed skin, such as the scalp, back of the hands, ears or lips.

The present application also relates to the vesicle or the pharmaceutical composition of the invention as previously described for its use in the treatment or prevention of a dermatosis related to an inflammatory context such as acne.

Acne is a common and chronic dermatological disease of the pilosebaceous system (which includes the hair follicle, the hair shaft and the sebaceous gland that secretes sebum at the root of the hair). It usually occurs in adolescence and is related to the hypersecretion of sebum (hyperseborrhea) and to keratinization abnormalities leading to the obstruction of the excretory canal of the pilosebaceous follicle, and to the formation of comedones.

Preferably, the present patent application is also directed to the vesicle or pharmaceutical composition as previously described for use in the treatment of psoriasis in a subject in need thereof.

Psoriasis is a dermatosis linked to hyperproliferation of keratinocytes, cells making up 90% of the epidermis, and to a chronic inflammatory context. In this pathology, keratinocytes play a role, along with skin immune cells and infiltrating immune cells. The hyperproliferation of keratinocytes is accompanied by a defect in differentiation when they reach the most superficial layer of the epidermis, the stratum corneum, resulting in the characteristic scaly patches of the disease. In psoriasis, the renewal of the different layers of the epidermis takes place in 3 to 4 days, compared to 3 weeks for normal skin. In order to control hyperproliferation and the inflammatory context, it is therefore necessary to reach these cellular drivers of the disease by allowing the active ingredient to cross the stratum corneum, which constitutes the skin's waterproof barrier. The formulation of the dendrimers in vesicles according to the invention allows the active ingredient to cross the stratum corneum and reach the hyperproliferation site of the keratinocytes in the deep epidermis. Thus, the vesicle or pharmaceutical composition according to the application is particularly useful for the treatment of psoriasis.

"Psoriasis" means a chronic inflammatory skin disease that causes abnormal skin turnover resulting in thick red patches covered with scales. Psoriasis includes all forms of psoriasis, including plaque psoriasis, guttate psoriasis, psoriasis in infants, pustular psoriasis, erythrodermic psoriasis, inverted psoriasis, facial psoriasis, scalp psoriasis, mucous membrane psoriasis. Plaque psoriasis, or psoriasis vulgaris, is the most common form of psoriasis, affecting more than 80% of patients, and is characterized by raised red plaques with white scales on the surface. Guttate psoriasis, which affects nearly 10% of patients, is characterized by multiple teardrop-shaped lesions with few scales. Pustular psoriasis is the most severe form of psoriasis wherein the plaques are covered with non-infectious white pustules. Erythrodermic psoriasis is a generalized inflammation with scales wherein 90 to 100% of the skin is affected. Inverse psoriasis is characterized by the presence of non-scaly patches inside the joints and folds.

The term "subject" refers to an animal, more particularly a mammal. Preferably, the subject is a human being. For the purposes of the present invention, a subject may be a patient, that is, a person receiving medical care, undergoing or having undergone medical treatment, or being monitored in the course of developing a disease.

The term "treat" or "treatment" refers to both therapeutic treatment and prophylactic or preventive measures, wherein the goal is to prevent or slow down (decrease) the targeted pathological condition, in particular keratinocyte proliferation and skin inflammation. Preferably, in the case of psoriasis treatment, the objective is to reduce the surface area of the affected skin, the degree of redness of the lesions, their thickness, and the intensity of desquamation.

In particular, the vesicle or composition as previously described for its use as a medicament, in particular for the treatment or prevention of a dermatosis related to keratinocyte hyperproliferation and/or an inflammatory context, preferably for the treatment of psoriasis, are characterized in that they are formulated for topical application.

According to another one of its aspects, the present invention relates to a method of treating or preventing a dermatosis related to keratinocyte hyperproliferation and/or an inflammatory context in a subject in need thereof, comprising administering, to a subject, a therapeutically effective dose of a vesicle or a pharmaceutical composition according to the invention. Preferably, the subject is an animal, preferably a mammal, more preferentially a human suffering from a dermatosis linked to hyperproliferation of keratinocytes and/or an inflammatory context.

The present invention also relates to the use of a vesicle or a pharmaceutical composition as previously described for the manufacture of a medicament for the treatment or prevention of a dermatosis related to keratinocyte hyperproliferation and/or an inflammatory context.

The present patent application further relates to a method of treating psoriasis in a subject in need thereof, comprising administering a therapeutically effective dose of the vesicle or composition as previously described to said subject. In particular, an object of the present application is a method of treating psoriasis in a subject in need thereof, comprising topically administering a therapeutically effective dose of the vesicle or pharmaceutical composition as previously described to said subject.

The present invention also relates to the use of a vesicle or pharmaceutical composition as previously described for the manufacture of a medicament for the treatment or prevention of psoriasis.

The term "therapeutically effective dose" refers to the dose of therapeutic agent necessary and sufficient to slow or stop the progression, worsening or deterioration of one or more symptoms of a dermatosis related to keratinocyte hyperproliferation and/or an inflammatory context as previously described, preferably psoriasis disease, for example, reducing the surface area of affected skin, the degree of redness of the lesions, their thickness, and the intensity of desquamation.

According to one embodiment, the vesicle or a pharmaceutical composition as previously described can be used as a medicament in particular for the treatment or prevention of a dermatosis related to a keratinocyte hyperproliferation and/or an inflammatory context as previously described, preferably psoriasis in a subject in combination with at least one other therapeutic agent. Such additional therapeutic agents include, but are not limited to, anti-inflammatory agents, anti-infectious agents, and immunosuppressive agents. The vesicle and the additional therapeutic agent can be administered at the same time or at different times, simultaneously or separately.

Thus, the methods of treatment and pharmaceutical compositions of the present invention can use the vesicle of the invention as a monotherapy, but these methods and compositions can also be used as a combination therapy wherein the vesicles of the invention are co-administered in combination with one or more other therapeutic agents The present invention will be better understood in light of the following non-limiting examples and figures.

EXAMPLES

I. Material and Methods

1. Synthesizing the Compounds Used

N-dodecylamino-1-deoxylactitol was synthesized according to the protocol described in the thesis of Pauline Castagnos (thesis Castagnos, Pauline (2011). *Vésicules catanioniques: design et mecanismes de délivrance de principes actifs*) (Catanionic vesicles: design and delivery mechanisms of active ingredients). 8.75 mmol (i.e. 3.15 g) of α-lactose are dissolved in 20 mL of ultrapure water. 14.88 mmol (i.e. 2.76 g) of dodecylamine are dissolved in 25 mL of methanol. 5% by weight (relative to the total mass of reagents) of palladium supported on carbon (i.e. 0.338 g) is suspended in 10 mL of methanol. The amine, palladium and finally lactose are placed in a firmly screwed-shut reactor.

After three purges under 20 bar of hydrogen, the reactor is filled with hydrogen under 22 bar then disconnected from the hydrogen cylinder and placed in a sand bath thermostated at 60° C., so as to have a temperature of about 50° C. in the reactor. The reaction medium is thus left under magnetic stirring for 3 days. After cooling the reactor, the reaction medium is returned to atmospheric pressure.

In order to remove the excess palladium, a celite filtration of the reaction medium is carried out using a porosity filter 5. After packing the celite with ultrapure water, the reaction medium heated to 50° C. is deposited on it, then washed with 200 mL of ultrapure water/methanol solution (1:1) at 50° C. The filtrate is then dried in a rotary evaporator. When only water remains, it is removed by freeze-drying. A white hygroscopic powder is recovered (m=1.62 g, R=36%).

$^1$H NMR ($D_2O$, 300 MHZ): δ (ppm): 0.81 (m, 3H, $CH_3$); 1.48 (m, 20H, $CH_2$ aliphatic); 3.48 to 3.84 (m, 20H, OH, CH and $CH_2$ of sugar); 4.42 (d, 1H, anomeric H)

MS: m/z: 512.4

FT-IR (KBr): $v_{max}$ ($cm^{-1}$): 3435 (N—H st (secondary amine), alcohols), 2924 (C—H elongation), 2853 (CH, $CH_2$, $CH_3$ elongation), 1638 (N—H elongation), 1466 (angular deformation $CH_2$), 1380 (C—H), 1079 (C—N st (secondary amine)), 720 (N—H b, presence of an aliphatic chain greater than 4C)

Elemental analysis: C: 53.90%, H: 9.68%, N: 2.79%, Pd<0.02% ($C_{theo}$: 56.34%; $H_{theo}$: 9.65%; $N_{theo}$: 2.74%)

Carbon purity: 95.7%

Bis-α-(hydroxydodecyl)phosphinic acid was synthesized according to the protocol described in the article (Brun, A.; Etemad-Moghadam, G. New double-chain and aromatic (alpha-hydroxyalkyl)phosphorus amphiphiles. *Synthesis* 2002, 10, 1385-1390.)

2.5 mmol of sodium hypophosphite monohydrate (i.e. 2.38 g) are stirred in the presence of 30 mL of 1,4-dioxane. 56 mmol of dodecylaldehyde (i.e. 10.3 g) are added, as well as 4 mL of 37% hydrochloric acid. The reaction mixture is heated at reflux (101° C.) for 24 h. After cooling, the flask is passed through the rotary evaporator until a solid brown paste is obtained. The latter is washed successively with 15 mL ultrapure water, 15 mL tetrahydrofuran (THF), 4×15 mL acetone, 15 mL ultrapure water, 15 mL tetrahydrofuran, 4×15 mL acetone and 15 mL tetrahydrofuran. The washes are all carried out using a sinter of porosity 4. A white compact powder is obtained (m=2.00 g, R=20.5%).

$^1$H NMR ($CDCl_3/CD_3OD$, locked $CD_3OD$, 55° C., 300 MHz): b (ppm): 0.85 (t, 6H, $CH_3$); 1.25 (m, 36H, $CH_2$ aliphatic); 1.61 (m, 4H, $CH_2$ in a); 1.77 (m, 4H, $CH_2$ α); 3.60 (m, 2H of CHOH)

$^{13}$C NMR ($CDCl_3/CD_3OD$, locked $CD_3OD$, 55° C., 300 MHz): b (ppm): 13.6 (s, $CH_3$); 22.4 to 31.7 ($CH_2$), between 60 and 70 (CH)

$^{31}$P NMR ($CDCl_3/CD_3OD$, locked $CD_3OD$, 55° C., 300 MHz): b (ppm): 45.43 and 46.52: peaks due to the pseudo-asymmetry of phosphorus. No peak around 30 ppm: no monosubstituted remnants

MS: 433.3 (M-H)-

FT-IR (KBr): $v_{max}$ ($cm^{-1}$): 3313 (C—OH); 2918 (C—H); 2848 (C—H); 2369 (P—OH); 1465 (δ$CH_2$); 1222 (P=0); 1141 (P=0); 1115 (PO—OH); 1067 (P—OH); 960 (P—OH); 941 (P—OH)

Elemental analysis: C: 65.67%, H: 9.18% ($C_{theo}$: 66.32%; $H_{theo}$: 11.83%)

Carbon purity: 99.0%

ABP Dendrimer

[Chem 7]

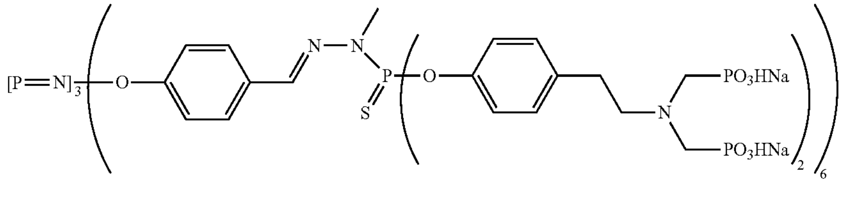

The ABP dendrimer was synthesized according to the protocol described in Poupot et al. FASEB J. 2006, 20(13) 2339-51.
G1-A Dendrimer
[Chem 8]
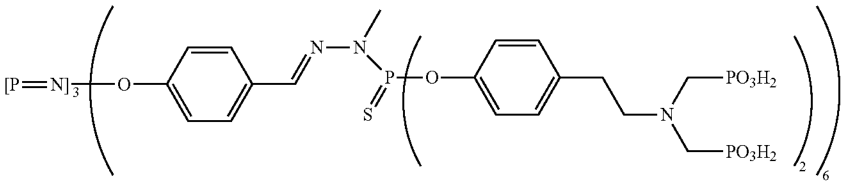
The G1-A dendrimer was synthesized according to the protocol described in Poupot et al. FASEB J. 2006, 20(13) 2339-51.
G1-A-NIR Dendrimer Synthesis diagram [diagram 1]
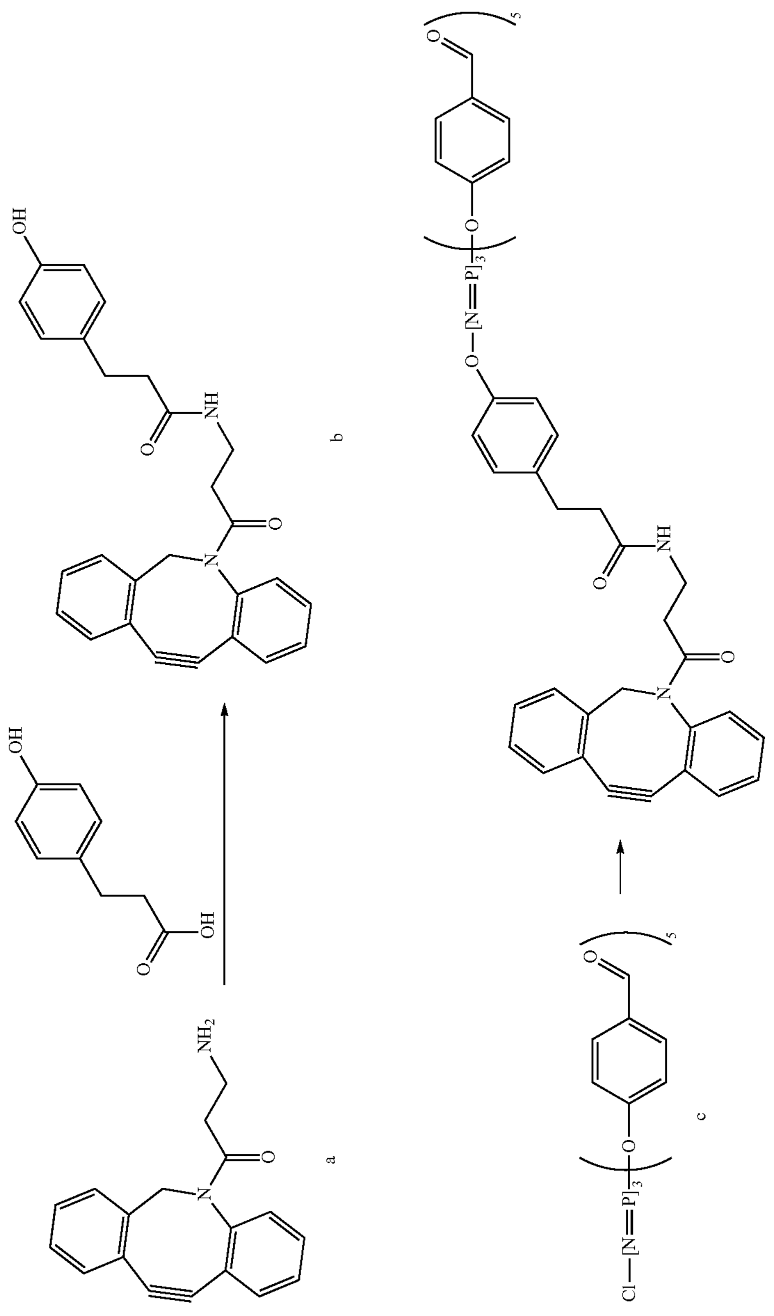
a b c d -continued
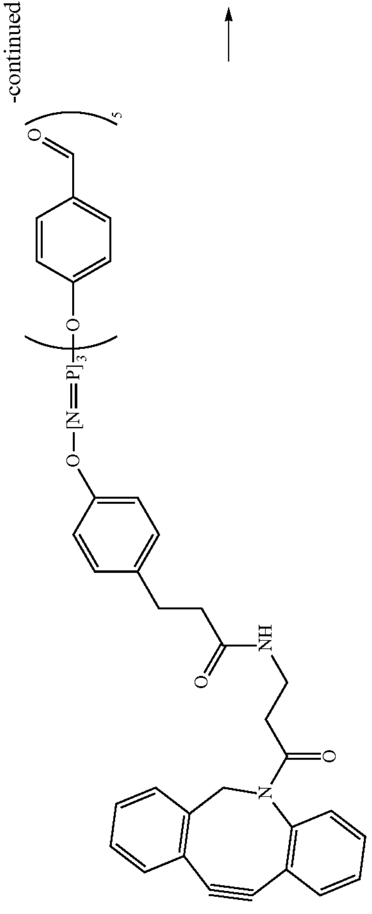
d
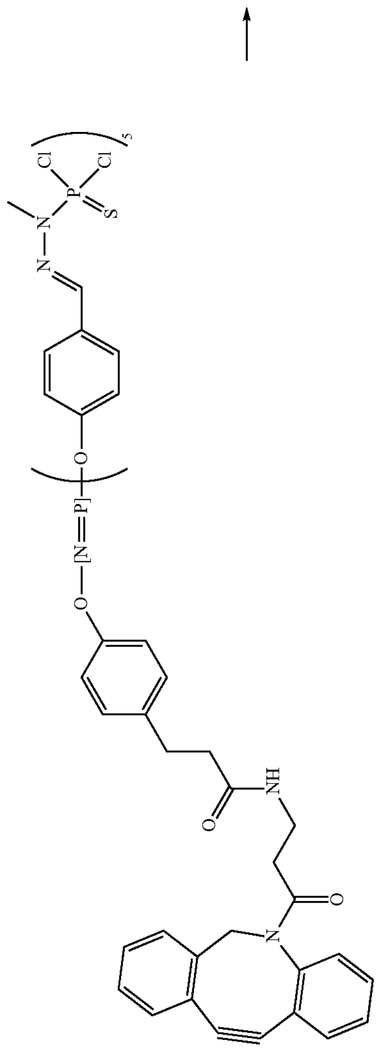
e -continued
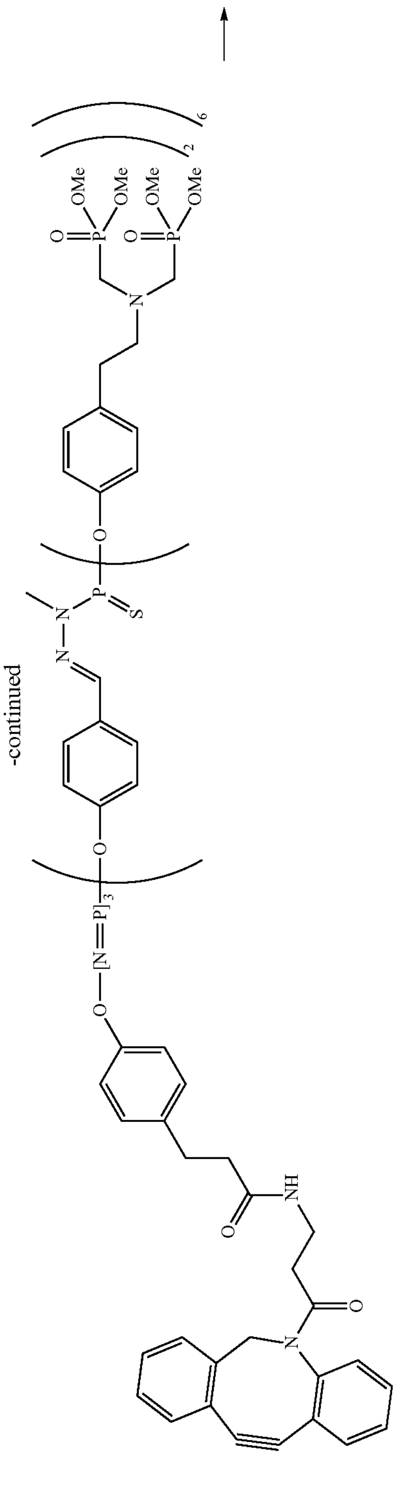
f
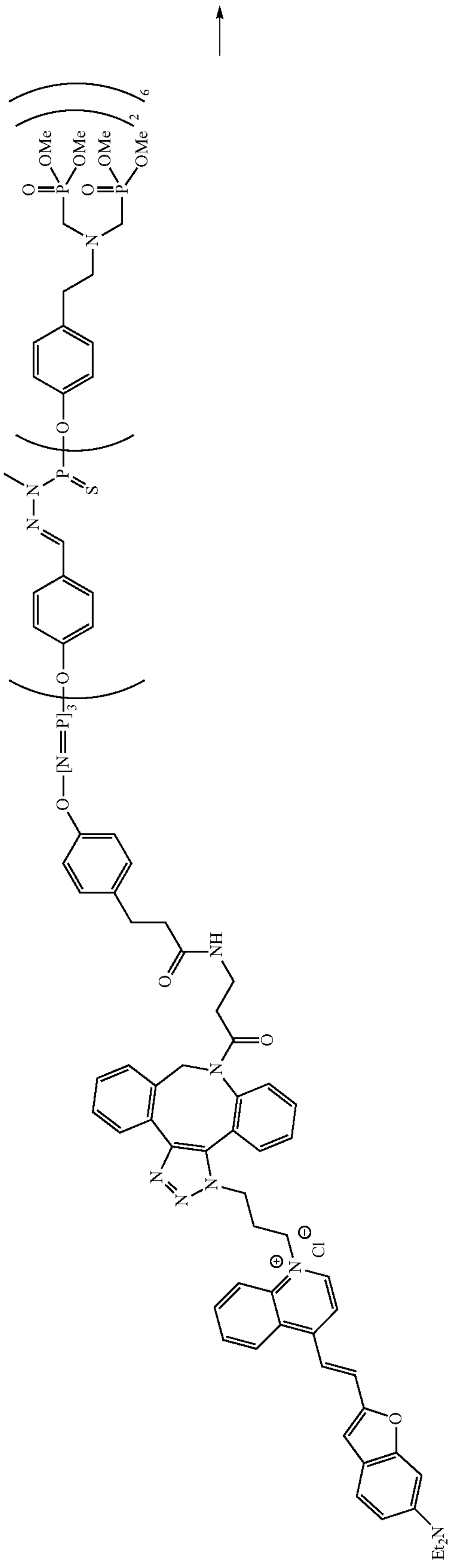
g -continued
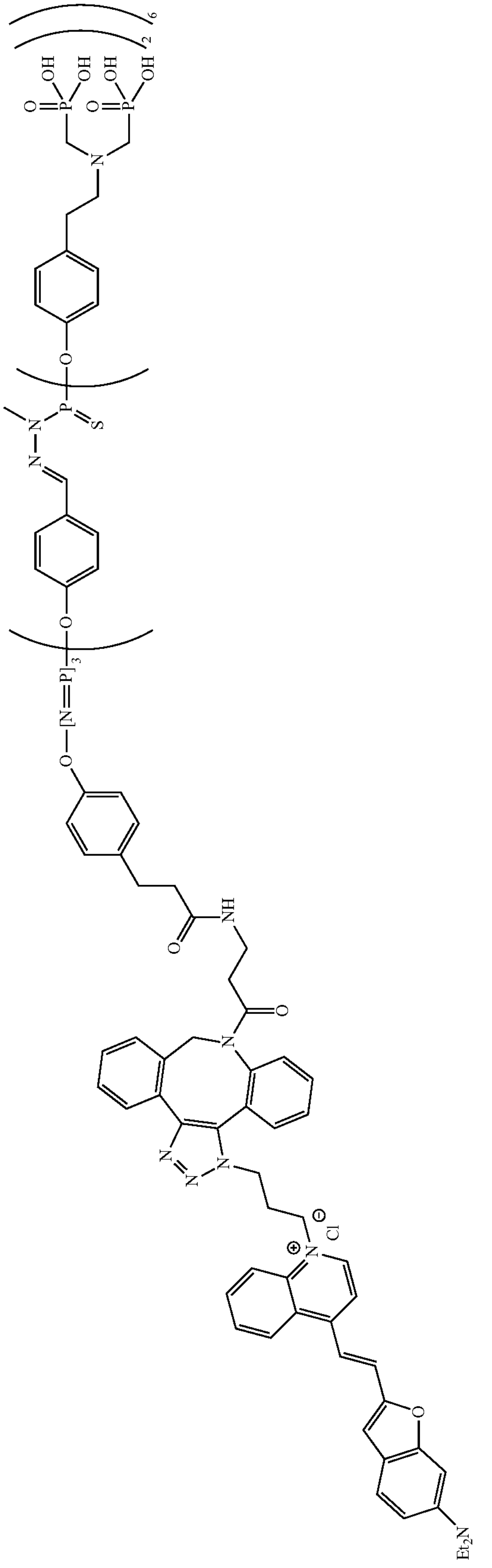

Synthesis of Compound b

4-Hydroxy-benzenepropanoic acid (90 mg, 0.54 mmol), 1-Ethyl-3-(3-dimethylaminopropyl) carbodiimide (EDC) (90.18 mg, 0.47 mmol), and 1.1 equivalents of 4-dimethylaminopyridine (DMAP) (48.64 mg, 0.39 mmol) are added to a solution of ADIBO-amine a (100 mg, 0.36 mmol) in 5 mL of N,N-dimethylformamide DMF. The reaction mixture is stirred overnight at room temperature. The reaction medium is freeze-dried, the crude residue is solubilized in 50 mL of dichloromethane (DCM) then washed with water (3×25 mL). The organic phase is dried and concentrated under reduced pressure. The residue is purified on a silica column (eluent: hexane/AcOEt, 60/40) to give product b with a yield of 85% in the form of a clear oil.

[Chem 9]

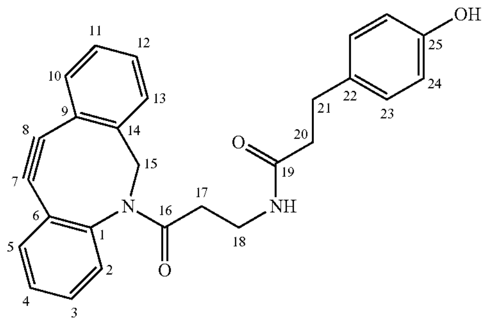

$^1$H NMR (500 MHz, Chloroform-d) δ:2.01-1.92 (m, 1H, $CH_2$—CON), 2.30-2.23 (m, 2H, $C'_0{}^4$—$CH_2$—), 2.50-2.50 (m, 2H, $CH_2$—CON), 2.80-2.69 (m, 3H, —$CH_2$—CO—NH—), 3.25-3.19 (m, 1H, —$CH_2$—NH—CO), 3.39-3.32 (m, 1H, —$CH_2$—NH—CO), 3.72 (d, $^2J_{HH}$=13.9 Hz, 1H, r-$CH_2$—N—CO—), 5.16 (d, $^2J_{HH}$=13.9 Hz, 1H, r-$CH_2$—N—CO—), 6.14-6.08 (t, $^3J_{HH}$=6.0 Hz, 1H, CO—NH), 6.71 (d, $^2J_{HH}$=8.2 Hz, 4H, $C'_0{}^3$H), 6.95 (d, $^3J_{HH}$=8.2 Hz, 4H, $C'_0{}^2$H), 7.17 (br s, 1H, $H_{Ar}$), 7.23-7.27 (m, 1H, $H_{Ar}$), 7.35-7.27 (m, 2H, $H_{Ar}$), 7.49-7.35 (m, 4H, $H_{Ar}$), 7.70 (d, $^3J_{HH}$=7.6 Hz, 2H, $H_{Ar}$), 8.04 (s, 1H, OH) ppm.

$^{13}$C NMR (126 MHz, Chloroform-d) δ: 30.80 (—$CH_2$—CO—NH—). 34.75 (s, $CH_2$—CON), 35.22 (s, —$CH_2$—NH—CO), 38.55 (s, $C'_0{}^4$—$CH_2$—), 55.63 (—$CH_2$—N—CO), 107.74 (s, C≡C'), 114.79 (s, C≡C'), 115.38 (s, $C'_0{}^2$), 122.48 (s, $C_f$), 122.91 (s, $C_f$'), 125.66 (s, $C_e$'), 127.27 (s, $CH_{Ar}$), 127.93 (s, $CH_{Ar}$), 128.37 (s, $CH_{Ar}$), 128.53 (s, $CH_{Ar}$), 128.69 (s, $CH_{Ar}$), 129.05 (s, $C_0{}^3$), 129.29 (s, $CH_{Ar}$), 131.96 (s, $C'_0{}^4$), 132.09 (s, $CH_{Ar}$), 147.91 (s, $C_{Ar}$), 150.88 (s, $C_{Ar}$), 154.81 (s, C'o$^1$), 172.44 (s, CONH) ppm.

Synthesis of Compound d

To a solution of compound b (130 mg, 0.30 mmol) in THF (30 mL) with $CS_2CO_3$ (199 mg, 0.61 mmol), compound c (465 mg, 0.6 mmol) is added. After one night of stirring at room temperature, the mixture is centrifuged, filtered, then concentrated under reduced pressure. The crude residue is purified on a silica column (eluent: DCM/AcOEt, 60/40) to give compound d with an 88% yield in the form of a clear oil. Compound c can be prepared according to Rolland, O. et al. (2008) Chemistry—A European Journal, 14: 4836-4850.

[Chem 10]

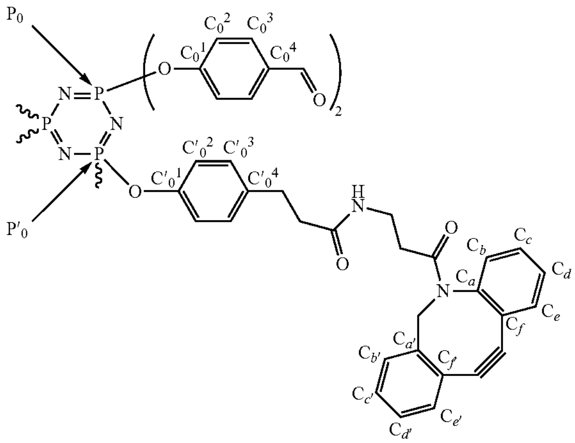

$^{31}$P NMR (121 MHz, Chloroform-d) δ: 7.40 (s, P═N).

$^1$H NMR (600 MHz, Acetone-d6) δ: 1.96-1.88 (m, 1H, $CH_2$CON). 2.34-2.31 (m, 2H, $CH_2$—C'O$^4$), 2.44-2.48 (m, 0.5H—, $CH_2$CON), 2.47-2.53 (m, 0.5H—, $CH_2$CON), 2.82-2.79 (m, 2H, $CH_2$CONH), 3.17-3.12 (m, 1H, $CH_2$NH—), 3.26-3.20 (m, 1H, $CH_2$NH—), 3.65 (d, $^1J_{HH}$=14.0 Hz, 1H, $CH_2$NCO), 5.12 (d, $^1J_{HH}$=14.0 Hz, 1H, $CH_2$NCO), 6.79 (t, 3$J_{HH}$=6.1 HZ, 1H, CONH), 7.01-6.97 (m, 2H, C'o$^2$H), 7.13 (d, $^3J_{HH}$=8.4 Hz, 2H, $C'_0{}^3$H), 7.21 (d, $^3J_{HH}$=8.4 Hz, 4H, $C_0{}^2$H), 7.26-7.23 (m, 1H, $CH_{Ar}$), 7.29-7.27 (m, 6H, $C_0{}^2$H), 7.33-7.30 (m, 1H, $H_{Ar}$), 7.36-7.40 (m, 1H, $CH_{Ar}$), 7.49-7.45 (m, 2H, $CH_{Ar}$), 7.54-7.51 (m, 1H, $H_{Ar}$), 7.67 (d, $^3J_{HH}$=7.4 Hz, 1H, $CH_{Ar}$), 7.85-7.84 (m, 2H, $C_0{}^3$H), 7.86-7.85 (m, 5H, $C_0{}^3$H), 7.87-7.86 (m, 3H, $C_0{}^3$H), 9.99 (s, 3H, CHO), 10.00 (s, 1H, CHO), 10.01 (s, 1H, CHO).

$^{13}$C NMR (151 MHz, Acetone-d6) δ: 30.43 (s, $CH_2$CONH), 34.52 (s, $CH_2$CON), 35.29 (s, $CH_2$NH—), 37.08 (s, $CH_2$—$C'_0{}^4$), 54.95 (s, —$CH_2$NCO), 107.98 (s, C≡C), 114.35 (s, C≡C), 120.59 (s, $C'_0{}^2$H), 121.27 (s, $C_0{}^2$H), 121.35 (s, $C_0{}^2$H), 122.15 (s, $C_{Ar}$), 123.05 (s, $C_{Ar}$), 125.17 (s, $CH_{Ar}$), 126.87 (s, $CH_{Ar}$), 127.60 (s, $CH_{Ar}$), 127.92 (s, $CH_{Ar}$), 128.10 (s, $CH_{Ar}$), 128.79 (s, $CH_{Ar}$), 129.46 (s, $C'_0{}^3$H), 131.30 (s, $C_0{}^3$H), 131.34 (s, $C_0{}^3$H), 132.51 (s, $CH_{Ar}$), 133.98 (s, $C_{Ar}$), 134.05 (s $CH_{Ar}$), 134.11 (s, $CH_{Ar}$), 139.32 (br s, $C_{Ar}$, $C'_0{}^4$), 148.11 (br s, $C_{Ar}$, $C'_0{}^1$), 148.62 (s $C_{Ar}$), 151.80 (s, $C_{Ar}$), 154.46 (br s, Cq, $C_0{}^1$), 154.65 (br s, Cq, $C_0{}^1$), 170.64 (s, CON), 170.85 (s, CONH), 190.65 (s, CHO), 190.80 (s, CHO).

Compound e

To a solution of compound d (300 mg, 0.25 mmpl) in 10 mL of $CHCl_3$, 7 equivalents of 0.2 M dichlorothiophospho (N-methyl)hydrazide (8.75 mL, 1.75 mmol) in chloroform are added. The reaction mixture is left under stirring for 2 hours at room temperature. At the end of the reaction (checked by 1H NMR), the solvent is concentrated under reduced pressure. The residue obtained is solubilized in 2 mL THF and then precipitated by being added to a large volume of pentane (100 mL). The solid formed is filtered and dried to obtain compound e with an 83% yield in the form of a white powder.

[Chem 11]

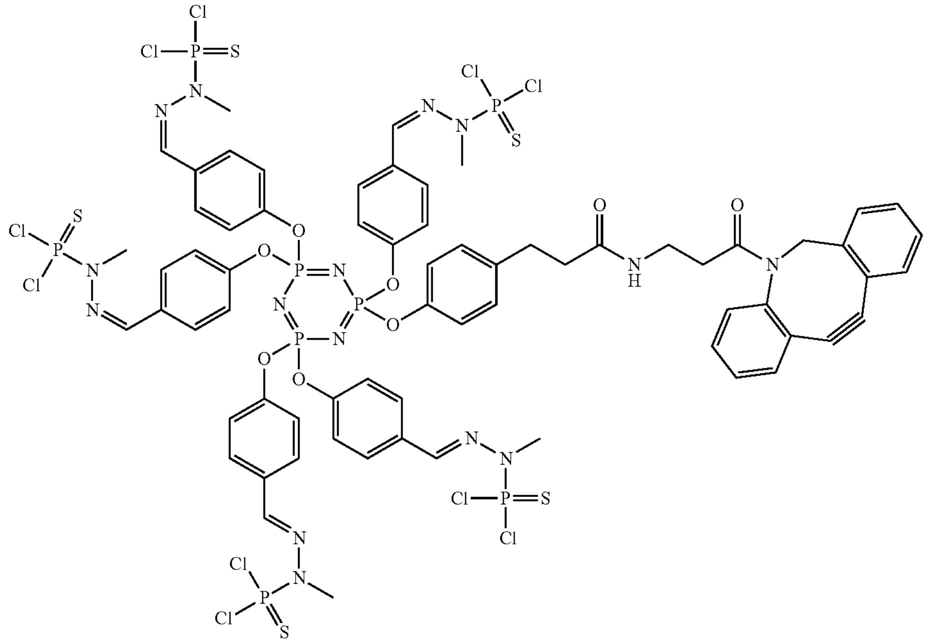

$^{31}P$ NMR (243 MHz, Chloroform-d) δ: 8.30 (s, N═P), 62.42 (s, P═S), 62.47 (s, P═S), 62.57 (s, P═S).

$^{1}H$ NMR (600 MHz, Chloroform-d) δ: 1.96-1.91 (m, 1H, —$CH_2$CON—), 2.25 (t, $3J_{HH}$=7.8 Hz, 2H, —$CH_2$—$C'_0{}^4$), 2.44-2.39 (m, 1H, $CH_2$CON—), 2.84-2.76 (m, 2H, —$CH_2$—CONH—), 3.22-3.14 (m, 1H, —$CH_2$—NHCO), 3.37-3.33 (m, 1H, —$CH_2$—NHCO), 3.50 (d, $^3J_{HH}$=13.9, 15H, $CH_3$—NPS), 3.69 (d, $^1J_{HH}$=14.0 Hz, 1H, —$CH_2$—NCO), 5.13 (d, $^1J_{HH}$=14.0 Hz, 1H, —$CH_2$—NCO), 6.01 (t, $3J_{HH}$=6.2 Hz, 1H, —CONH—), 6.92 (d, $^3J_{HH}$=8.1 Hz, 2H, $C'_0{}^2H$), 7.02-6.98 (m, 4H, $C_0{}^2H$, 2H, $C'_0{}^3H$), 7.06 (d, $^3J_{HH}$=8.2 Hz, 6H, $C_0{}^2H$), 7.21 (d, $^3J_{HH}$=7.6 Hz, 1H, $H_{Ar}$), 7.29 (d, $^3J_{HH}$=6.1 Hz, 3H, $H_{Ar}$), 7.44-7.35 (m, 3H, $H_{Ar}$), 7.61-7.58 (m, $3J_{HH}$=8.7 Hz, 10H, $C_0{}^3H$), 7.64 (s, 4H, —CH═N—), 7.66 (s, 1H, —$CH_{Ar}$), 7.68 (s, 2H, —CH═N—).

$^{13}C$ NMR (151 MHz, Chloroform-d) δ: 30.76 (s, $CH_2$CONH), 31.96 (d, $^2J_{CP}$=12.6 Hz, $CH_3$—NPS), 34.72 (s, —$CH_2$CON—), 35.21 (s, —$CH_2$—NH), 37.95 (s, $CH_2$—C'$O^4$), 55.53 (s, —$CH_2$NCO), 107.78 (s, C≡C), 114.75 (s, C≡C), 120.88 (s, $C'_0{}^2H$), 121.30 (s, $C'_0{}^3H$), 121.39 (s, $C_0{}^2H$), 122.48 (s, $C_{Ar}$), 122.90 (s, $C_{Ar}$), 125.59 (s, $CH_{Ar}$), 127.27 (s, $CH_{Ar}$), 127.86 (s, $CH_{Ar}$), 128.33 (s, $CH_{Ar}$), 128.50 (s, $CH_{Ar}$), 128.60 (s, $C_0{}^3$), 128.66 (s, $CH_{Ar}$), 129.04 (s, $CH_{Ar}$), 129.35 (s, $CH_{Ar}$), 131.14 (s, $CH_{Ar}$), 131.24 (s, $CH_{Ar}$), 131.26 (s, $C_{Ar}$), 132.02 (s, $CH_{Ar}$), 138.03, 140.59, 140.62 (d, $^3J_{CP}$=9.3 Hz, C═N), 140.74 (d, $^3J_{CP}$=9.4 Hz, C═N), 140.71 (s, $C_{Ar}$), 140.77 (s, $C_{Ar}$), 147.98 (s, $C_{Ar}$), 148.54 (m, $C'_0{}^1$), 150.94 (s, $C_{Ar}$), 151.74 (d, $^2J_{CP}$=9.8 Hz, $C_0{}^1$), 151.89 (br d, $C_0{}^1$), 171.24 (s, CONH), 172.22 (s, CON).

Synthesis of Compound f

To a suspension of tyramine-derived aminobismethylene-phosphonate compound prepared according to Rolland et al. (2008), A European Journal, 14: 4836-4850, (680 mg, 1.78 mmol) in THE (15 mL) and $CS_2CO_3$ (1.15 g, 3.56 mmol), compound e (350 mg, 0.18 mmol) is added. After one night of stirring at room temperature, the insolubles are removed by centrifugation and the solvent is removed by reduced pressure. Dendrimer f is obtained in the form of a clear oil with a yield of 97%. The compound can be purified on a chromatographic column.

[Chem 12]

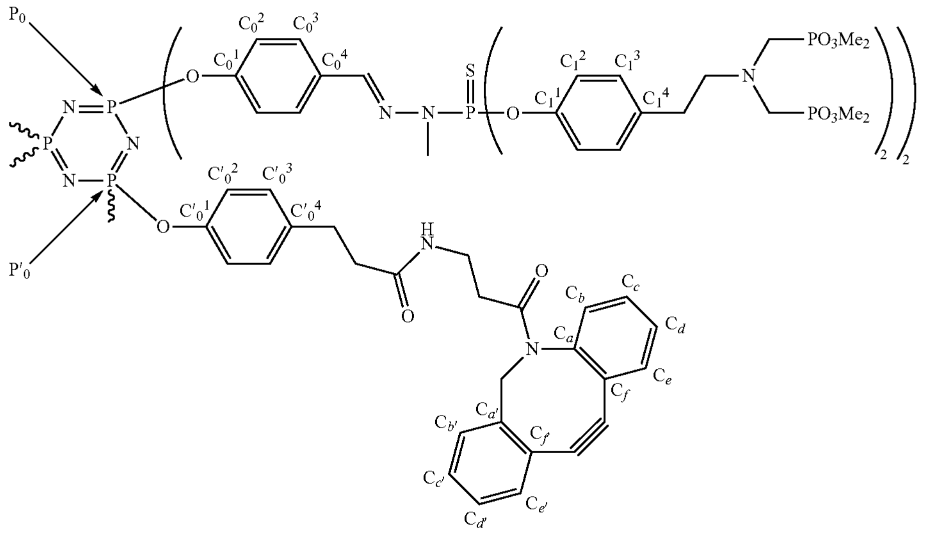

$^{31}$P NMR (243 MHz, Chloroform-d) δ: 8.33 (s, NP), 26.81 (s, POMe), 63.15 (s, PS), 6312 (s, PS), $^{1}$H NMR (600 MHz, Chloroform-d) δ: 1.86-1.90 (m, 1H, $CH_2CON$), 2.18 (t, $3J_{HH}$=7.8 Hz, 2H, $CH_2$—$C'_0{}^4$), 2.37-2.41 (m, 1H, $CH_2CON$), 2.74 (t, $3J_{HH}$=7.6 Hz, 20H, $C_1{}^4$—$CH_2$), 3.03 (t, $3J_{HH}$=7.6 Hz, 20H, $CH_2$—N), 3.17 (d, $^2J_{HP}$=9.5 Hz, 40H, $CH_2$—PO), 3.25 (d, $^3J_{HH}$=10.3 Hz, 4H, $CH_3$—N—), 3.25 (d, $^3J_{HH}$=10.0 Hz, 6H, $CH_3$—N), 3.30 (d, $^3J_{HH}$=10.0 Hz, 5H, $CH_3$—N), 3.71 (d, $^3J_{HH}$=10.4 Hz, 120H, POMe), 5.08 (d, $^2J_{HH}$=14 Hz, 1H, $CH_2$—$C_a'$), 6.24 (t, $^3J_{HH}$=6.1 Hz, 1H, CONH), 6.91 (d, $^3J_{HH}$=8.4 Hz, 2H, $C'_0{}^2H$), 6.96 (d, $^3J_{HH}$=8.6 Hz, 1H, $C'_0{}^3H$), 7.00 (d, $^3J_{HH}$=8.2 Hz, 5H, $C_0{}^2H$), 7.04 (d, $^3J_{HH}$=8.4 Hz, 3H, $C_0{}^2H$), 7.10-7.08 (m, 20H, $C_1{}^2H$), 7.15 (d, $^3J_{HH}$=7.9 Hz, 20H, $C1^3H$), 7.24 (m, 2H, $CH_{Ar}$), 7.35-7.31 (M, 2H, $CH_{Ar}$), 7.60 (d, $^3J_{HH}$=8.9 Hz, 10H, $C_0{}^3H$), 7.63 (d, $^3J_{HH}$=9.0 Hz, 15H, $C_0{}^3H$, CH═N).

$^{13}$C NMR (151 MHz, Chloroform-d) δ:31.91 (s, $CH_2$), 32.92 (d, $^2J_{Cp}$=5.9 Hz, $CH_3$—NPS), 33.01 (br s, $C_1{}^4$—$CH_2$, $CH_3$—NPS), 34.71 (s, $CH_2CON$), 35.25 (s, $CH_2$—NH), 37.74 (s, $CH_2$—$C'_0{}^4$), 49.44 (d, $^1J_{CP}$=157.5 Hz, $CH_2$—PO), 49.49 (d, $^1J_{CP}$=157.6 Hz, —$CH_2$—PO), 51.15-53.51 (m, POMe), 55.42 (s, $CH_2NCO$), 58.12 (t, $^3J_{CP}$=7.6 Hz, $CH_2$—N), 107.84 (s, C≡C), 114.71 (s, C≡C), 120.81 (s, $C'_0{}^2$), 121.24-121.18 (m, $C_1{}^2$, $C_0{}^2$), 122.36 (s, $CH_{Ar}$), 122.93 (s, $CH_{Ar}$), 125.50 (s, $CH_{Ar}$), 127.17 (s, $CH_{Ar}$), 127.80 (s, $CH_{Ar}$), 128.25-128.22 (m, $C_0{}^3$), 128.37 (s, $CH_{Ar}$), 128.64 (s, $CH_{Ar}$), 129.02 (s, $CH_{Adibo}$), 129.35 (s, $C'_0{}^3$), 129.91 (s, $C_1{}^3$), 132.14-132.07 (m, $C_0{}^4$), 136.54 (s, $C_1{}^4$), 136.58 (s, $C_1{}^4$), 138.01 (S, $C_{Ar}$), 138.72 (d, $^3J_{CP}$=13.8 Hz, C═N), 148.00 (s, $C_{Ar}$), 148.64 (s, $C_{Ar}$), 148.93 (s, $C_1{}^1$), 148.98 (s, $C_1{}^1$), 151.00 (s, $C_{Ar}$), 151.25 (br s, $C_0{}^1$), 171.52 (s, CONH), 171.90 (s, CON).

Synthesis of the NIR Compound

This compound is prepared according to the following diagram by adapting the procedure described in S. A. Klymchenko; V. G. Pivovarenko; O. Turan; D. P. Alexander New Journal of Chemistry, 27(9), 1336-1343; 2003.

Synthesis diagram [Diagram 2]

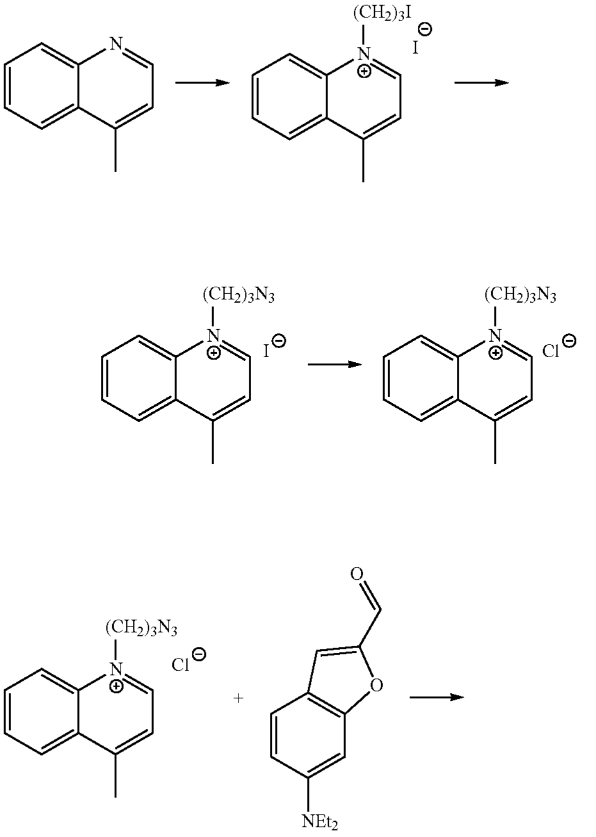

-continued

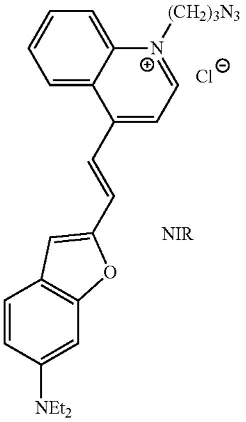

NIR

Synthesis of 1-(3-azidopropyl)-4-methylquinolinium chloride

To a solution of 1-(3-azidopropyl)-4-methylquinolinium iodide (1 g, 2.8 mmol) in $H_2O$/MeCN (50/50), a basic resin (DOWEX MARATHON MSA) (3 g) is added. The reaction mixture is stirred for 3 days at room temperature. The mixture is then filtered and concentrated to dryness under reduced pressure. The residue is solubilized in DCM (100 mL), then washed 2 times with $H_2O$ (30 mL). The organic phase is recovered, dried with $Na_2SO_4$, filtered and concentrated under reduced pressure. The crude residue is quickly purified on a silica column (eluent: DCM/MeOH, 90/10) to give a black solid with a yield of 70%.

[Chem 13]

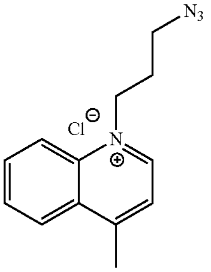

$^1$H NMR (300 MHz, Chloroform-d) δ: 2.71-2.33 (m, 2H, $CH_2$), 3.05 (s, 3H, Me), 3.82 (t, $^3J_{HH}$=6.5 Hz, 2H, $CH_2$—N3), 5.65-5.39 (m, 2H, $CH_2$—N), 8.08-7.98 (m, 2H, $CH_{Ar}$), 8.20-8.3 (m, 1H, $CH_{Ar}$), 8.40 (d, $^3J_{HH}$=8.5 Hz, 1H, $CH_{Ar}$), 8.56 (d, $^3J_{HH}$=9.0 Hz, 1H, $CH_{Ar}$), 10.25 (d, $^3J_{HH}$=6.0 Hz, 1H, $CH_{Ar}$).

$^{13}$C NMR (75 MHz, Chloroform-d) δ: 20.70 (s, Me), 29.45 (s, $CH_2$), 48.35 (s, $CH_2$), 54.99 (s, $CH_2$—N), 119.10 (s, $CH_{Ar}$), 123.32 (s, $CH_{Ar}$), 126.94 (s, $CH_{Ar}$), 129.51 (s, $C_{Ar}$), 130.13 (s, $CH_{Ar}$), 135.86 (s, $CH_{Ar}$), 137.14 (s, $C_{Ar}$), 148.79 (s, $C_{Ar}$), 158.56 (s, $CH_{Ar}$).

Synthesis of the NIR compound (E)-1-(3-azidopropyl)-4-(2-(6-(diethylamino)benzofuran-2-yl)vinyl) quinolinium chloride To a gold solution of 1-(3-azidopropyl)-4-methylquinolinium (500 mg, 1.9 mmol) in EtOH (30 mL) 6-Diethylaminobenzo[b]furan-2-carbaldehyde (1.2 g, 7.5 mmol) and a catalytic amount of piperidine (3 to 4 drops) are added, the solution is stirred under reflux for 5 hours. The mixture is evaporated to dryness under reduced pressure. The residue is purified by silica gel chromatography (eluent: DCM/MeOH 90/10) to give NIR in the form of a powder with a yield of 65%.

[Chem 14]

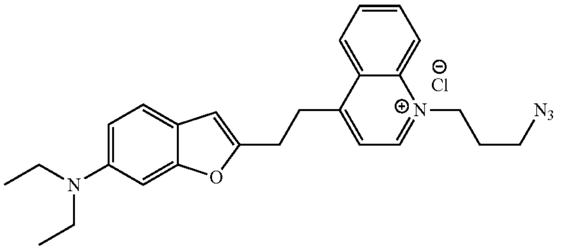

$^{35}$Cl NMR (59 MHz, Methylene Chloride-d2) δ: 233.98 (s, $Cl^-$).

$^1$H NMR (300 MHz, Methylene Chloride-d2) δ:1.25 (t, $^3J_{HH}$=7.1 Hz, 6H, $CH_3$—$CH_2$—N), 2.46-2.23 (m, 2H, $CH_2$—$CH_2$—N=), 3.46 (q, $^3J_{HH}$=7.1 Hz, 4H, $CH_3$—$CH_2$—N), 3.70 (t, $^3J_{HH}$=6.3 Hz, 2H, $CH_2$—N3), 5.17-4.99 (m, 2H, $CH_2$—N=), 6.62-6.56 (m, 1H, $CH_{Ar}$), 6.69 (d, $^3J_{HH}$=8.9 Hz, 1H, $CH_{Ar}$), 7.15 (s, 1H, CHfuran), 7.37 (d, $^3J_{HH}$=8.9 Hz, 1H, $CH_{Ar}$), 7.56 (d, $^3J_{HH}$=14.9 Hz, 1H, CHC=C), 7.83 (d, $^3J_{HH}$=8.4 Hz, 1H, $CH_{Ar}$), 7.90 (d, $^3J_{HH}$=15.2 Hz, 1H, CHe=c), 8.09-8.00 (m, 1H, $CH_{Ar}$), 8.19 (d, $^3J_{HH}$=8.9 Hz, 1H, $CH_{Ar}$), 8.23 (d, $^3J_{HH}$=6.7 Hz, 1H, $CH_{Ar}$), 8.46 (d, $^3J_{HH}$=8.6 Hz, 1H, $CH_{Ar}$), 9.48 (d, $^3J_{HH}$=6.6 Hz, 1H, $CH_{Ar}$).

$^{13}$C NMR (75 MHz, Methylene Chloride-d2) δ:12.46 (s, $CH_3$—$CH_2$—N), 29.02 (s, $CH_2$—$CH_2$—$N_3$), 45.08 (s, $CH_3$—$CH_2$—N), 48.40 (s, $CH_2$—N3), 54.09 (s, $CH_2$—N=), 91.85 (s, $CH_{Ar}$), 110.75 (s, $CH_{Ar}$), 114.00 (s, $CH_{Ar}$), 115.00 (s, $CH_{Ar}$), 117.06 (s, $CH_{Ar}$), 118.09 (s, $C_{Ar}$), 118.23 (s, $CH_{Ar}$), 123.05 (s, $CH_{Ar}$), 125.73 (s, $CH_{Ar}$), 126.39 (s, $C_{Ar}$), 128.71 (s, $CH_{Ar}$), 130.00 (s, $CH_{Ar}$), 134.92 (s, $CH_{Ar}$), 137.89 (s, $C_{Ar}$), 146.12 (s, $CH_{Ar}$), 149.31 (s, $C_{Ar}$), 151.11 (s, $C_{Ar}$), 152.20 (s, $C_{Ar}$), 159.46 (s, $C_{Ar}$).

Synthesis of Compound g

To a solution of dendrimer f (300, 0.055 mmol) in anhydrous acetonitrile (3 mL), the NIR fluorescent azide (25.5 mg, 0.11 mmol) is added. The reaction mixture is stirred for three days at room temperature. The solvent is then removed under reduced pressure to give the dendrimer g with a quantitative yield in the form of a blue oil.

[Chem 15]

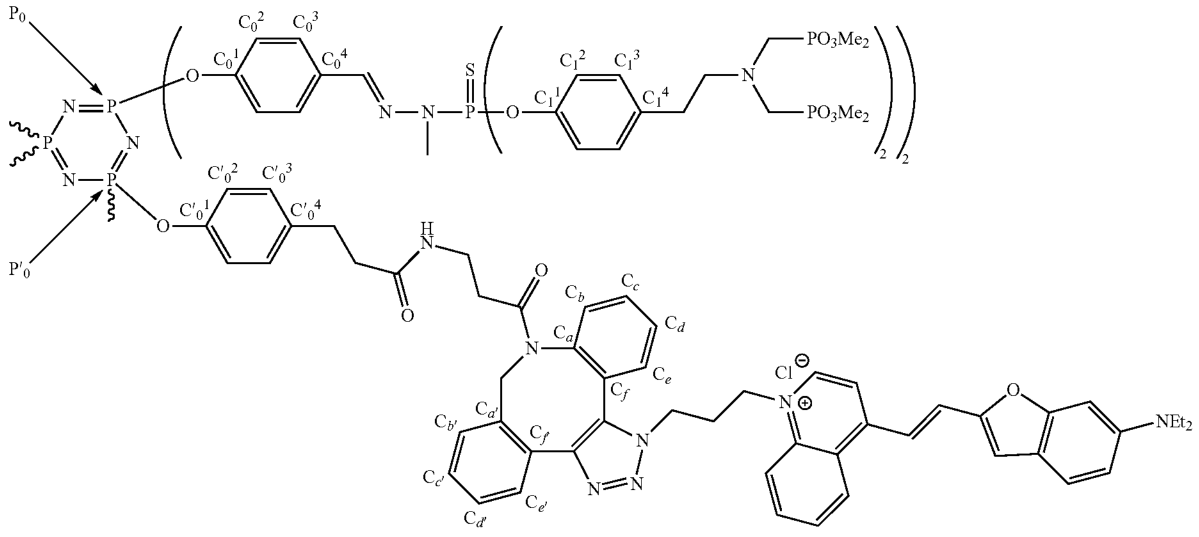

$^{31}P$ NMR (121 MHz, $CD_2Cl_2$) δ: 8.40 (s, $N_3P_3$), 29.64 (s, —$PO_3Me_2$), 63.26 (s, —P═S—).

$^1H$ NMR (500 MHz, $CD_2Cl_2$) δ: 1.19 (t, $^3J_{HH}$=7.1 HZ, 6H, $CH_3$—$CH_2$—N), 2.63-2.19 (m, 4H, $CH_2$), 2.74 (br s, 22H, $C_1^4$—$CH_2$, $CH_2$), 3.04 (br s, 20H, $C_1^4$—$CH_2$—CH—), 3.17 (d, $^2J_{HP}$=9.4 Hz, 41H, —$CH_2$—P, $CH_2$), 3.39-3.26 (m, 17H, $CH_3$—N, $CH_2$), 3.60-3.45 (m, 4H, Me-$CH_2$—N), 3.64-3.57 (m, 120H, $POCH_3$), 7.10-6.73 (m, 16H, $C_0^3$H, $C_0$'$^2$H, $C_0^3$H, $CH_{Ar}$), 7.13 (d, $^3J_{HH}$=7.2 Hz, 24H, $C_1^2$H, $H_{Ar}$), 7.21 (d, $^3J_{HH}$=7.3 Hz, 22H, $C_{13}$H, $H_{Ar}$), 7.37-7.25 (m, 4H, $H_{Ar}$), 7.58-7.38 (m, 4H, $H_{Ar}$), 8.10-7.57 (m, 19H, CH═N, $C_0^3$H, $H_{Ar}$).

$^{13}C$ NMR (126 MHz, $CD_2C_{12}$) b: 29.66 (s, $CH_3$), 32.76 (s, $CH_2$), 32.88 (s, $CH_3$), 45.08 (s, $CH_2$), 49.34 (d, $^1J_{CP}$=157.4 Hz, N—$CH_2$—P), 49.40 (d, $J_{CP}$=157.4 Hz, N—$CH_2$—P), 52.49 (br s, $POCH_3$), 58.07 (s, $CH_2$), 58.12 (s, $CH_2$), 58.17 (S, $CH_2$), 120.89 (s, $CH_{Ar}$), 121.13 (S, $C_1^2$), 128.21 (s, $C_0^3$), 129.38 (S, $CH_{Ar}$), 129.93 (S, $C_1^3$), 132.29 (brs, $C_0^4$), 136.98 ($C_1^4$), 138.98 (s, CH═N—), 148.94 (br s, $C1^1$), 148.98 (br s, $C1^1$), 151.25 (br s, $C0^1$).

Synthesis of Compound G1-A-NIR

To a solution of dendrimer g (300, 0.05 mmol) in anhydrous $CH_3CN$ (30 mL) at 0° C., BrTMS (0.33 mL, 2.55 mmol) is added drop by drop. After one night of stirring, the mixture is evaporated to dryness under reduced pressure. The crude residue is taken up in 10 mL of MeOH. After one hour of stirring at room temperature, the solid is recovered by filtration then washed twice with MeOH (20 mL) and with $Et_2O$ (20 mL). The resulting solid is dried under reduced pressure to give the G1-A-NIR dendrimer in the form of a green powder with a quantitative yield. The compound is then converted to sodium salt to be analyzed. To a stirred suspension of phosphonic acid compound in water are added 20 equivalents of a 0.1 M aqueous NaOH solution. The resulting solution is microfiltered at 0.4 μM then freeze-dried to give the expected compound in the form of a blue powder with a yield of 85%.

[Chem 16]
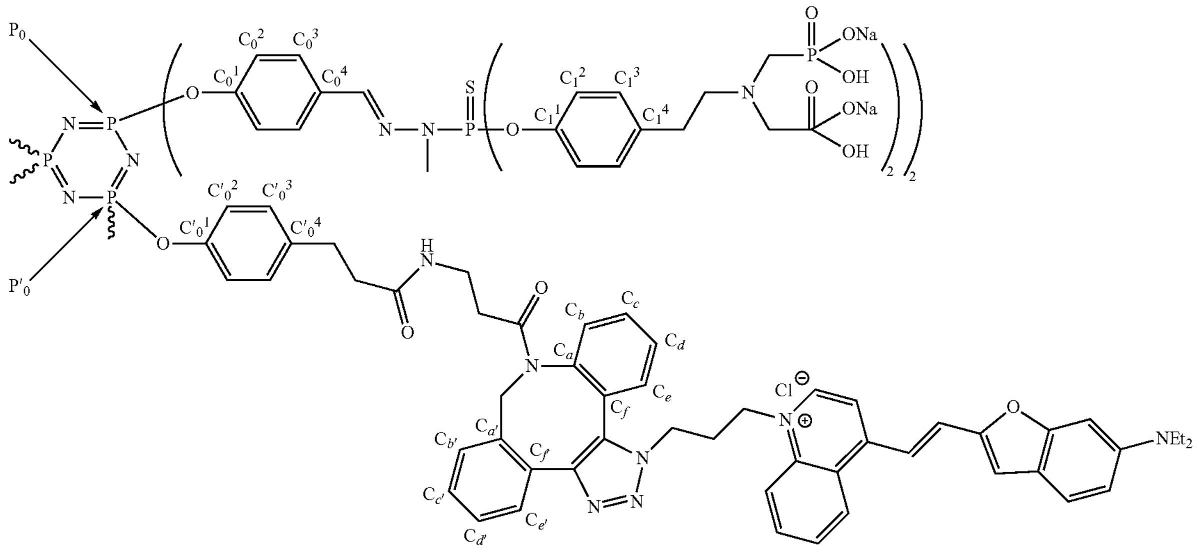
$^{31}P$ NMR (121 MHz, Deuterium Oxide) b: 6.78 (s, POHONa), 6.83 (s, POHONa), 9.26 (s, P=N), 64.09 (s, PS), 64.35 (s, PS).
Dendrimer G1-B
[Chem 17]
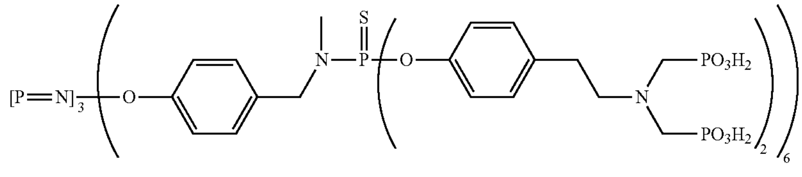
The G1-B dendrimer is synthesized according to the reaction scheme shown in diagram 3:
[Diagram 3]
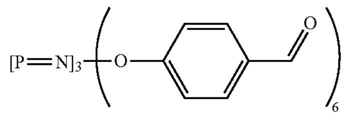
1-G'0
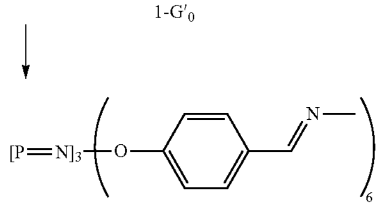
1-G"0

-continued

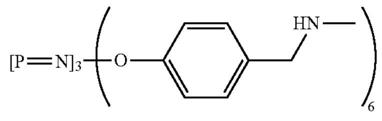

1-G'''$_0$

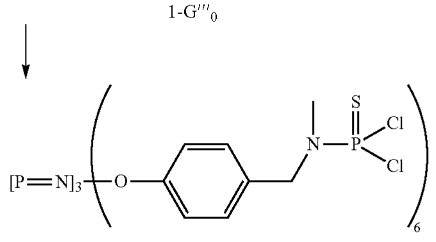

1-G$_1$

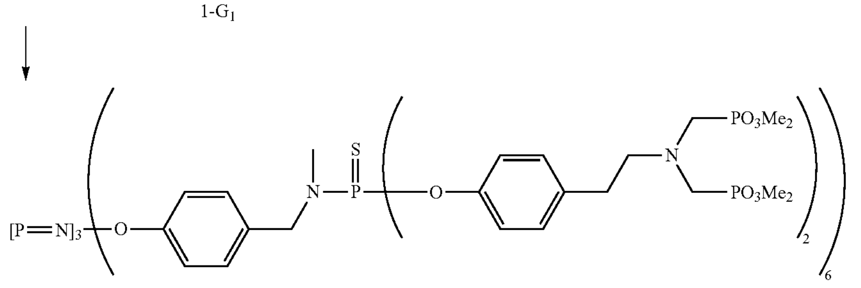

3-G'$_1$

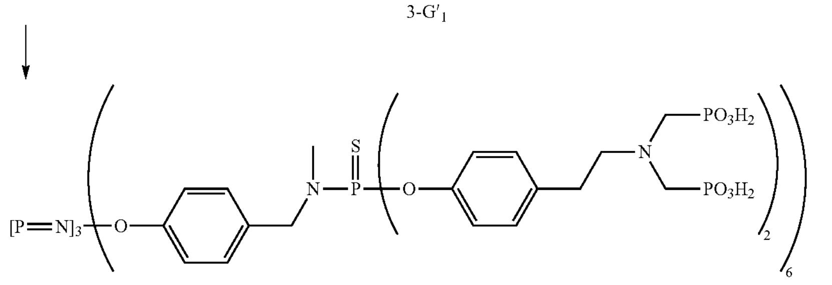

G1-B

Synthesis of Compound 1-G'$_0$

[Chem 18]

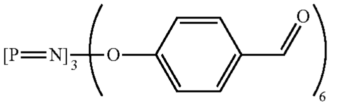

To a solution of $N_3P_3Cl_6$ (2000 mg, 5.75 mmol) in THF (200 mL) at room temperature, $K_2CO_3$ (14.3 g, 103.5 mmol) and 4-hydroxybenzaldehyde (4634 mg, 37.95 mmol) are successively added. After 72 h under agitation at room temperature, the mixture is filtered then concentrated to dryness. The crude residue is washed 4 to 5 times with MeOH to give compound 1-G'$_0$ in the form of a white powder with a yield of 81%.

$^1$H NMR (300 MHz, Chloroform-d): δ (ppm) 9.83 (s, 6H, CHO), 7.74 (d, $^3J_{HH}$=8.6 Hz, 12H, $C_0{}^3$H), 7.12 (d, $^3J_{HH}$=8.5 Hz, 12H, $C_0{}^2$H).

$^{31}$P NMR (121 MHz, Chloroform-d): δ (ppm) 7.15 (s, $P_0$).

$^{13}$C NMR (75 MHz, Chloroform-d): δ (ppm) 190.47 (s, CHO), 154.44 (dd, $^2J_{CP}$=5.1 Hz, $^4J_{CP}$=2.5 Hz, $C_0{}^1$), 133.74 (s, $C_0{}^4$), 131.38 (s, $C_0{}^3$), 121.21 (d, $^4J_{CP}$=2.5 Hz, $C_0{}^2$).

Synthesis of Compound 1-G"$_0$

[Chem 19]

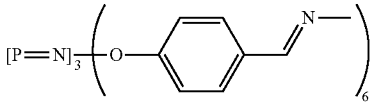

To a solution of compound 1-G'$_0$ (500 mg, 0.580 mmol) in THF (50 mL) at room temperature, a solution of 8M methylamine in EtOH (1.3 mL, 10.45 mmol) is added. After one night of stirring at room temperature, the mixture is concentrated to dryness to give the dendrimer 1-G"$_0$ in the form of a white powder.

$^1$H NMR (300 MHz, Acetonitrile-d$_3$): δ (ppm) 8.24 (d, $^4J_{HH}$=1.7 Hz, 6H, CH═N), 7.55 (d, $^3J_{HH}$=8.6 Hz, 12H, $C_0{}^3$H), 6.99 (d, $^3J_{HH}$=8.5 Hz, 12H, $C_0{}^2$H), 3.50 (s, 18H, N—$CH_3$)

$^{31}$P NMR (121 MHz, Acetonitrile-d$_3$): δ (ppm) 8.66 (s, $P_0$).

$^{13}$C NMR (75 MHz, Acetonitrile-d$_3$): δ (ppm) 160.80 (s, C═N), 151.57 (dd, $^2J_{CP}$=5.1 Hz, $^4J_{CP}$=2.5 Hz, $C_0{}^1$), 133.94 (s, $C_0{}^4$) 129.13 ($C_0{}^3$), 120.66 (dd, $^3J_{CP}$=3.2 Hz, $^5J_{CP}$=1.8 Hz, $C_0{}^2$), 47.29 (s, $CH_3$).

Synthesis of Compound 1-G'''$_0$-HCI

[Chem 20]

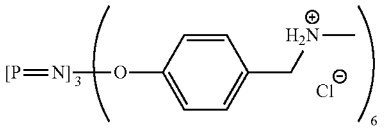

To a solution of dendrimer 1-G''$_0$ (500 mg, 0.53 mmol) in a THF/MeOH (25/5) mL mixture $NaBH_4$ (201 mg, 5.32 mmol) is added. After one night under stirring at room temperature, the mixture is concentrated to dryness. The crude residue is diluted in 200 mL of DCM and then washed once with 50 mL of distilled water. The organic phase is recovered, dried with $Na_2SO_4$, filtered and concentrated under reduced pressure. The product is then dissolved in MeOH (30 mL) to which 9.5 mL of HCl (1 M in MeOH) is added. After 2 h under stirring at room temperature, the solution is filtered and concentrated under reduced pressure. The residue is then washed 3 times with 25 mL of $CH_2Cl_2$ to give the product 1-G'''$_0$-HCI (protonated form HCl) in the form of a white powder.

$^1$H NMR (400 MHz, Methanol-d$_4$): δ (ppm) 7.54 (d, $^3J_{HH}$=8.5 Hz, 12H, $C_0{}^3$H), 7.05 (d, $^3J_{HH}$=8.3 Hz, 12H, $C_0{}^2$H), 4.27 (s, 12H, $CH_2$NH), 2.75 (s, 18H, N—$CH_3$).

$^{31}$P NMR (162 MHz, Methanol-d$_4$): δ (ppm) 8.29 (s, $P_0$).

13C NMR (101 MHz, Methanol-d4): δ (ppm) 151.07 (dd, $^2J_{CP}$=5.1 Hz, 4$J_{CP}$=2.5 Hz, $C_0{}^1$), 131.46 (s, $C_0$3), 128.71 (s, $C_0{}^4$), 121.12 (dd, $^3$J=3.2, $^5$J=1.7 Hz, (s, $C_0{}^2$), 51.30 (s, $CH_2$NH), 31.88 (s, N—$CH_3$).

Synthesis of Compound 1-G'''$_0$

[Chem 21]

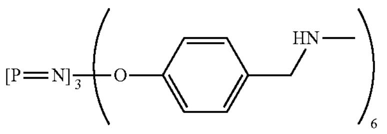

The compound 1-G'''$_0$-HCI (300 mg) is solubilized in 25 mL of distilled water to which 25 mL of a NaOH (2M) solution is added. The aqueous phase is then extracted 3 times with 200 mL of $CH_2Cl_2$. The organic phase is then dried with $Na_2SO_4$ filtered and concentrated under vacuum to give the dendrimer 1-G'''$_0$ in the form of a clear oil with a yield of 80%.

$^1$H NMR (400 MHz, Chloroform-d): δ (ppm) 7.12 (d, $^3J_{HH}$=8.5 Hz, 12H, $C_0{}^3$H), 6.91 (d, $^3J_{HH}$=8.3 Hz, 12H, $C_0{}^2$H), 3.69 (s, 12H, $CH_2$NH), 2.43 (s, 18H, N—$CH_3$).

$^{31}$P NMR (162 MHz, Chloroform-d): δ (ppm) 8.71 (s, $P_0$).

$^{13}$C NMR (101 MHz, Chloroform-d): δ (ppm) 149.55 (dd, $^2J_{CP}$=5.1 Hz, $^4J_{CP}$=2.5 Hz, $C_0{}^1$), 136.70 (s, $C_0{}^3$), 128.99 (s, $C_0{}^4$), 120.82 (dd, $^3$J=3.4, $^5$J=1.7 Hz, $C_0{}^2$), 55.43 (s, $CH_2$NH), 36.06 (s, N—$CH_3$).

Synthesis of Compound 1-G1

[Chem 22]

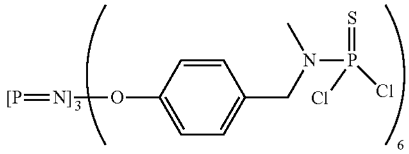

To a solution of $PSCl_3$ (3.109 mL, 30.60 mmol) in $CH_2Cl_2$ (100 mL) at room temperature, a solution of dendrimer 1-G'''$_0$ (800 mg, 0.85 mmol) is added drop by drop in the presence of $Et_3N$ (0.740 mL, 5.31 mmol) in $CH_2Cl_2$ (25 mL) over a period of 30 min. After 3 h of stirring at room temperature, the mixture is concentrated to dryness under reduced pressure. The crude residue is then solubilized in 200 mL of $CH_2Cl_2$ then filtered over a silica gel to give dendrimer 1-G1 in the form of a clear oil with a yield of 82%.

$^1$H NMR (300 MHz, Chloroform-d): δ (ppm) 7.22 (d, $^3J_{HH}$=8.5 Hz, 12H, $C_0{}^3$H), 6.99 (d, $^3J_{HH}$=8.3 Hz, 12H, $C_0{}^2$H), 4.60 (d, $^3J_{HP}$=15.1 Hz, 12H, $CH_2$NH), 2.82 (d, $^3J_{HP}$=16.2 Hz, 18H, N—$CH_3$).

$^{31}$P NMR (121 MHz, Chloroform-d): δ (ppm) 64.12 (s, $P_1$), 8.35 (s, $P_0$).

$^{13}$C NMR (75 MHz, Chloroform-d): δ (ppm) 150.26 (dd, $^2J_{CP}$=5.1 Hz, $^4J_{CP}$=2.5 Hz, $C_0{}^1$), 132.73 (d, $^3J_{CP}$=6.5 Hz, $C_0{}^4$), 129.17 (s, $C_0{}^3$), 121.29-121.15 (m, $C_0{}^2$), 54.18 (d, $^2J_{CP}$=5.5 Hz, $CH_2$NH), 35.11 (d, $^2J_{CP}$=2.5 Hz, N—$CH_3$).

Compound 3-G'$_1$(OMe)

[Chem 23]

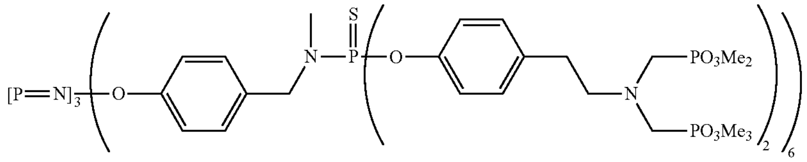

To a solution of compound 1-G1 prepared previously (1 mmol) in THE (30 mL) with $Cs_2CO_3$ (24 mmol), phenol aza-bis-dimethyl-phosphonate is added (see WO 2005/052031 A1) (12 mmol). After one night of stirring at room temperature, the mixture is centrifuged, filtered, then concentrated under reduced pressure. The crude residue is diluted in a minimum of THE then washed with a large volume of diethyl ether. After drying under reduced pressure, the dendrimer 3-G'$_1$(OMe) is obtained in the form of a clear oil with a quantitative yield.

$^{31}$P—{$^1$H}(243 MHz, $CDCl_3$) NMR δ=8.40 (s, N=P), 26.85 (s, PO), 68.32 (s, PS);

$^1H$ NMR (600 MHz, $CDCl_3$) δ=2.75 (d, $^3J_{HH}$=10.1 Hz, 24H, $C_1{}^4$—$CH_2$), 2.77 (d, $^3J_{HP}$=7.6 Hz, 18H, $CH_3$), 3.06 (d, $^3J_{HH}$=7.7 Hz, 24H, $C_1{}^4$—$CH_2$—$CH_2$). 3.19 (d, $^2J_{HP}$=9.4 Hz, 48H, $CH_2$—P), 3.73 (d, $^3J_{HP}$=10.6 Hz, 144H, POMe), 6.94 (d, $^3J_{HH}$=8.2 Hz, 12H, $C_0{}^2$H), 7.07 (d, $^3J_{HH}$=8.1 Hz, 24H, $C_{12}$H), 7.18 (br d, $^3J_{HH}$=8.2 Hz, 36H, $C_0{}^3$ and C1$^3$H);

$^{13}C$-{$^1H$}NMR (151 MHz, $CDCl_3$) δ=33.05 (s, $CH_2$), 33.64 s, ($CH_3N$), 49.46 (dd, $^1$Jcp=157.3, $^3$Jcp=7.2 Hz, $CH_2$—P), 53.56-51.75 (m, $POCH_3$), 53.47 (d, $^2$Jcp=10.3 Hz, $C_1{}^4$—$CH_2$). 58.22 (t, $^3$Jcp=7.7 Hz, $C_1{}^4$—$CH_2$—$CH_2$). 120.91 (br d, $^3$Jcp=4.4 Hz, $C_0{}^2$ and $C_1{}^2$), 129.30 (s, $C_0$3), 129.87 (s, $C_{13}$), 134.10 (br d, $^2$Jcp=4.5 Hz, $C_0{}^4$), 136.22 (s, $C_{14}$), 149.35 (d, $^2$Jcp=7.5 Hz, $C_1{}^1$), 150.01 (br s, $C_0{}^1$) ppm.

Compound G1-B

[Chem 24]

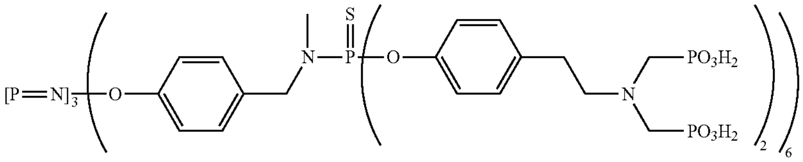

To a solution of dendrimer 3-Gi(OMe) (1 g, 0.17 mmol) in anhydrous $CH_3CN$ (30 mL) at 0° C., BrTMS (1.34, 10.2 mmol) is added drop by drop. After one night of stirring, the mixture is concentrated to dryness under reduced pressure. The residue is stirred for one hour in MeOH (10 mL), then washed twice with MeOH (20 mL then once with $Et_2O$ (20 mL). The solid obtained is dried under reduced pressure to give the G1-B dendrimer in the form of a white powder with a quantitative yield.

Compound G1-B is not sufficiently soluble in water to be analyzed by NMR, it is converted to sodium monosalt according to the following procedure:

To a stirred suspension of G1-B in water are added 24 equivalents of a 0.1 M aqueous NaOH solution. The resulting solution is microfiltered to 0.4 μM then freeze-dried to give the salt form of G1-B (24 sodium atoms) in the form of a white powder with a yield of 90%.

$^{31}P$—{$^1H$}(162 MHz, $D_2O/CD_3CN$) NMR δ=6.93 (s, PO), 9.59 (s, N=P), 68.77 (s, PS);

$^1H$ NMR (600 MHz, $D_2O/CD_3CN$) δ=2.76 (d, $^3J_{HH}$=10.7 Hz, 18H, $CH_3$), 3.13 (t, $^3J_{HH}$=8.8 Hz, 24H, $C_1{}^4$—$CH_2$), 3.47 (d, $^2J_{HH}$=11.9 Hz, 48H, $CH_2$—P), 3.72 (t, $^3J_{HH}$=8.6 Hz, 24H, $C_1{}^4$—$CH_2$—$CH_2$). 4.47 (d, $^2J_{HH}$=13.5 Hz, 12H, $C_0{}^4$—$CH_2$), 6.91 (d, $^2J_{HH}$=8.1 Hz, 12H, $C_0{}^2$H), 7.15 (d, $^2J_{HH}$=8.1 Hz, 24H, $C_1{}^2$H), 7.29 (d, $^2J_{HH}$=8.3 Hz, 12H, $C_0{}^3$H), 7.38 (d, $^2J_{HH}$=8.2 Hz, 24H, C1$^3$H);

$^{13}C$-{$^1H$}NMR (151 MHz, $D_2O/CD_3CN$) δ=29.07 (s, $C_1{}^4$—$CH_2$). 33.58 (s, $CH_3$), 52.91 (d, $^1J_{CP}$=127.6 Hz, $CH_2$—P), 52.94 (s, $C_0{}^4$—$CH_2$). 57.81 (s, $C_1{}^4$—$CH_2$—$CH_2$). 121.14 (br s, $C_0{}^2$), 121.42 (d, $^3J_{CP}$=4.4 Hz $C_1{}^2$), 129.61 (s, $C_0{}^3$), 130.59 (s, $C_{13}$), 133.95 (s, $C_{14}$), 134.89 (s, $C_0{}^4$), 149.18 (s, $C_0{}^1$), 149.60 (d, $^3J_{CP}$=7.6 Hz, $C_1{}^1$) ppm.

Dendrimer G1-B-NIR

Synthesis diagram: [Diagram 4]
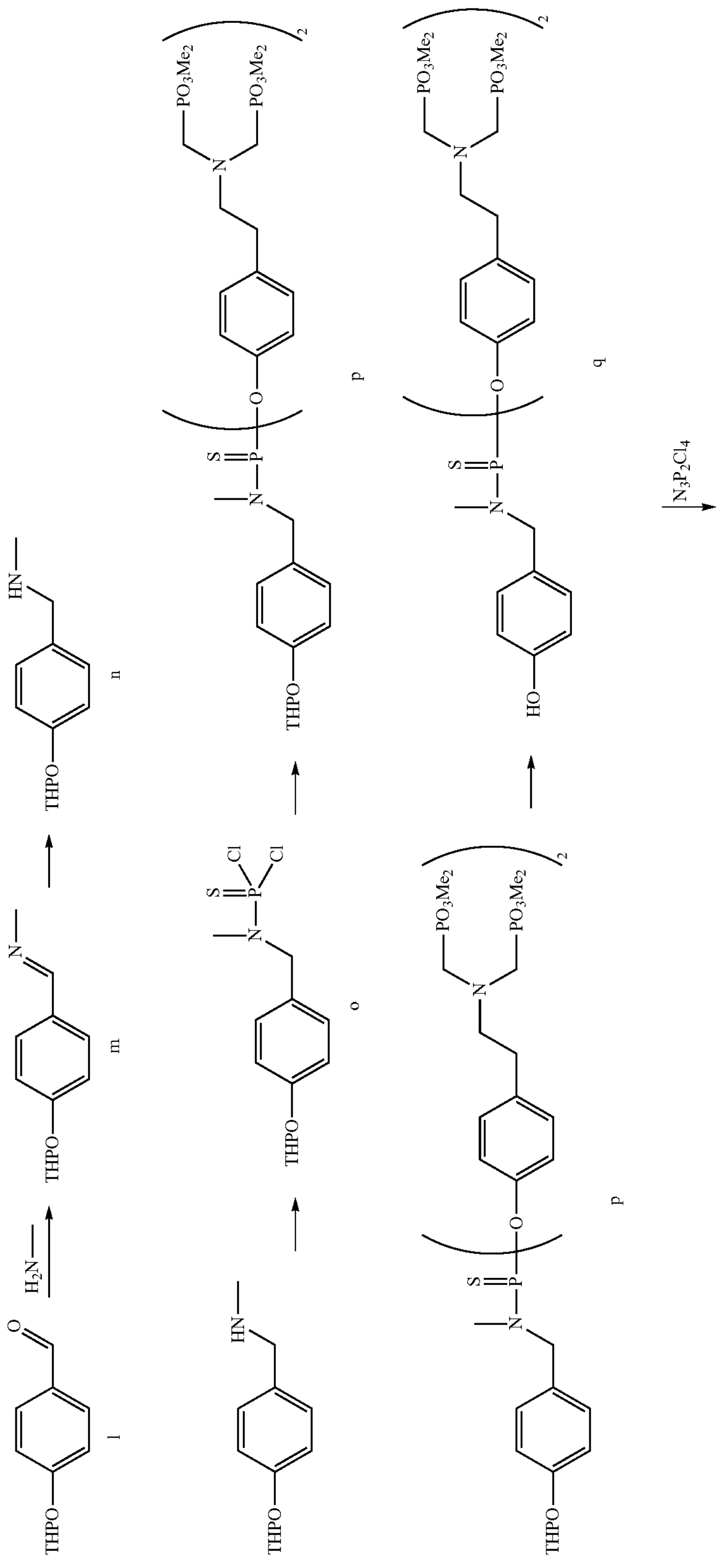

-continued
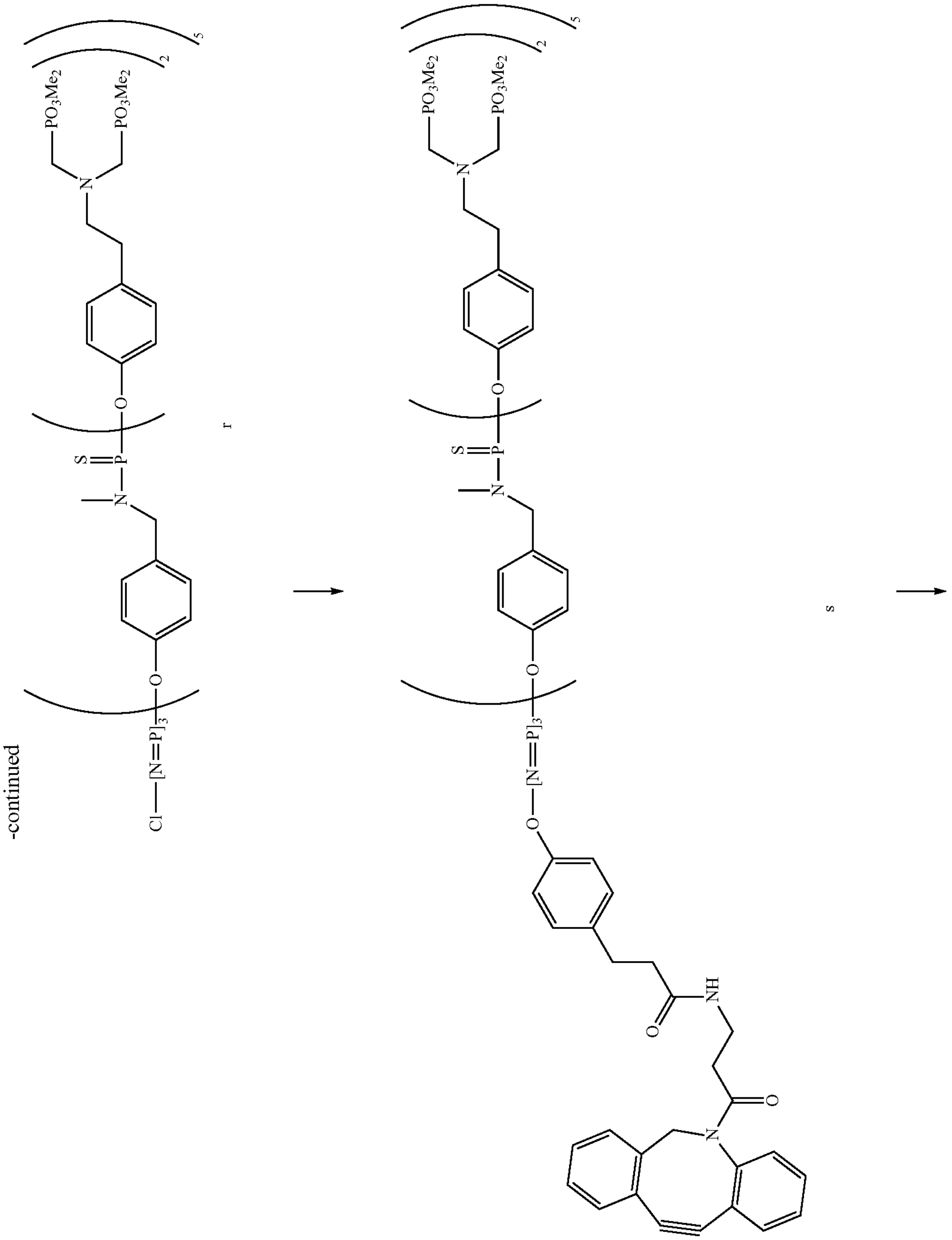

-continued
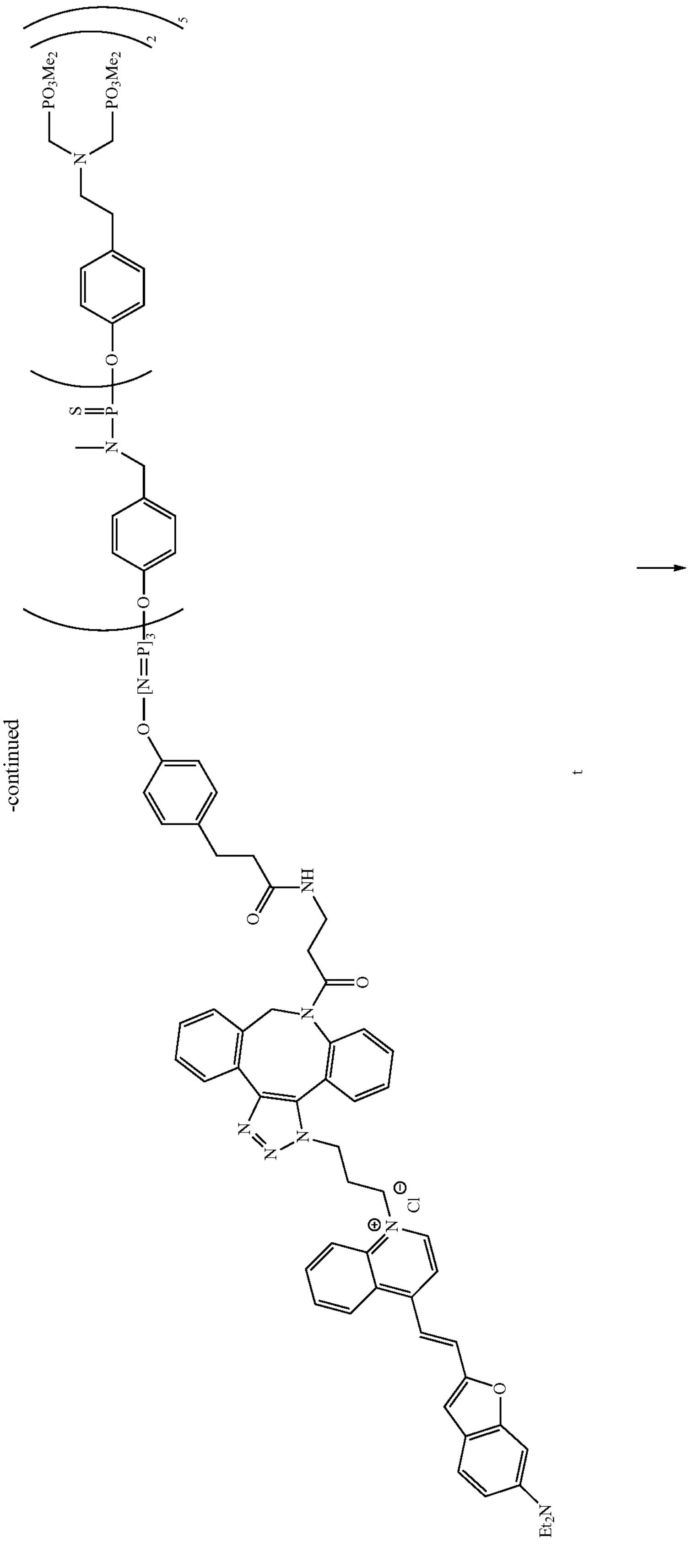

-continued
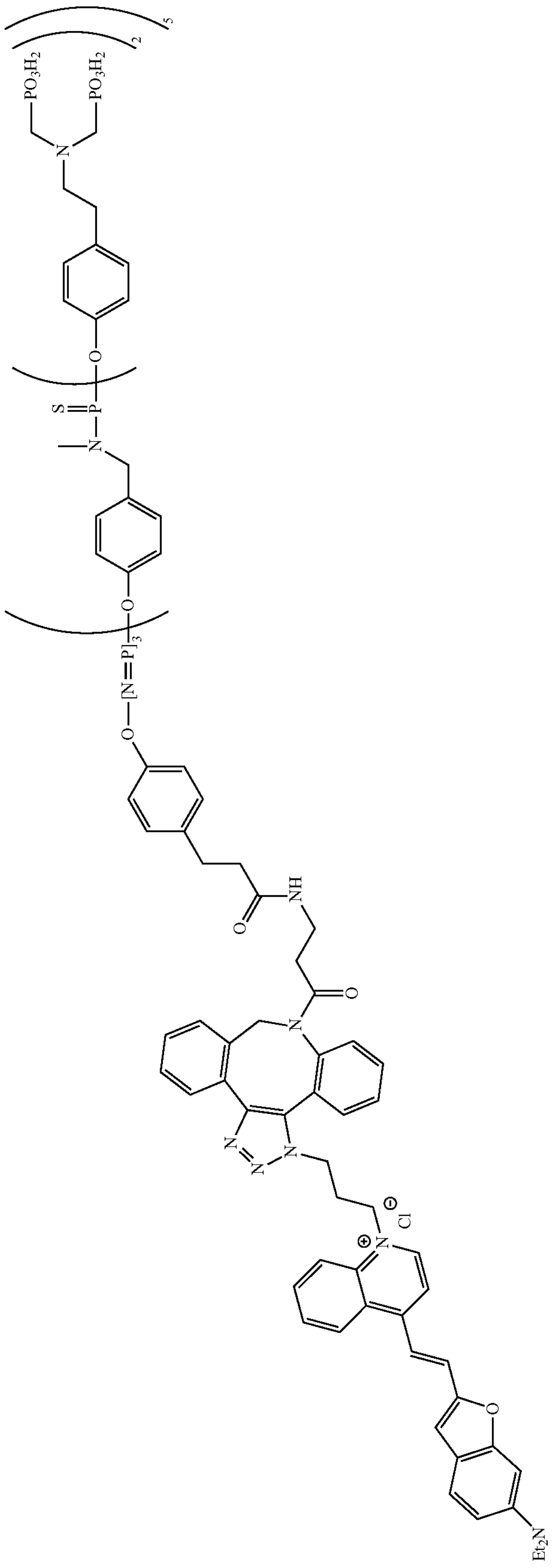

Compound m

[Chem 25]

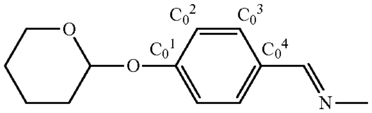

To a solution of 4-((tetrahydro-2H-pyran-2-yl)oxy)benzaldehyde (Fu H. et al. Molecules, 2014, 16:17715-17726) (1 g, 4.83 mmol) in THE (30 mL) a solution of methylamine (8M in EtOH) (1.8 mL, 14.49 mmol) is added. After one night of stirring at room temperature, the mixture is concentrated to dryness to give product m in the form of a colorless oil with a 95% yield.

$^1$H NMR (300 MHz, Methanol-$d_4$) δ (ppm): 1.39-1.74 (m, 3H, —$CH_2$—), 1.75-1.92 (m, 2H, —$CH_2$—), 1.90-2.06 (m, 1H, —$CH_2$-0), 3.55-3.62 (m, 1H, —$CH_2$—O), 3.79-3.87 (m, 1H, —$CH_2$—), 5.46 (t, $^3J_{HH}$=3.1 Hz, 1H, O—CH—O), 7.08 (d, $^3J_{HH}$=8.8 Hz, 2H, $C_0$2H), 7.63 (d, $^3J_{HH}$=8.8 Hz, 2H, $C_0^3$H), 8.21 (q, $^4J_{HH}$=1.6 Hz, 1H, —CH═N—).

$^{13}$C NMR (75 MHz, Methanol-$d_4$) δ (ppm): 18.46 (s, —$CH_2$—), 24.89 (s, —$CH_2$—), 29.95 (s, —$CH_2$—), 46.32 (s, $CH_3$—), 61.73 (s, —$CH_2$—O), 96.10 (s, —CH—O), 116.17 (s, $C_0^2$), 129.22 (s, $C_0^4$), 129.30 (s, $C_0$3), 159.41 (s, $C_0^4$), 163.46 (s, C═N).

Compound n

[Chem 26]

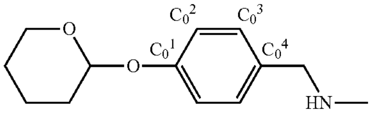

To a solution of compound m (1 g, 4.5 mmol), 10% Pd/C (225 mg) and MeOH (40 mL) are introduced into a Fisher Porter type tube. The tube is slowly placed under vacuum so that the air is expelled. The $H_2$ pressure is then adjusted to 5 bar. The reaction mixture is stirred for 2 days at room temperature. After a slow depressurization, the reaction mixture is recovered, filtered and concentrated under reduced pressure. The residue is purified by silica gel chromatography (eluent: AcOEt) to obtain compound n in the form of a clear oil with a yield of 80%.

$^1$H NMR (300 MHz, Chloroform-d) δ (ppm): 1.33-1.72 (m, 3H, —$CH_2$—), 1.77-1.82 (m, 2H, —$CH_2$—), 1.87-2.07 (m, 1H, —$CH_2$-0), 2.36 (s, 3H, $CH_3$), 3.50-3.57 (m, 1H, —$CH_2$-0), 3.61 (s, 2H, —$CH_2$—N), 3.76-3.99 (m, 1H, —$CH_2$—), 5.34 (t, $^3J_{HH}$=3.3 Hz, 1H, O—CH—O), 6.96 (d, $^3J_{HH}$=8.6 Hz, 2H, $C_0^2$H), 7.09-7.26 (m, 2H, $C_0^2$H).

$^{13}$C NMR (75 MHz, Chloroform-d) δ (ppm): 18.78 (s, —$CH_2$—), 25.16 (s, —$CH_2$—), 30.33 (s, —$CH_2$—), 35.63 (s, —$CH_3$), 55.31 (s, —$CH_2$—N), 61.96 (s, —$CH_2$—O), 96.38 (s, O—CH—O), 116.36 (s, $C_0^2$), 129.25 (s, $C_0$3), 132.78 (s, $C_0$3), 156.12 (s, $C_0^4$).

Compound o

[Chem 27]

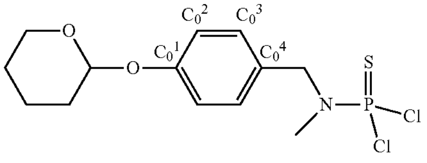

To a solution of $PSCl_3$ (2.2 mL, 22.6 mmol) in DCM (100 mL) a solution of compound n (1 g, 4.52 mmol) is added drop by drop in the presence of $Et_3N$ (0.62 mL, 4.52 mmol) in DCM (40 mL) over a period of 30 min. After 4 hours of stirring at room temperature, the reaction mixture is concentrated to dryness under reduced pressure. The crude residue is then solubilized in 200 mL of DCM then filtered over a silica gel to give dendron o in the form of a clear oil with a yield of 85%.

$^{31}$P NMR (162 MHz, Chloroform-d) δ (ppm): 63.18 (s, PS).

Compound p

[Chem 28]

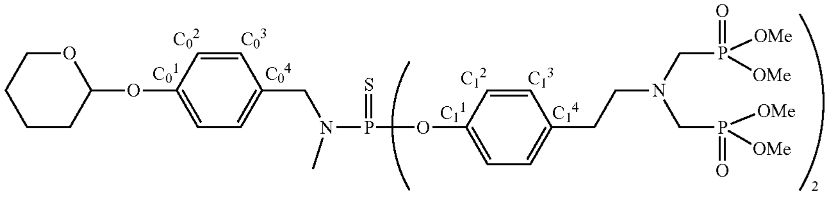

To a solution of compound o (1 mmol) in THE (30 mL) with $Cs_2CO_3$ (4 mmol) the phenol aminobismethylene phosphonate derived from tyramine (Rolland et al. (2008), A European Journal, 14: 4836-4850) (2 mmol) is added. After one night of stirring at room temperature, the mixture is centrifuged, filtered then concentrated under reduced pressure. The crude residue is then purified by chromatographic column on silica gel with eluent mixture (MeOH/EtOAc) to give, after removal of solvents under reduced pressure, the compound p in the form of a clear oil with a yield of 85%.

$^{31}$P NMR (162 MHz, Chloroform-d) δ (ppm): 26.95 (s, POMe), 68.48 (s, P═N).

$^1$H NMR (400 MHz, Chloroform-d) δ (ppm): 1.58-1.72 (m, 3H, —$CH_2$), 1.81-1.94 (m, 2H, $CH_2$), 1.96-2.05 (m, 1H, $CH_2$), 2.78-2.83 (m, 7H, $C_1^4$—$CH_2$, $CH_3$N), 3.09 (t, $^3J_{HH}$=7.6 Hz, 4H, $CH_2N$), 3.22 (d, $^3J_{HH}$=8.9 Hz, 8H), 3.55-3.67 (m, 1H, $CH_2$—O), 3.75 (d, $^3J_{HP}$=10.3 Hz, 24H, POMe), 3.89-3.95 (m, 1H, $CH_2$—O), 4.44 (d, $^3J_{HP}$=12.0 Hz, 2H), 5.41 (t, $^3J_{HH}$=3.3 Hz, 1H, O—$CH_2$—O), 6.99 (d, $^3J_{HH}$=8.6 Hz, 2H, $C_0{}^2H$), 7.12 (d, $^3J_{HH}$=8.4, 4H, $C_{12}H$), 7.16-7.25 (m, 6H, $C_0{}^3H$, $C_13H$).

Compound q

[Chem 29]

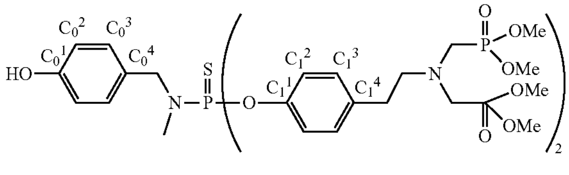

To a solution of compound p (1 mmol) in MeOH (30 mL), pyridinium p-toluenesulfonate (1.5 mmol) is added. The reaction mixture is stirred overnight at room temperature. The solvent is removed under reduced pressure and the residue is purified by silica gel chromatography (eluent: MeOH/AcOEt) to give after removal of the solvents under reduced pressure the compound q in the form of a clear oil with a yield of 80%.

$^{31}P$ NMR (162 MHz, Chloroform-d) δ (ppm): 26.76 (s, POMe), 68.38 (s, PS).

Compound r

To a suspension of dendron q (1 g, 1.04 mmol) in THE (30 mL) with $Cs_2CO_3$ (794 mg, 2.08 mmol), hexachlorocyclotriphosphazene (70 mg, 0.20 mmol) is added. After one night of stirring at room temperature, the reaction mixture is centrifuged, celite-filtered then concentrated under reduced pressure. Compound r is obtained in the form of a clear oil with a yield of 90%.

[Chem 30]

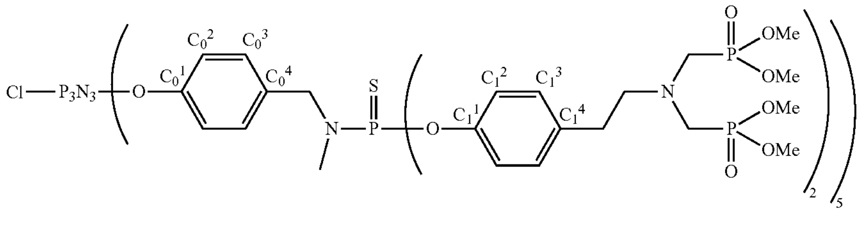

$^{31}P$ NMR (121 MHz, Chloroform-d) δ (ppm): 6.50 (d, $^2J_{PP}$=83.3 Hz, P=N), 21.50 (dd, $^2J_{PP}$=85.2, $^2J_{PP}$=81.6 Hz, P=N), 26.41 (s, POMe), 68.12 (s, PS).

Compound s

To a suspension of compound b (130 mg, 0.30 mmol) in THE (30 mL) with $Cs_2CO_3$ (199 mg, 0.61 mmol), compound r (989 mg, 0.2 mmol) is added. After one night of stirring at 45° C., the mixture is centrifuged, filtered then concentrated under reduced pressure. The residue is purified on a silica column with DCM/MeOH (60/40) to give the dendrimer t with a yield of 90%. The product can be purified by flash chromatography on silica column.

[Chem 31]

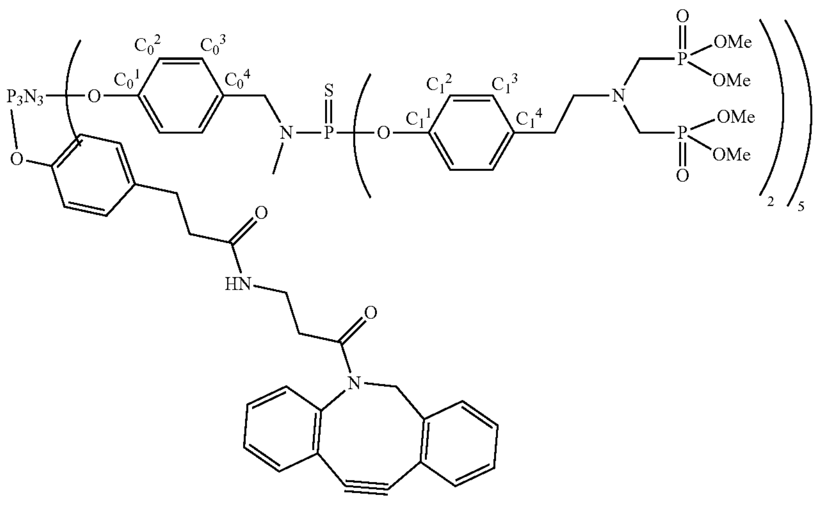

$^{31}P$ NMR (162 MHz, Chloroform-d) δ (ppm): 8.45 (s, P=N), 26.89 (s, POMe), 68.33 (s, PS).

Compound t

To a solution of dendrimer s (500, 0.093 mmol) in anhydrous acetonitrile (3 mL) the azide compound NIR (43.4 mg, 0.18 mmol) is added.

The reaction mixture is stirred for three days at room temperature. The solvent is then removed under reduced pressure to give the dendrimer t with a quantitative yield in the form of a blue oil.

[Chem 32]

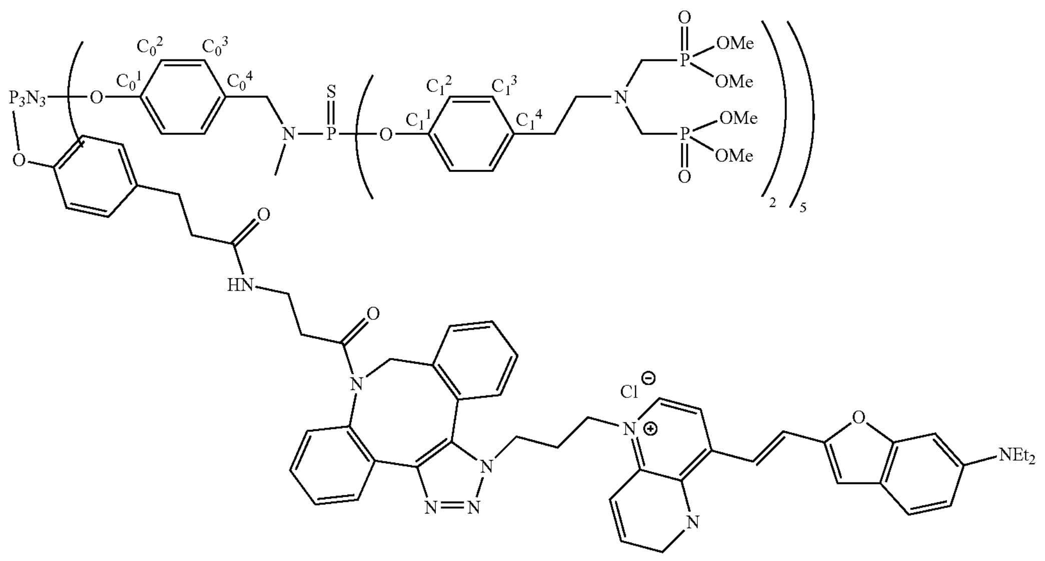

$^{31}P$ NMR (162 MHz, Chloroform-d) δ (ppm): 8.40 (s, P=N), 26.86 (s, POMe), 68.38 (s, PS).

G1B-NIR

To a solution of dendrimer t (500, 0.086 mmol) in anhydrous $CH_3CN$ (50 mL) kept at 0° C., BrTMS (0.56 mL, 4.38 mmol) is added drop by drop. After one night of stirring, the mixture is concentrated to dryness under reduced pressure. The crude residue is taken up in 10 mL of MeOH. After one hour of stirring at room temperature, the solid is recovered by filtration then washed twice with MeOH (20 mL) and with Et2O (20 mL). The resulting solid is then dried under reduced pressure to give the G1B-NIR dendrimer in the form of a green powder with a quantitative yield.

[Chem 33]

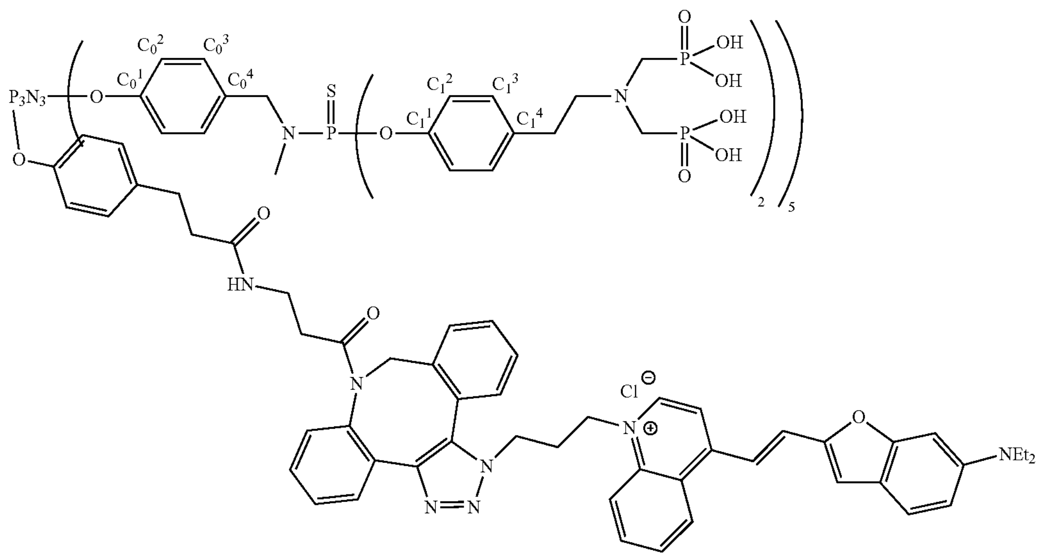

The compound is then converted to sodium salt to be analyzed. To a stirred suspension of phosphonic acid compound in water are added 20 equivalents of a 0.1 M aqueous NaOH solution. The resulting solution is microfiltered at 0.4 μM then freeze-dried to give the expected compound in the form of a blue powder with a yield of 85%.

[Chem 34]

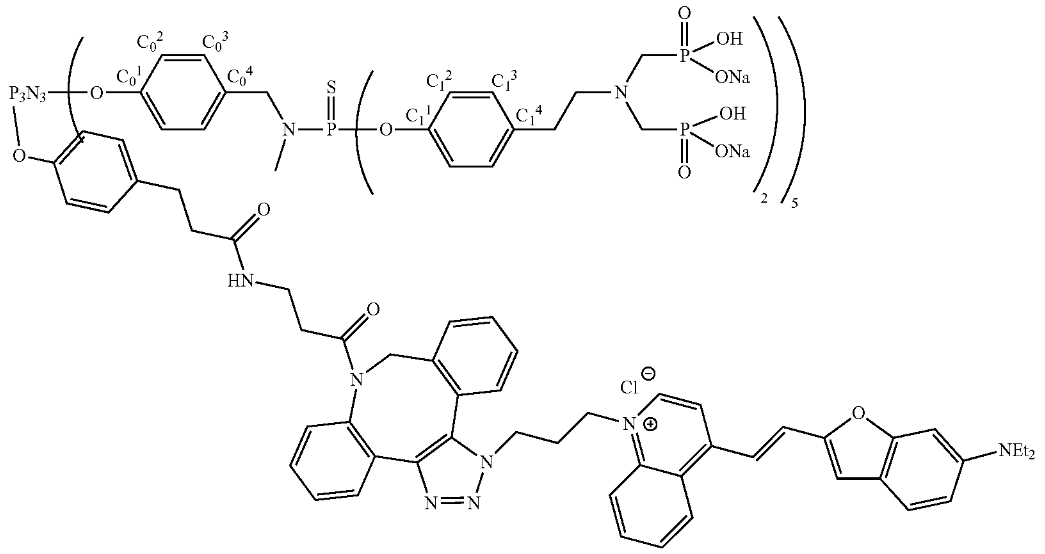

$^{31}P$ NMR (162 MHz, Deuterium Oxide) δ (ppm): 6.66 (s, $PO_3HNa$), 6.69 (s $PO_3HNa$), 6.74 (s, $PO_3HNa$), 9.42 (s, P=N), 68.49 (s, PS), 68.69 (s, PS).

Dendrimer G1-C

[Chem 35]

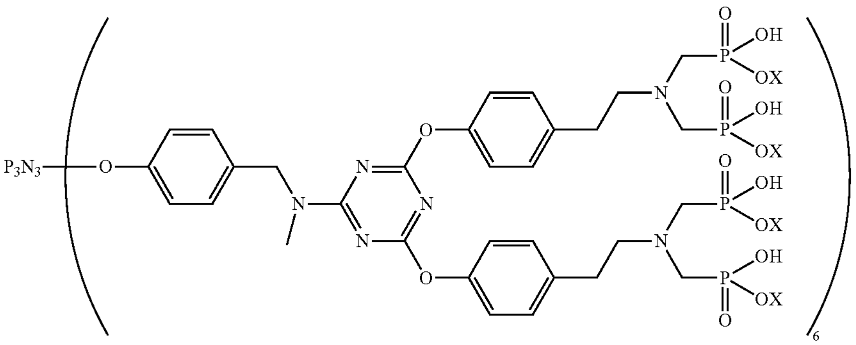

X = H or Na

Compound u

[Chem 36]

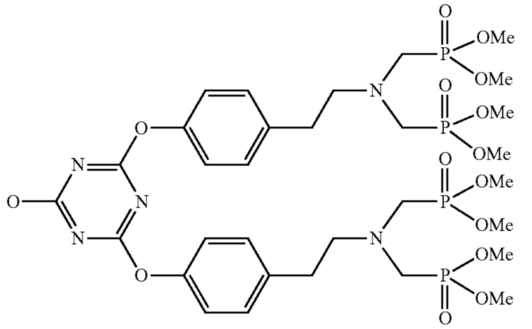

Compound v

[Chem 37]

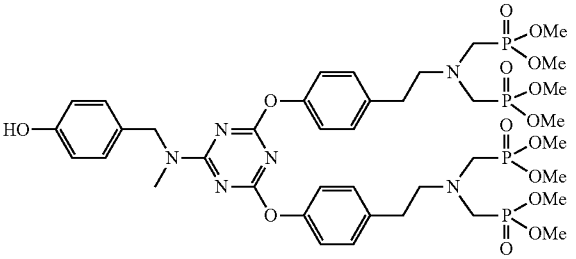

To a solution of cyanuric chloride (1 g, 5.4 mmol) in dichloromethane (60 mL) at 0° C., phenol aminobismethylenephosphonate derived from tyramine (see WO 2005/052031 A1) (2.1 g, 5.4 mmol) and N, N diisopropylethylamine (296 mg, 5.7 mmol) are added. After one hour of stirring at 0° C., a further addition of phenol aminobismethylenephosphonate derived from tyramine (2.1 g, 5.4 mmol) and N, N diisopropylethylamine (696 mg, 5.4 mmol) are made at 0° C. The reaction mixture is then left under stirring at room temperature for one night. After filtration and removal of the solvents under reduced pressure, the residue is purified by silica gel chromatography (eluent: DCM/MeOH; 98/02) to give compound u in the form of a yellow oil with a yield of 80%.

$^{31}P$—{$^{1}H$}NMR (121 MHz, Chloroform-d) δ (ppm): 26.55 (s, POMe).

$^{1}H$ NMR (300 MHz, Chloroform-d) δ (ppm): 2.72 (t, J=7.3 Hz, 4H), 3.02 (t, J=7.4 Hz, 4H), 3.10 (d, J=9.4 Hz, 8H), 3.62 (d, J=10.5 Hz, 24H), 6.96 (d, J=8.5 Hz, 4H), 7.20 (d, J=8.6 Hz, 4H).

$^{13}C$-{$^{1}H$}NMR (75 MHz, Chloroform-d) δ (ppm): 32.94 ($CH_2$), 49.39 (dd, J=157.9 Hz, J=7.5 Hz, $CH_2$), 51.65-53.36 (m, $CH_3$), 57.81 (t, J=7.7 Hz, $CH_2$), 120.83 (CH), 130.07 (CH), 137.69 (C), 149.54 (C), 172.39 (C), 173.36 (C).

To a solution of compound u (2 g, 2.28 mmol) in THE (40 mL), p-hydroxy-N-methylbenzylamine (324 mg, 4.56 mmol) and N, N-diisopropylethylamine (794 mg, 6.84 mmol) are added at room temperature. The reaction mixture is then stirred at 60° C. overnight. After filtration and removal of solvents under reduced pressure, the crude residue is purified by silica gel chromatography (eluent: DCM/MeOH; 95/05) to give compound v in the form of a clear oil with a 70% yield.

$^{31}P$—{$^{1}H$}NMR (121 MHz, Chloroform-d) δ (ppm): 26.73 (s, POMe), 26.94 (s, POMe).

$^{1}H$ NMR (300 MHz, Chloroform-d) δ (ppm): 2.84-2.79 (m, 4H), 3.02-3.15 (m, 4H, $CH_2$, 3H $CH_3$), 3.21 (d, $^{2}J_{HH}$=9.1 Hz, 8H, $CH_2$), 3.79-3.72 (m, 24H, $CH_3$), 4.33 (s, 2H, $CH_2$), 6.70 (br d, $^{4}H$, $CH_2$), 7.02 (d, $^{3}J_{HH}$=8.5 Hz, 2H, $CH_2$), 7.09 (d, $^{3}J_{HH}$=8.5 Hz, 2H, $CH_2$), 7.19-7.28 (m, 4H, $CH_2$).

$^{13}C$-{$^{1}H$}NMR (75 MHz, Chloroform-d) δ (ppm): 32.82 (s, $CH^2$), 33.17 (s, $CH^2$), 35.34 (s, $CH^3$), 47.15-51.27 (m, $CH^2$), 52.74-52.64 (m, $CH^3$), 57.14-58.97 (m, $CH^2$), 115.45 (s, CH), 121.59 (s, CH), 121.96 (s, CH), 127.41 (s, Cq), 129.47 (s, CH), 129.64 (s, CH), 136.12 (s, Cq), 136.37 (s, Cq), 150.49 (s, Cq), 150.99 (s, Cq), 156.65 (s, Cq), 167.11 (s, Cq), 172.21 (s, Cq), 172.29 (s, Cq).

Compound w

[Chem 38]

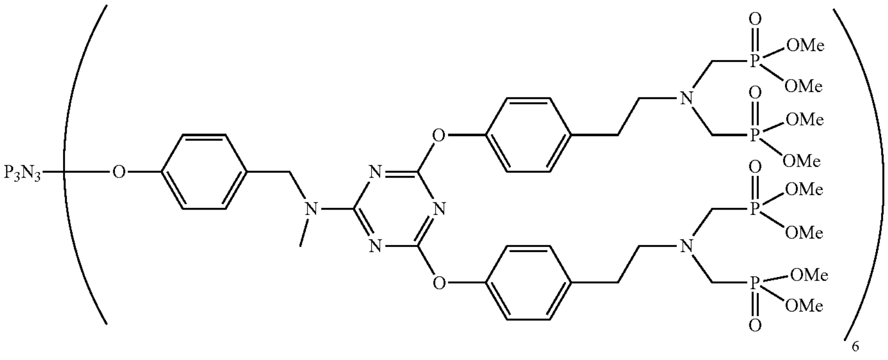

To a suspension of compound v (1.02 mmol) in THF (30 mL) with $CS_2CO_3$ (2.04 mmol), hexachlorocyclotrisphosphazene (0.14 mmol) at room temperature is added. After one night of stirring at 40° C., the mixture is centrifuged, filtered then concentrated under reduced pressure. Compound w is obtained in the form of a clear oil with a quantitative yield.

$^{31}P$—{$^1H$}NMR (121 MHz, Chloroform-d) δ (ppm): 8.11 (s, N=P), 27.06 (br s, POMe).

$^1H$ NMR (300 MHz, Chloroform-d) δ (ppm): 2.77 (m, 24H), 2.87-2.96 (m, 18H), 3.05 (t, J=8.3 Hz, 24H), 3.12-3.30 (m, 48H), 3.60-3.88 (m, 144H), 4.64 (s, 12H), 6.89 (d, J=8.6 Hz, 10H), 7.01 (m, 16H), 7.03-7.10 (m, 24H), 7.14-7.24 (m, 24H).

Compound G1-C

To a solution of compound w (1 g, 0.16 mmol) in anhydrous $CH_3CN$ (50 mL) at 0° C., bromotrimethylsilane (1.4 g, 9.6 mmol) is added drop by drop. After one night of stirring, the reaction mixture is concentrated to dryness under reduced pressure. The residue is stirred for one hour in MeOH (10 mL), then washed 3 times with MeOH (20 mL) then once with $Et_2O$ (20 mL). The resulting solid is dried under reduced pressure to give compound G1-C in phosphonic acid form (neutral) in the form of a white powder with a yield of 80%.

The compound is then converted to sodium salt to be analyzed. To a stirred suspension of phosphonic acid compound in water 24 equivalents of a 0.1 M aqueous NaOH solution are added. The resulting solution is microfiltered at 0.4 μM and then freeze-dried to give the expected compound in the form of a white powder with a yield of 90%.

$^{31}P$—{$^1H$}NMR (162 MHz, Deuterium Oxide) δ (ppm): 9.64 (s, N—P), 6.70 (br s, $PO_3HNa$).

$^1H$ NMR (400 MHz, Deuterium Oxide) δ (ppm): 2.96 (br s, 18H, $CH_3$), 3.20 (br s, 24H, $CH_2$), 3.37-3.41 (m, 48H), 3.79 (br s, 24H, $CH_2$), 6.72-6.98 (m, 10H, CH), 7.00-7.29 (m, 38H, CH), 7.36-7.65 (m, 24H, CH).

$^{13}C$-{1H}NMR (101 MHz, Deuterium Oxide) δ (ppm): 28.95 (s, $CH_3$), 53.42 (br s, $CH_2$), 54.66 (br s, $CH_2$), 57.35 ((br s, $CH_2$), 121.02 (s, CH), 121.76 (s, CH), 129.16 (s, $CH_2$), 130.46 (CH), 134.52 (s, C), 150.54 (s, C), 171.65 (br s, C═N).

Compound G1-C-NIR

[chem 39]

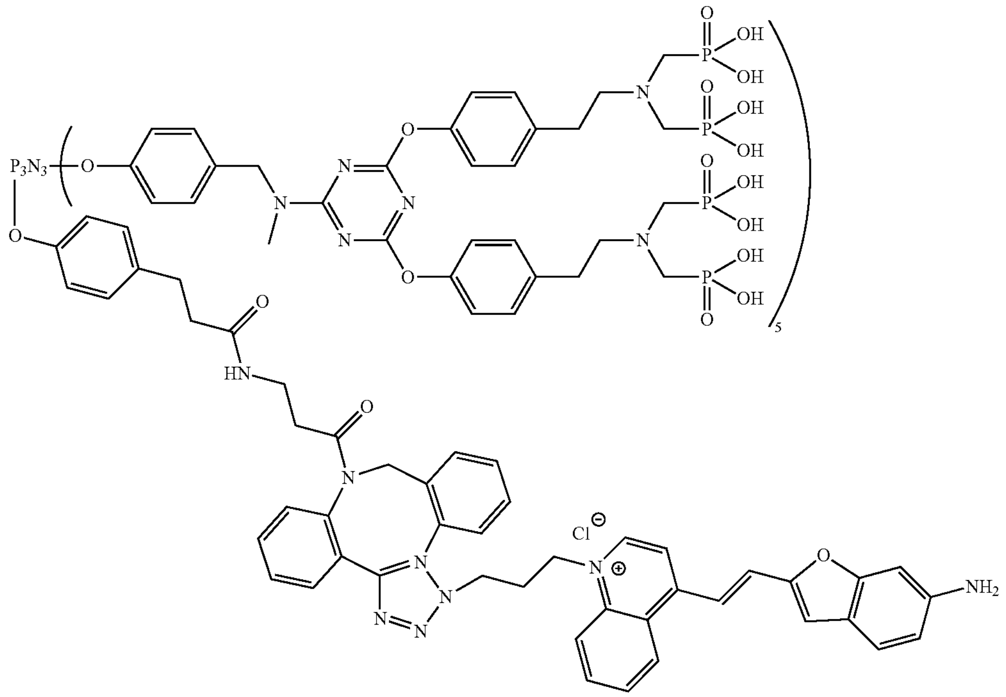

Compound x

[chem 40]

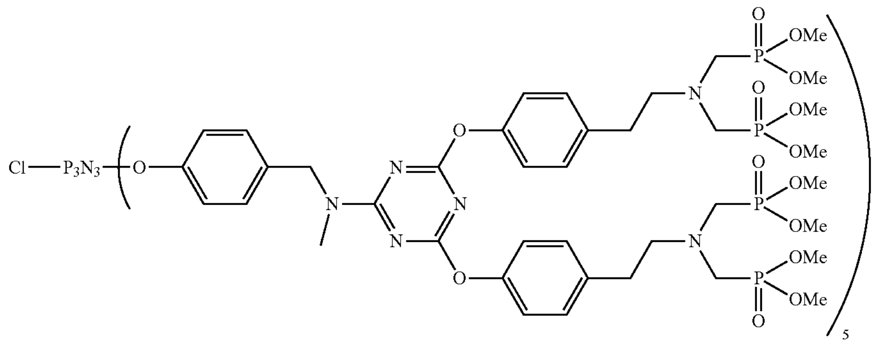

To a solution of compound v (0.9 g, 1.0 mmol) in THE (30 mL) with $CS_2CO_3$ (794 mg, 2.08 mmol), hexachlorocyclotrisphosphazen (70 mg, 0.20 mmol) is added. After one night of stirring at room temperature, the mixture is centrifuged, filtered then concentrated under reduced pressure. Compound x is obtained in the form of a clear oil with a yield of 90%.

$^{31}P$—{$^{1}H$}NMR (121 MHz, Chloroform-d) δ (ppm): 6.35 (d, $^{2}J_{PP}$=82.2 Hz, P=N), 20.76-20.98 (m, P=N)), 26.41 (s, POMe).

Compound y

[Chem 41]

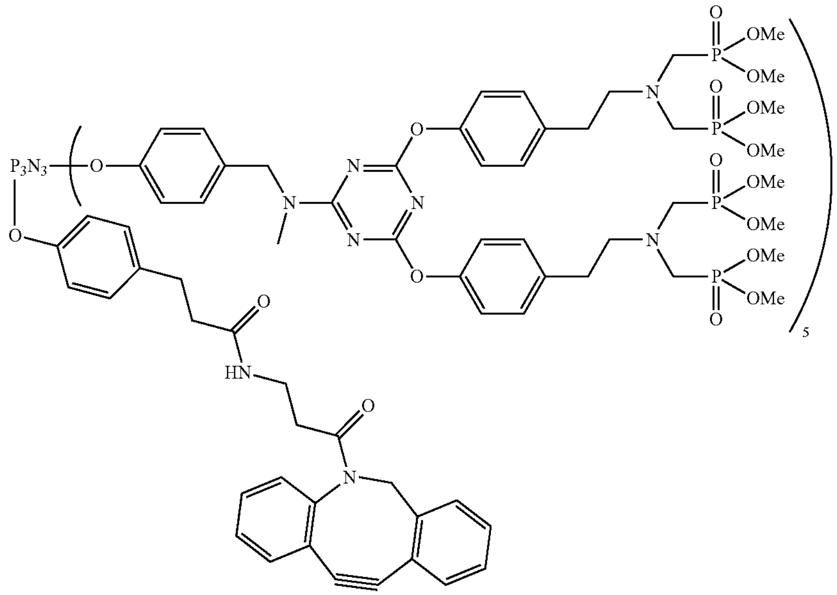

To a solution of compound b (75 mg, 0.17 mmol) in THF (30 mL) with $Cs_2CO_3$ (199 mg, 0.34 mmol), compound x (900 mg, 0.17 mmol) is added. After one night of stirring at 45° C., the mixture is centrifuged, filtered then concentrated under reduced pressure to give compound y with a quantitative yield.

$^{31}P$—{$^1H$}NMR (162 MHz, Chloroform-d) δ (ppm): 8.45 (s, P=N), 26.89 (br s, POMe).

Compound z

To a solution of compound y (500 mg, 0.092 mmol) in anhydrous acetonitrile (5 mL) compound NIR is added (as described in S. A. Klymchenko; V. G. Pivovarenko; O. Turan; D. P. Alexander New Journal of Chemistry, 27(9), 1336-1343; 2003) (43.4 mg, 0.18 mmol). The reaction mixture is stirred for three days at room temperature. The solvent is concentrated under reduced pressure to give the dendrimer z with a quantitative yield in the form of a blue oil.

[Chem 42]

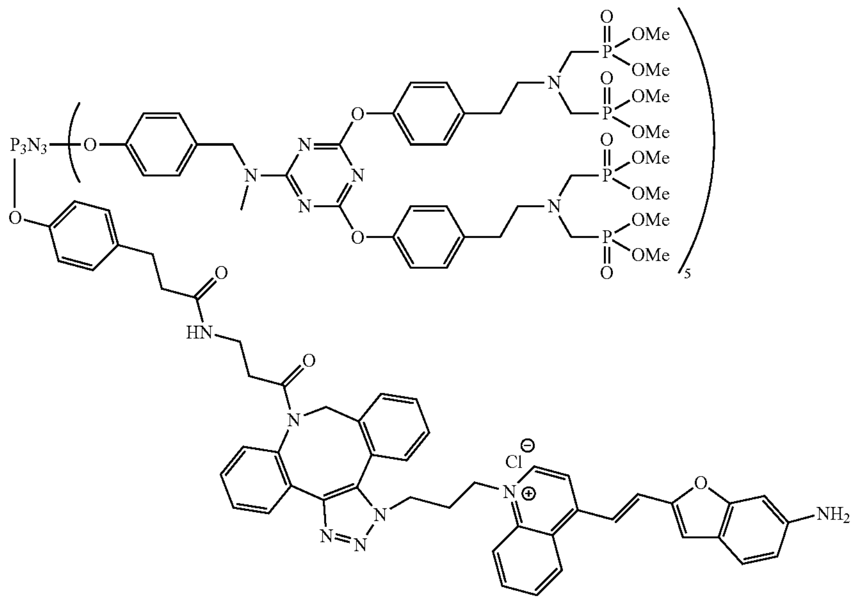

$^{31}P$—{$^{1}H$}NMR (162 MHz, Chloroform-d) δ (ppm): 8.51 (s, P=N), 26.72 (br s, POMe).

Compound G1-C-NIR

To a solution of dendrimer z (500, 0.086 mmol) in anhydrous $CH_3CN$ (50 mL) at 0° C., bromotrimethylsilane (0.56 mL, 4.38 mmol) is added drop by drop. After one night of stirring, the mixture is concentrated to dryness under reduced pressure. The residue is stirred for one hour in MeCOH (10 mL), then washed twice with MeCOH (20 mL) then once with $Et_2O$ (20 mL). The resulting solid is dried under reduced pressure to give the G1-C-NIR dendrimer in the form of a green powder with a quantitative yield. The compound is then converted to sodium salt to be analyzed.

To a stirred suspension of phosphonic acid compound in water 20 equivalents of a 0.1 M aqueous NaOH solution are added. The resulting solution is microfiltered at 0.4 μM then freeze-dried to give the expected compound in the form of a blue powder with a yield of 80%.

$^{31}P$—{$^{1}H$}NMR (162 MHz, Deuterium Oxide) δ (ppm): 7.79 (br s, $PO_3HNa$), 9.42 (s, P=N).

2. Preparing the Vesicles

The dendrimer formulation is obtained by mixing catanionic surfactant TriCat-n and acidic dendrimeric precursor G1-X in water [FIG. 1], The formula of TriCat12 is as follows:

[Chem 42]

[Chem 42]

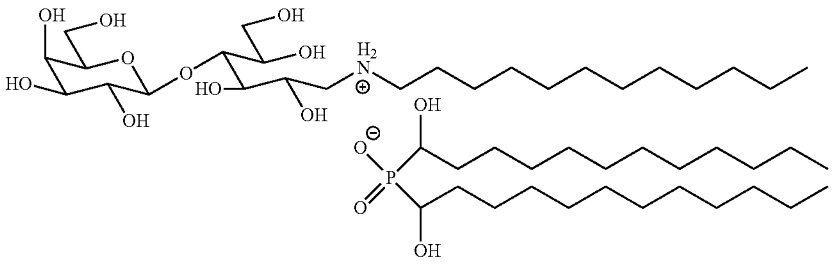

The formula of TriCat8 is as follows:

[Chem 43]

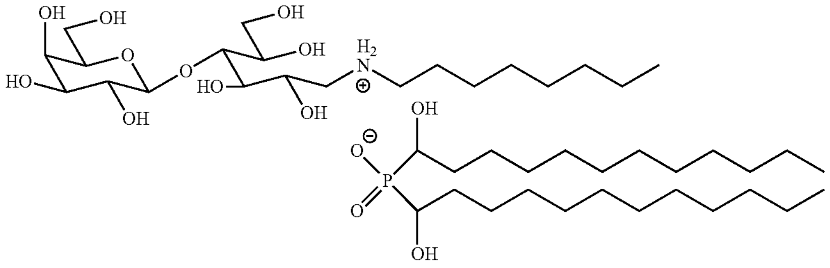

The formula of TriCat16 is as follows:

[Chem 44]

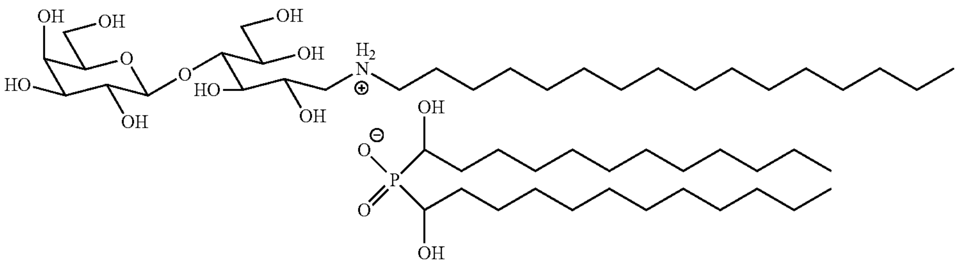

Counterexample: Preparing a Vesicle Comprising the ABP Dendrimer

To 5.82 mg of ABP dendrimer, 1.02 mg of N-dodecylamino-1-deoxylactitol (L-Hyd 12) and 0.87 mg of bis-α-(hydroxydodecyl)phosphinic acid 2 mL of ultrapure water are added at room temperature. The mixture is vortexed for 5 min then sonicated with an ultrasonic probe for 15 min at power 3 with 30% active cycles while controlling the temperature to be 45° C.

Preparation of a Vesicle Comprising the G1-A Dendrimer (TriCat12/G1-A)

To 5.29 mg of G1-A dendrimer, 1.02 mg of N-dodecylamino-1-deoxylactitol (L-Hyd 12) and 0.87 mg of bis-α-(hydroxydodecyl)phosphinic acid 2 mL of ultrapure water are added at room temperature. The mixture is vortexed for 5 min then sonicated with an ultrasonic probe for 15 min at power 3 with 30% active cycles while controlling the temperature to be 45° C.

Preparation of a Vesicle Comprising the G1-X-NIR Dendrimer (TriCat12/G1-X-NIR)

To 5.31 mg of G1-X-NIR dendrimer, 1.02 mg of N-dodecylamino-1-deoxylactitol (L-Hyd 12) and 0.87 mg of bis-α-(hydroxydodecyl)phosphinic acid 2 mL of ultrapure water are added at room temperature. The mixture is vortexed for 5 min then sonicated with an ultrasonic probe for 15 min at power 3 with 30% active cycles while controlling the temperature to be 45° C.

Preparation of a Vesicle Comprising the G1-B Dendrimer (TriCat12/G1-B)

To 5.21 mg of G1-B dendrimer, 1.02 mg of N-dodecylamino-1-deoxylactitol (L-Hyd 12) and 0.87 mg of bis-α-(hydroxydodecyl)phosphinic acid 2 mL of ultrapure water are added at room temperature. The mixture is vortexed for 5 min then left under magnetic stirring (500 rpm) for 24 h at room temperature.

Preparation of a Vesicle Comprising the G1-C Dendrimer (TriCat12/G1-C)

To 5.3 mg of G1-C dendrimer, 1.02 mg of N-dodecylamino-1-deoxylactitol (L-Hyd 12) and 0.86 mg of bis-α-(hydroxydodecyl)phosphinic acid 2 mL of ultrapure water are added at room temperature. The mixture is vortexed for 5 min then sonicated with an ultrasonic probe for 15 min at power 3 with 30% active cycles while controlling the temperature to be 45° C.

Preparation of a Vesicle Comprising the G1-B Dendrimer and TriCat8 (TriCat8/G1-B)

To 5.21 mg of G1-B dendrimer, 0.94 mg of N-octylamino-1-deoxylactitol (L-Hyd 8) and 0.86 mg of bis-α-(hydroxydodecyl)phosphinic acid 2 mL of ultrapure water are added at room temperature. The mixture is vortexed for 5 min then left under magnetic stirring (500 rpm) at 40° C. for 15 minutes then for 24 h at room temperature.

Preparation of a Vesicle Comprising the G1-B Dendrimer and TriCat 16 (TriCat16/G1-B)

To 5.21 mg of G1-B dendrimer, 1.16 mg of N-hexadecylamino-1-deoxylactitol (L-Hyd 16) and 0.86 mg of bis-α-(hydroxydodecyl)phosphinic acid 2 mL of ultrapure water are added at room temperature. The mixture is vortexed for 5 min then left under magnetic stirring (500 rpm) at 40° C. for 15 minutes then for 24 h at room temperature.

3. Measurement by DLS

The size and the size distribution of the vesicles are measured by DLS (dynamic light scattering). Each analysis is carried out on the samples, filtered at 1.2 μm with a Minisart Cellulose Acetate filter, placed in plastic cuvettes (semi-micro Polystyrene cuvettes, Brand). Measurements are carried out on a Malvern Instruments Nano S or Nano ZS instrument, both equipped with a He—Ne laser that emits monochromatic light at a wavelength of 633 nm. The scattered intensity is measured at 25.0° C.±0.1° C. at an angle of 173°. The result is an average of 4 measurements and has been processed by the Contin algorithm.

4. Measuring the Transition Temperature

The samples are prepared saturated at $1.10^{-2}$ M in TriCat12. Equimolar amounts of L-Hyd12 and phosphonic acid are dispersed at a concentration of $1.10^{-2}$ M and dendrimer at a concentration of 5.10-4 M in 2 mL water. The mixture is stirred at 300 rpm for 2 days. Two methods are carried out: the first consists of freeze-drying the medium then dispersing it in 100 μL of water followed by the traditional vesicle formation protocol. The second method consist of immediately sonicating 100 μL of the medium right away without going through the freeze-drying step. An identical result is obtained by both methods.

Another method consist of immediately sonicating the mixture following the classical protocol without going through the stirring step; similar results are obtained but with this method there is more background noise.

The measurements are then carried out on a DSC 1 STARe System with MultiSTAR® HSS8 sensor. In this device, the sample crucible and the reference crucible are placed in the same oven. To maximize the intensity of the product signal, the reference is filled with 75 μL of the solvent while 75 μL of the solution to be analyzed are placed in the sample crucible. The method developed consists of bringing the sample from 25 to 5° C. at 5° C./min then to run 4 cycles from 5 to 60° C. at 2° C./min.

5. Measuring the Encapsulation Rate

In order to assess the encapsulation efficiency of the dendrimer in TriCat12/dendrimer vesicles, a spectrofluorimetric assay was developed using the fluorescent analog of the dendrimer, G1-X-NIR.

The total amount of G1-X-NIR (encapsulated or not) was determined by measuring the fluorescence intensity (FI) of a sample for which the vesicular structures were broken by adding methanol to the solution (1 mL of methanol per 20 μL of vesicular solution).

At the same time, the unencapsulated G1-X-NIR was separated from the vesicles by filtration at 1.2 μm (Minisart Cellulose Acetate filter, Sartorius). A control solution of G1-X-NIR made it possible to verify the removal of 70% (SD=3%) of G1-X-NIR by this technique (to be taken into account in the calculation). After dilution of the filtrate in methanol (1 mL methanol per 20 μL of filtrate), the fluorescence intensity (FI) measurement made it possible to quantify the predominantly encapsulated G1-X-NIR.

$$\%\text{ removed} = \left[1 - (\{FI\text{ encapsulated dendrimer}\}/(\text{total dendrimer } FI\})\right] \times 100 \times 1.43 \quad \text{[Math. 1]}$$

$$EE\ (\%) - 100 - \%\text{ removed} \quad \text{[Math. 2]}$$

6. Observation by Cryo-SEM

The observation of the vesicles was carried out by scanning electron microscopy after cryofracture (Cryo-SEM). The apparatus used for the analysis is an ESEM Quanta FEG250 from FEI (Plateforme TRI-Genotoul), operating at 5 kV and about 1,104 Pa. The solutions are deposited on the sample holder and then solidified in pasty dinitrogen (−210° C.). They are then fractured in a chamber at −140° C. Then the sample undergoes a sublimation step at −90° C. for 5 minutes. The sample then undergoes 60 s of platinum plasma coating. It is transferred for observation into the cryogenic chamber of the SEM, kept at all times at −140° C. by a flow of dinitrogen gas.

7. Measuring the Stability of the Formulation at 4° C.

TriCat12/dendrimer solutions are stored at 4° C. in DLS cuvettes. At the time of size measurement, the solution is brought to room temperature for 5 min and then the size is measured at 25° C. using DLS.

8. Measuring the Stability of the Formulation after Freezing

To assess the freezing stability of the formulation, aliquots of the TriCat12/dendrimer formulation are frozen at −20° C. After a time t (days), the solution is thawed in an ultrasonic bath at 25° C. for 10 min, filtered to 1.2 μm then the size is measured using DLS at 25° C.

9. Preparing a Xanthan Pharmaceutical Formulation Comprising TriCat12/G1-Xvesicles A 2% wt Xanthan solution in water is prepared: 20 mg of Xanthan are sprinkled under stirring at 500 rpm, into 1 mL of 0.2 μm filtered mQ water.

The mixture is stirred for at least 1 h. Then, an equivolume mixture of Tricat12/G1-X vesicles and 2% wt Xanthan gel is made. It is left under agitation at 500 rpm for at least 4 h.

10. Measuring Physical Stability

The study of the physical stability of TriCat12/G1-B vesicles and of the pharmaceutical formulation of TriCat12/G1-B in xanthan is measured using a Turbiscan Lab Expert (Formulaction). The Turbiscan detects the variations of the intensity of the transmitted light at different heights (z) of the sample as a function of time, thus allowing a direct follow-up of the local physical heterogeneities. Measurements are performed according to the protocol of 145 scans/1 hour, then 145 scans/24 h at 25° C.

11. Measuring Stability by NMR

The G1-X compounds were solubilized in water then the pH was adjusted to pH=4 and the solutions were stored at 25° C. protected from light. Just before the NMR analysis, the solution is freeze-dried and the resulting powder (20 to 50 mg) is diluted in 0.5 to 0.7 mL of $D_2O$ in the presence of 6 drops of CD3CN. TriCat 12/G1-B preformulations immobilized in a xanthan gel were prepared according to the invention; if necessary the pH was adjusted to pH=4 and the solutions were stored at 25° C. protected from light. NMR spectra were recorded at 25° C. after adjusting the pH to pH=7 then freeze-dried. The resulting powder is humidified with a few drops of D20 before analysis by solid state NMR (MAS NMR).

12. Evaluating In Vitro Skin Penetration on Franz Cells

Quantification of Fluorescent Dendrimer (G1X-NIR) in the Skin

The Franz type continuous flow cell diffusion method (PermGear@, Standard Franz Cells) is used to study in vitro the skin penetration of the formulation over time without disrupting the system. These experiments were performed on pig ear skin, which represents a predictive model of human skin penetration, having similar histological and physiological properties to human skin. Samples of pig ear skin were obtained from the slaughterhouse (Arcadie Sud-Ouest, Montauban), so that the skin tissue was intact. After dissecting the skin from the underlying tissue, the skin is cleaned with water, degreased, depilated and then cut into square pieces of about 2 cm. These skin patches are frozen at −80° C. for subsequent use.

In the experiment, the skins were thawed at room temperature and placed on the Franz cells in the donor compartment so that the side that is bathed in the receiving fluid corresponds to the inner side of the skin while the side that is in contact with the air is that of the stratum corneum.

A fluorescent dendrimer analogue is used with near infrared emission (G1-X-NIR), for in vitro skin penetration and retention studies. Adose (300 μL) of PBS (blank), G1-X-NIR alone or formulated in TriCat12/G1-X-NIR vesicles was deposited on the face of the stratum corneum, using a micropipette, to cover the scattering area of 1.77 $cm^2$ for 24 h. The outer surface of the cell was covered with parafilm to avoid evaporation and volume changes. The receptor compartment in contact with the inner surface of the skin was filled with 12 mL of phosphate buffer solution (PBS; pH=7.45), thermostated at 37° C. and maintained under constant agitation (300 rpm) to ensure constant volume turnover, which approximates physiological conditions.

After 24 h, the skin is rinsed with PBS to remove the remaining deposit and dried with paper towels. The treatment area is then cut into small pieces in a pillbox with 3 mL of PBS and homogenized with a disperser (Ultra-Turrax Ika®—Werke, T 25 Basic) for 5 min at 21500 rpm. The dispersion is then filtered at 0.45 μm (Minisart Cellulose Acetate filter, Sartorius) then the dendrimer in the filtrate is assayed by spectrofluorometry (λ excitation=632 nm and λ emission=650 to 850 nm).

Observation of Skin Penetration by Confocal Microscopy

Confocal microscopy is chosen to evaluate the depth of penetration of G1-X-NIR in the different layers of the skin (Stratum corneum, viable epidermis, and dermis). The first step is the diffusion of G1-X-NIR on Franz cell, according to the protocol described previously.

After 24 h of application, the skin is gently rinsed with PBS and dried. The treated area is cut into three equal pieces to be representative of the entire skin. These three pieces are frozen, embedded in O.C.T (Tissue-Tek®) in a plastic mold (Tissue-Tek® Cryomold®), in isopentane cooled to −80° C. 10 μm thick sections obtained with a cryostat (CM1950, Leica), are then observed with a Leica SP8 confocal microscope with an inverted objective (63X), with oil immersion. The parameters used during the observation on the LAS X software are: A excitation=635 nm and λ emission=650 to 800 nm. PBS-treated skin is used as a blank to assess skin auto-fluorescence. The obtained images are then processed on the Fiji software with the Bio-formats plugin.

13. Monocyte Purification and FACS Analysis

Human blood from healthy donors is collected from the French national blood bank (EFS, Toulouse, France). Peripheral blood mononuclear cells (PBMCs) are then separated from the blood using a density gradient with a Pancoll solution (PANBiotech GmbFI) by centrifugation at 1200 rpm for 20 min at 20° C. From PBMCs, monocytes are isolated by negative selection with antibodies against all blood cells (T cells, B cells, NK cells, dendritic cells, erythrocytes and granulocytes) except monocytes using the Dynabeads® Untouched™ Human Monocytes kit (Invitrogen). Monocyte purity was verified by flow cytometry to be greater than 90% for each donor with an anti-CD14-APC-Cy7 antibody (Miltenyi Biotec).

The freshly purified monocytes were resuspended in a 48-well plate at 1 million per mL in RPMI 1640+GLUTAMAX, 100 U/mL penicillin and streptomycin and 10% fetal calf serum (FCS). All the molecules were added at the beginning of the cultures at the concentration of 20 μM of G1-X except TriCat12 alone at the concentration of 40 μM. After 5 days of culture at 37° C., monocyte morphology was analyzed by flow cytometry with a MACSQUANT Q10 cytometer (Miltenyi Biotec). All cytometry data were analyzed by the Flowlogic™ software (Miltenyi Biotec).

14. Evaluating Anti-Psoriatic Activity In Vivo on IMQ Mice

Eight-week-old female Balb/c mice, weighing approximately 20 g, were used in these experiments. The experimental procedures were evaluated and approved by the Animal Experimentation Ethics Committee. The operations and experimental procedures are performed under gas anesthesia, carried out in an anesthesia station by inhalation of 4% isoflurane in the induction box then 3% by mask. After one week of acclimatization, the backs of the mice are shaved at D-1, over an area of about 4 $cm^2$ using a trimmer, and residual hair is removed using a depilatory cream. At DO, 80 mg of Aldara™ cream with 5% Imiquimod (IMQ) was applied and massaged on the backs of the mice daily for 7 consecutive days, in the late afternoon. The next morning, the backs of the IMQ-treated animals were washed with water-soaked cotton. The following treatments are then applied in a volume of 100 μL: water (control), G1-A or G1-B dendrimers dissolved in water (amount corresponding to a final dose of 13 mg/kg), and G1-A or G1-B dendrimers formulated in TriCat12 vesicles (amount corresponding to a final dendrimer dose of 13 mg/kg). At D7, 5 hours after the last treatment, the mice are euthanized. The severity of the inflammation of the skin on the back of the mice was assessed using a clinical score based on the Psoriasis Area Severity Index (PASI) score. The severity of the skin inflammation was determined by daily assessment of erythema, scales, and back thickness according to a score ranging from 0 to 4 (0=normal; 1=mild; 2=moderate; 3=marked; 4=very marked).

The thickness of the back was measured with a caliper. A total clinical score combining these three clinical criteria was then calculated (scale from 0 to 12).

Upon euthanasia, the back skins are removed, fixed immediately in 4% paraformaldehyde and embedded in paraffin blocks. For histological evaluation, Hemalun-Eosin (HE) staining is performed on 5 μm deparaffinized skin sections. Images are obtained with a slide scanner (Panoramic slide scanner 250, 40× objective). The severity of the inflammation, at the histological level, was assessed based on the following histopathological features of psoriasis: acanthosis, spongiosis, hyperkeratosis, parakeratosis, and immune infiltrate. For each of these five criteria, a score ranging from 0 (normal) to 4 (severe) was assigned, then the scores were aggregated to give the total histologic grade (scale of 0 to 20).

15. Keratinocyte Proliferation

To investigate the effect of dendrimers on keratinocyte proliferation in vitro, the expression of the proliferation marker Ki67 (nuclear marker) was studied by immunohistochemistry after treatment or not (control) with 20 μM of G1-A or of G1-B for 24, 48, or 72 h. Two types of keratinocytes were studied: the human N-TERT line and primary human keratinocytes. Following treatment with dendrimers, cells are washed, fixed in para-formaldehyde (PFA) and permeabilized with triton. Next, the fixed cells are incubated with a rabbit primary antibody against Ki67, then washed and incubated with an anti-rabbit secondary antibody coupled to Alexa Fluor 488 fluorochrome. Cell nuclei are stained with 4',6-diamidino-2-phenylindole (DAPI). The keratinocytes were then observed with a wide-field fluorescence microscope. For each observation area, two images are acquired: one with the ultraviolet laser to observe DAPI staining of nuclei; one with the green laser to observe Ki67 staining. These images are processed with the software ImageJ. On the image corresponding to the DAPI staining, the nuclei are counted to obtain the total cell count per image. On the image corresponding to Ki67 staining, Ki67 positive nuclei are counted to obtain the number of cells that proliferate, and to calculate the percentage of proliferating cells.

II. Results

1. TriCat12/ABP formulation 1.1 Characterization of the Vesicles

Figure 2:
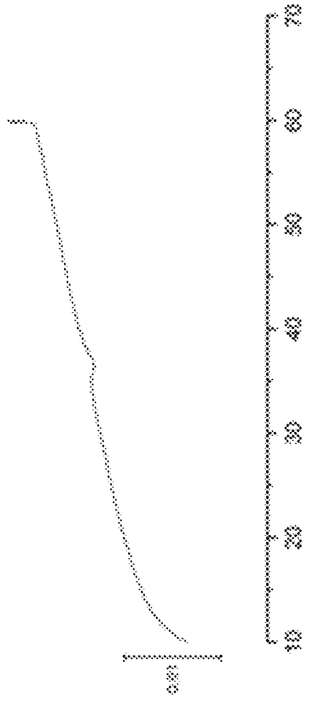
FIG. 2

The TriCat12/ABP formulation preparation method makes it possible to obtain vesicles with an average diameter around 250-300 nm with a bilayer transition temperature of 37° C. [FIG. 2], The TriCat12/ABP formulation preparation method is able to encapsulate on average between 25% of the dendrimer initially committed in the formulation. The separation of the non-encapsulated dendrimer is difficult to achieve with techniques known to the person skilled in the art. The Zeta potential is −55±4 mV and the pH of the solution ~6.5.

1.2 Penetration of the Formulation into the Skin

Figure 3:
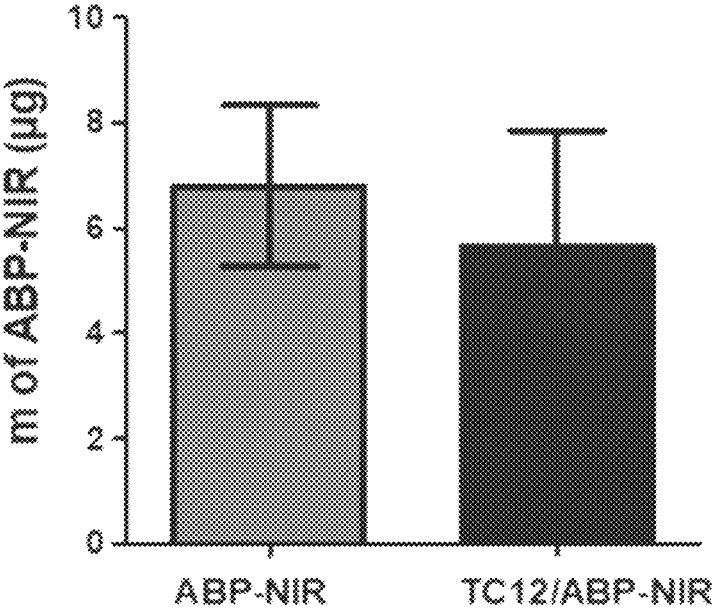
FIG. 3

Fluorescence quantification of the amount of ABP-NIR dendrimer (ABP dendrimer in its fluorescent form) formulated or not with TriCat 12, which penetrated the pig ear skin (Franz cells) shows that after 24 h at 40° C., the ABP dendrimer, formulated or not, penetrates only slightly into the skin [FIG. 3].

2. TriCat12/G1-A Formulation 2.1 Characterization of the Vesicles

Figure 4:
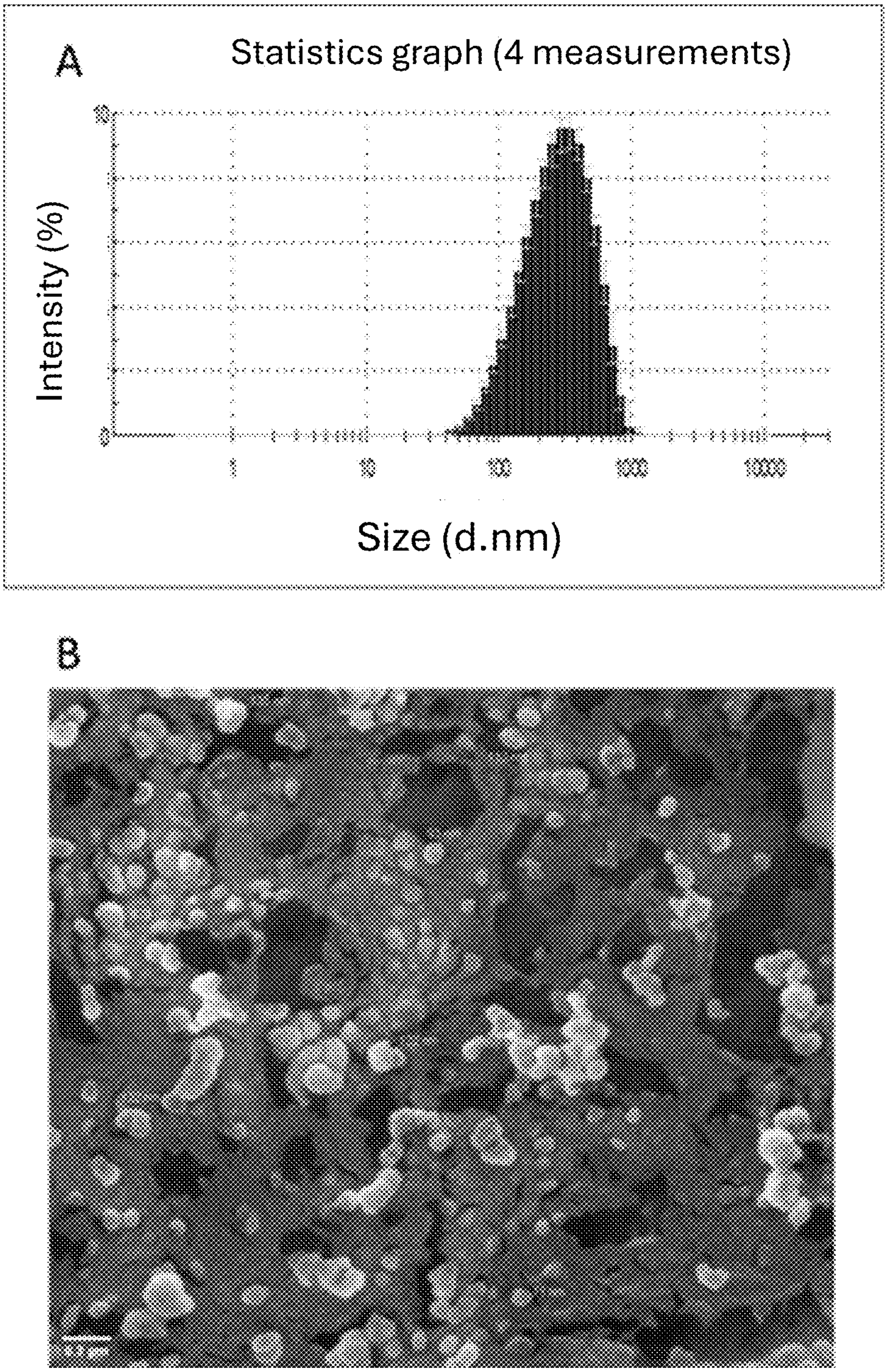
FIG. 4

The method of preparing the formulation using a dendrimer precursor in its phosphonic acid form allows to increase its capacity of insertion in the hydrophobic part of the vesicles and thus to obtain an average encapsulation rate of 75% and to simply separate the non-encapsulated active ingredient by filtration. The formulation of the G1-A dendrimer by TriCat-12 results in the formation of vesicles, the an average diameter of which is around 100-350 nm [FIG. 4].

Figure 5:
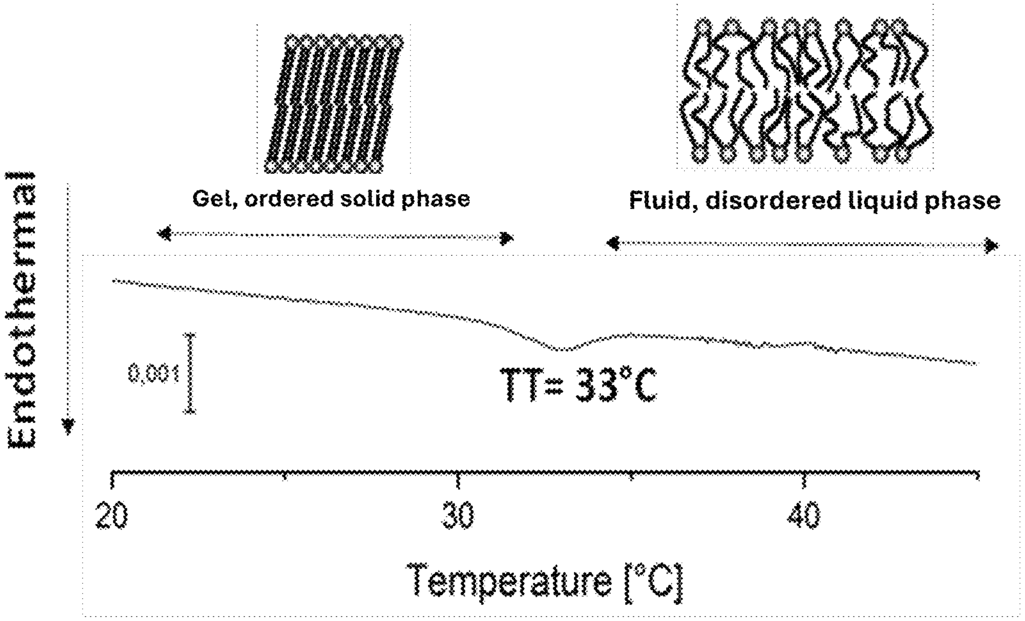
FIG. 5

The TriCat 12/G1-A formulation has a phase transition temperature of 33° C. Below 33° C., the membrane bilayer of the vesicle is rigid and stable. Above 33° C. (skin temperature oscillates between 3° and 35° C.), this membrane becomes fluid and its bio-adressing properties are increased (diffusion into the tissues, fusion with the cells, release of active ingredients) [FIG. 5].

The Zeta potential is −53±2.5 mV and the pH of the solution ~2.8.

Likewise, the formulation of the G1-A-NIR dendrimer by TriCat-12 results in the formation of vesicles, the average diameter of which is around 100-350 nm. The pH of the solution is ~2.8. The TriCat 12/G1-A-NIR formulation is stable for at least 1 month when stored at 4° C. in solution.

2.2 Stability of the TriCat12/G1-A Formulation

Figure 6:
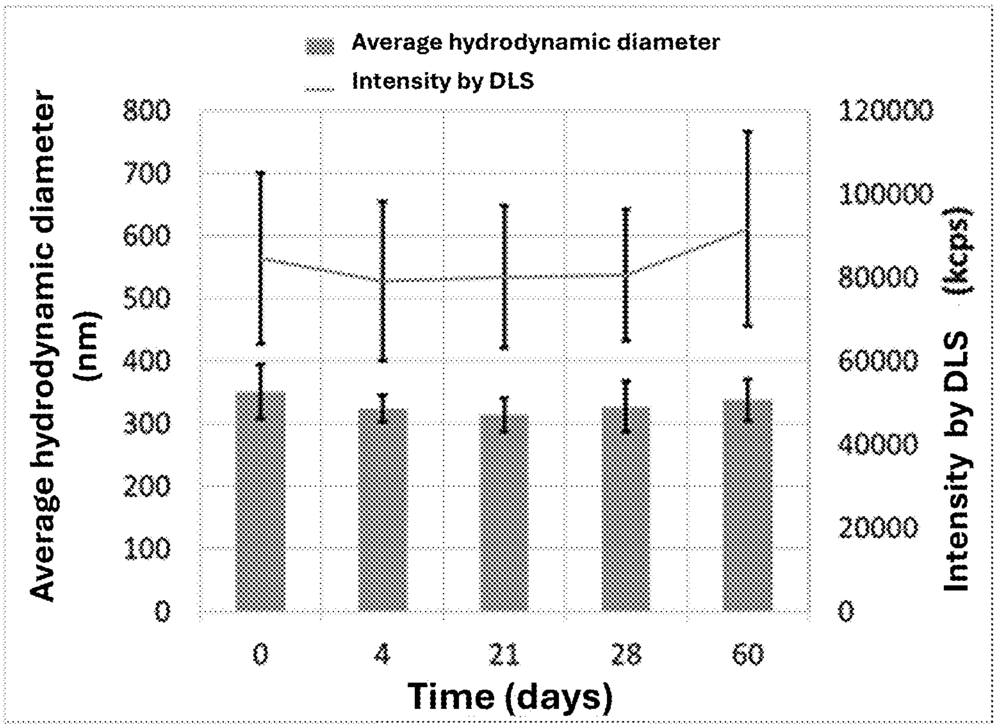
FIG. 6

The TriCat 12/G1-A formulation is stable for over two months when stored at 4° C. in solution [FIG. 6].

Figure 7:
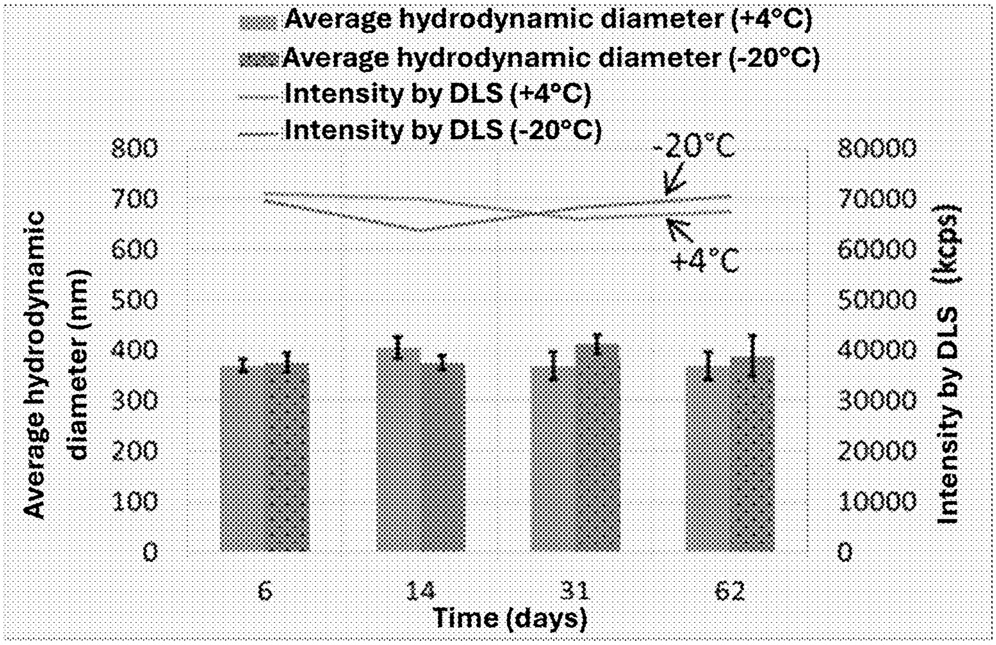
FIG. 7

Experiments were carried out to test whether the vesicles could be damaged by a freezing step. These experiments demonstrate that the formulations can be frozen and thawed without changing their physical or chemical properties [FIG. 7].

2.3 Penetration of the Formulation into the Skin

Figure 8:
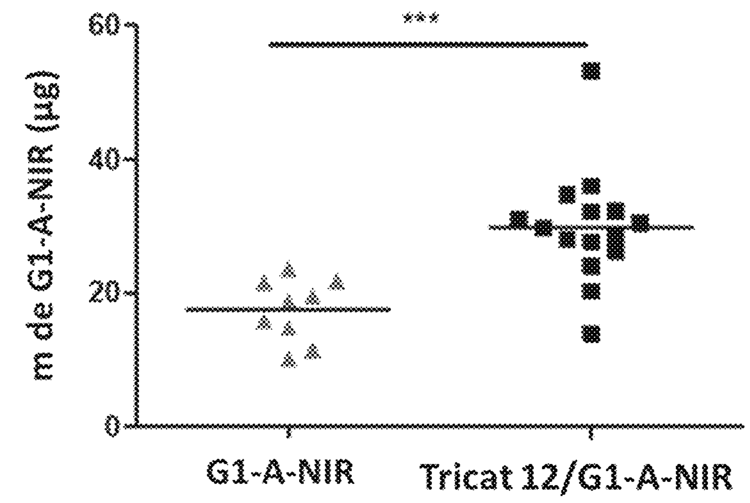
FIG. 8

The continuous-flow Franz cell diffusion method is used to study in vitro the skin penetration of the formulation over time. These experiments were done on pig ear skins, whose histological and physiological properties are similar to those of human skin. These experiments show that after 24 h, the amount of dendrimer that has penetrated the skin is significantly higher when it is formulated [FIG. 8]).

Figure 9:
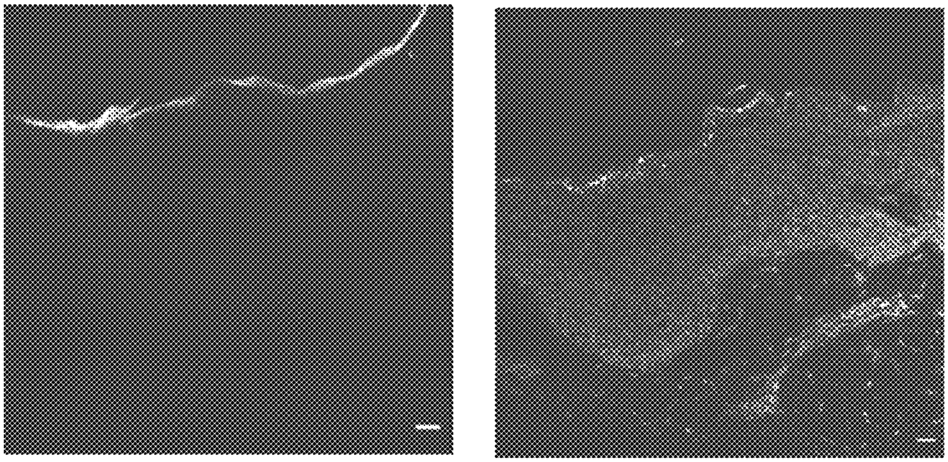
FIG. 9

Confocal microscopy was chosen to evaluate the depth of penetration of the dendrimer into the different layers of the skin (Stratum corneum, viable epidermis, and dermis). Confocal microscopy experiments show that the dendrimer only penetrates the epidermis and dermis when it is formulated in the vesicles, otherwise it remains in the superficial layers of the skin (stratum corneum) [FIG. 9].

Figure 10:
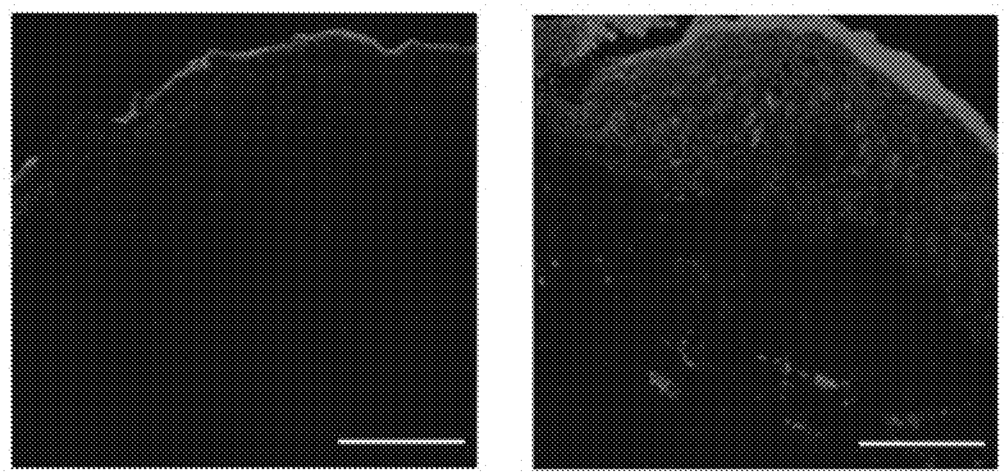
FIG. 10

Experiments done on human skins, from human skin biopsies. These experiments show that after 24 h, the amount of dendrimer that has penetrated the skin is significantly higher when it is formulated [FIG. 10].

2.4 Monocyte Activation

Figure 11:
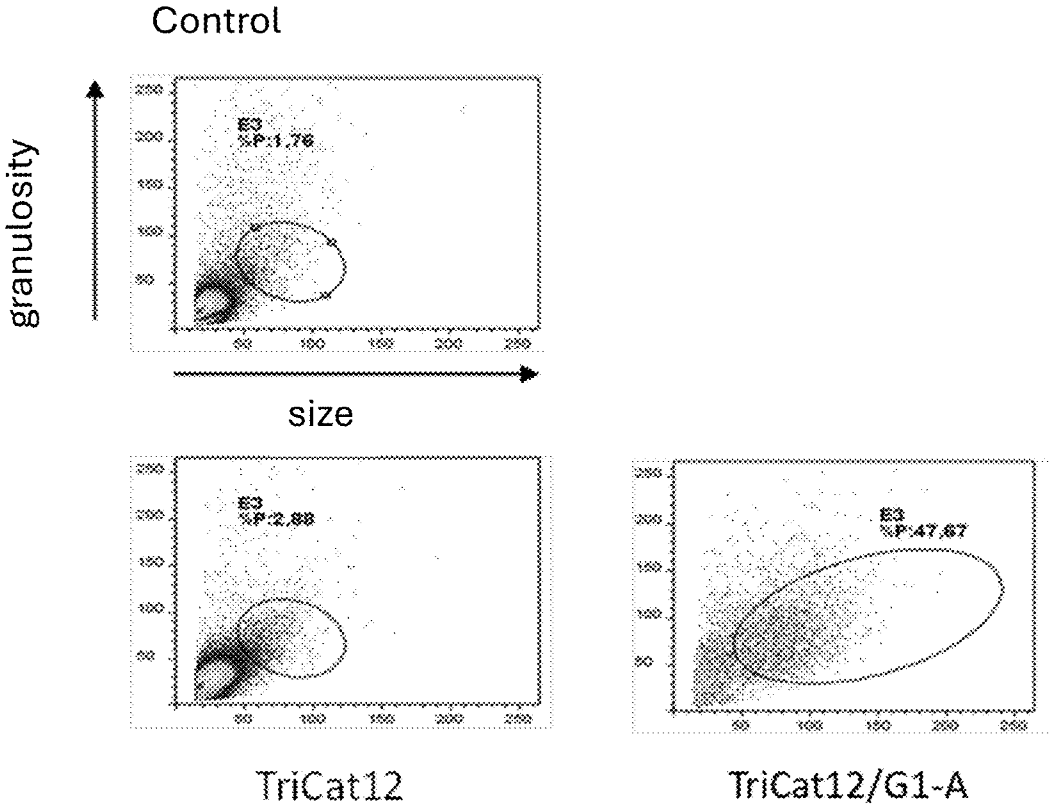
FIG. 11

A change in morphology (increased granularity and size) reflects activation of primary human monocytes. The results show that TriCat12 vesicles alone do not alter the morphology of human monocytes, whereas TriCat12 vesicles loaded with the G1-A dendrimer result in increased granularity and size. Furthermore, we note that almost half of the cells are in the ellipse of activated monocytes [FIG. 11].

2.5 In Vivo Activity in Psoriatic Mice The results of the clinical score follow-up of the 3 groups of mice (control: IMQ mice not treated, IMQ mice treated with 13 mg/kg of free G1-A dendrimer, and mice treated with 13 mg/kg of G1-A dendrimer formulated in TriCat12 vesicles) show a decrease in clinical score in the 2 treated groups. For untreated control mice, the mean clinical score is 9.5 at D7. The clinical score is decreased to 6.5 and 5.7 for the free G1-A dendrimer and TriCat12/G1-A formulated dendrimer groups, respectively [FIG. 12, top graph].

Figure 12:
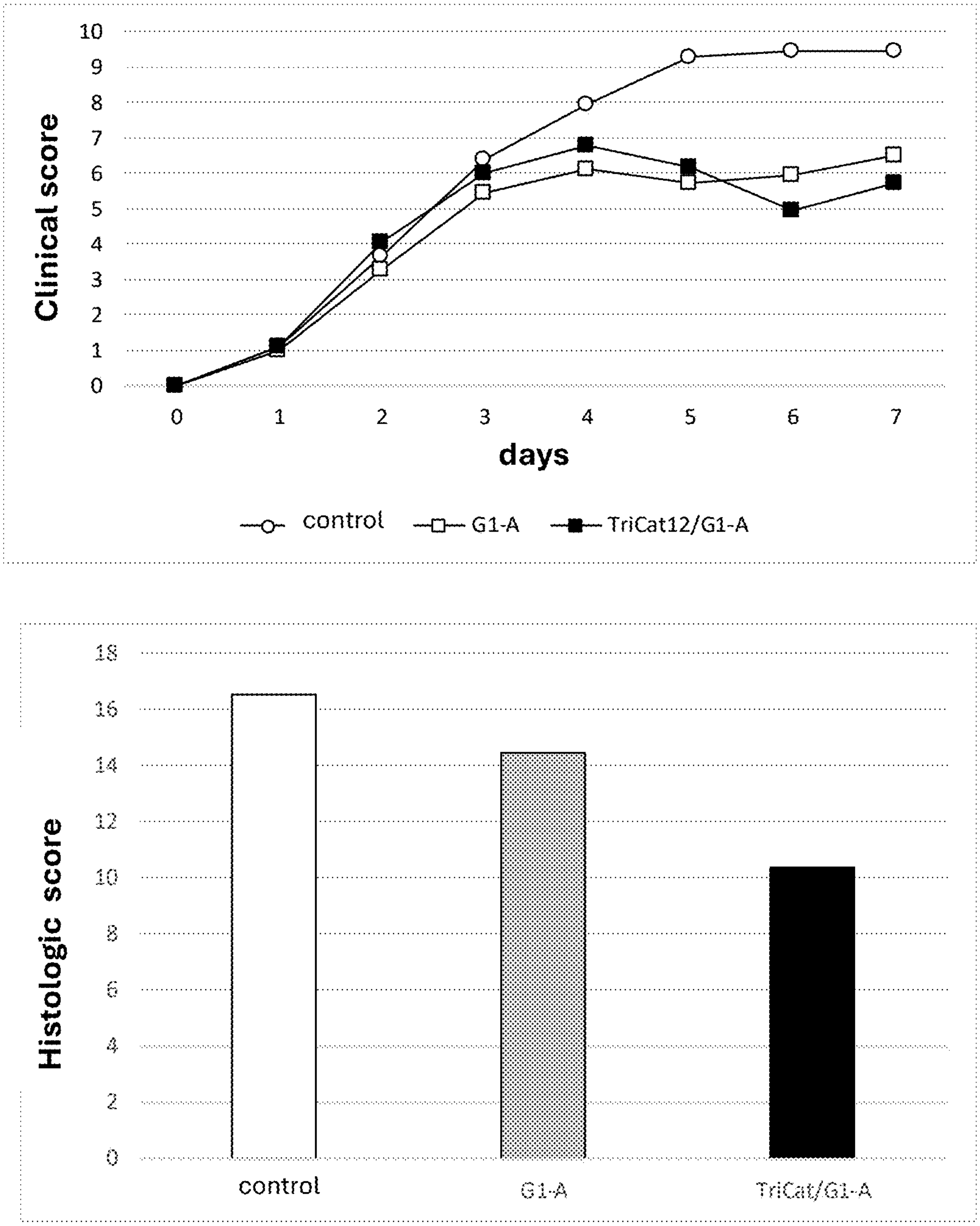
FIG. 12

The mean histologic score is also decreased from 16.5 for untreated control mice to 14.5 and 10.4 for the free G1-A dendrimer and formulated TriCat12/G1-A dendrimer groups, respectively [FIG. 12, bottom graph].

2.6 Keratinocyte Proliferation

Figure 13:
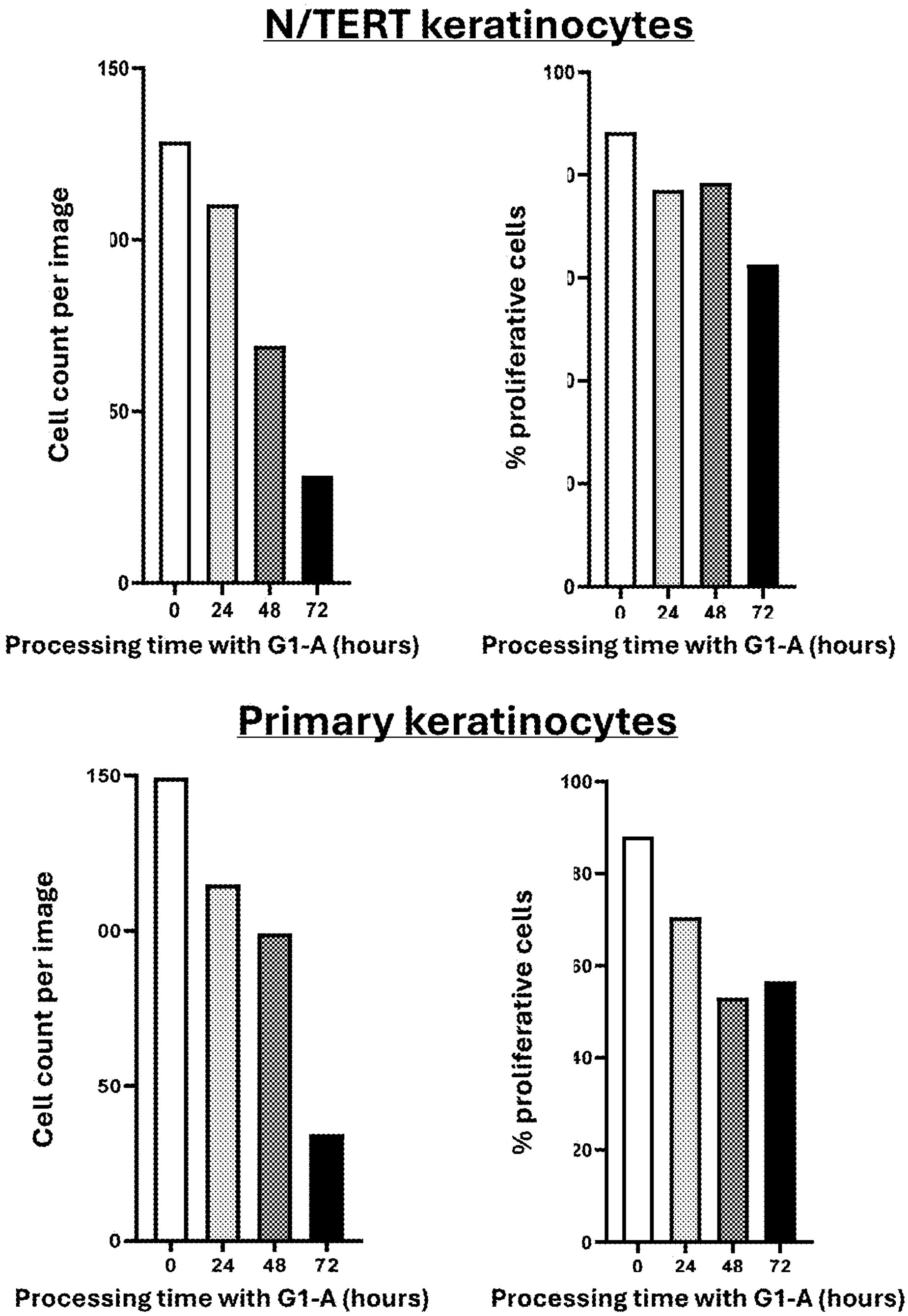
FIG. 13

FIG. 13 shows the antiproliferative effect of compound G1-A, as a function of treatment time, on the N-TERT keratinocyte line (top graphs) and on primary human keratinocytes (bottom graphs). A decrease in the total cell count and the percentage of proliferative cells is observed [FIG. 13].

3. TriCat 12/G1-B Formulation 3.1 Characterization of the Vesicles

Figure 14:
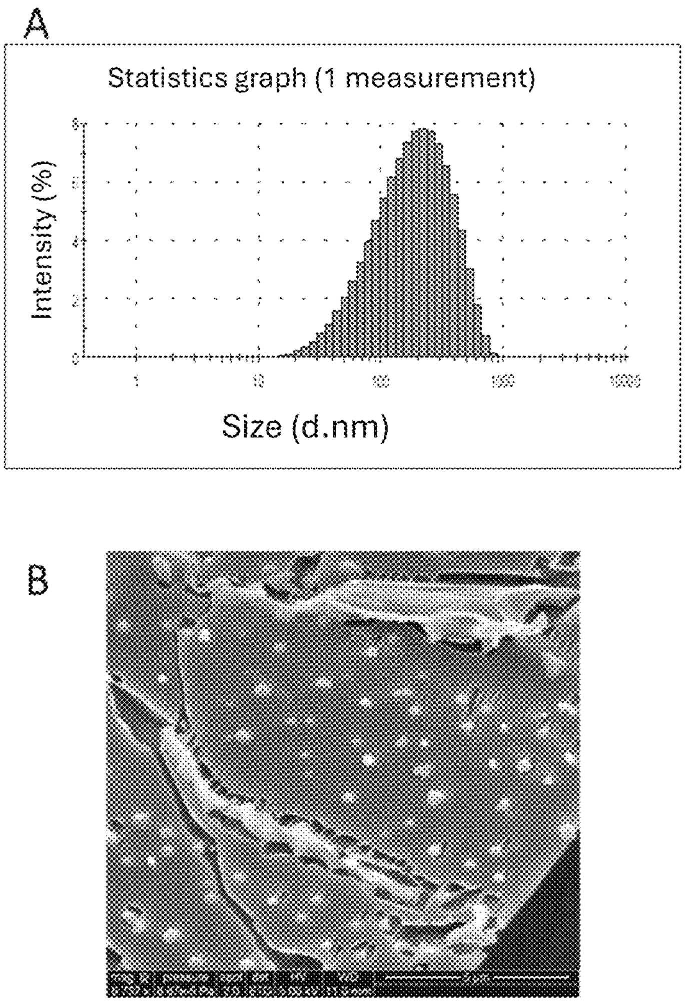
FIG. 14

The formulation of the G1-B dendrimer by TriCat-12 results in the formation of vesicles, with an average diameter around 200-300 nm [FIG. 14]. The average encapsulation rate is 70% for G1-B dendrimer.

The Zeta potential is −41±2.6 mV and the pH of the solution ~2.7.

Figure 15:
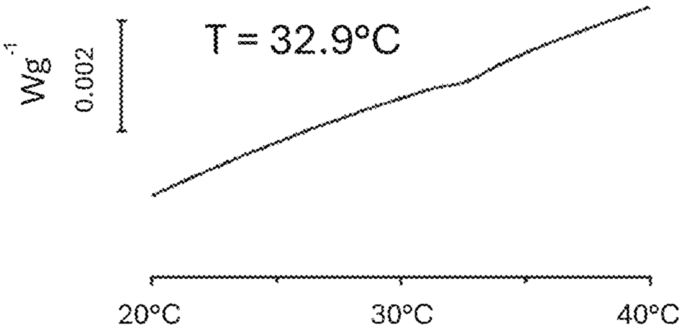
FIG. 15

Below 33° C. the membrane bilayer of the formulations is rigid and very stable. Above 33° C. (skin temperature oscillates between 3° and 35° C.), this membrane becomes fluid and its bio-adressing properties are increased (diffusion into the tissues, fusion with the cells, release of active ingredients) [FIG. 15].

3.2 Stability of the Formulation

Figure 16:
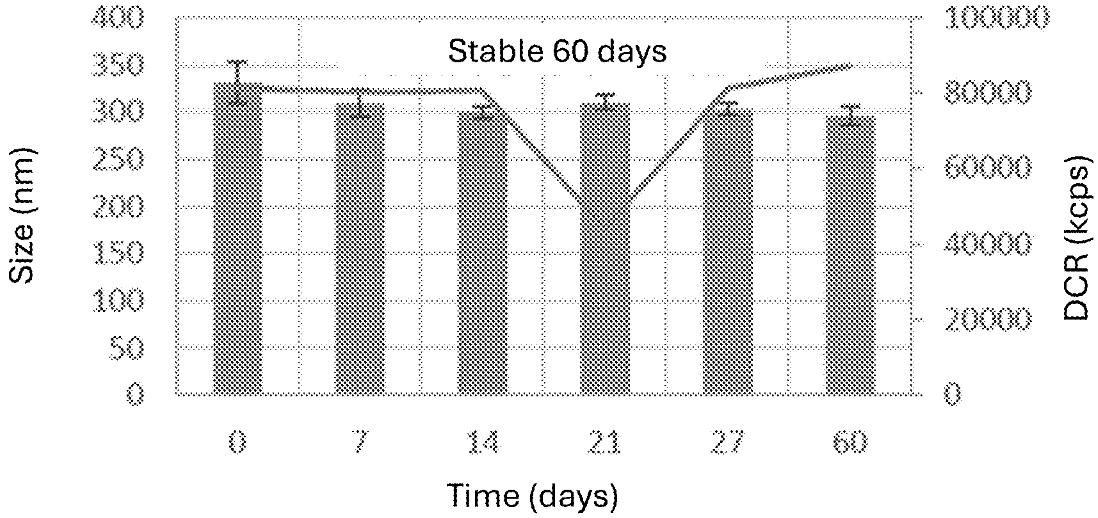
FIG. 16

The formulations are stable (in terms of diameter and quantity (represented by the scattered intensity DCR)) for more than two months when stored at 4° C. in solution [FIG. 16].

3.3 Pharmaceutical Composition of TriCat 12/G1-B with Xanthan

Figure 17:
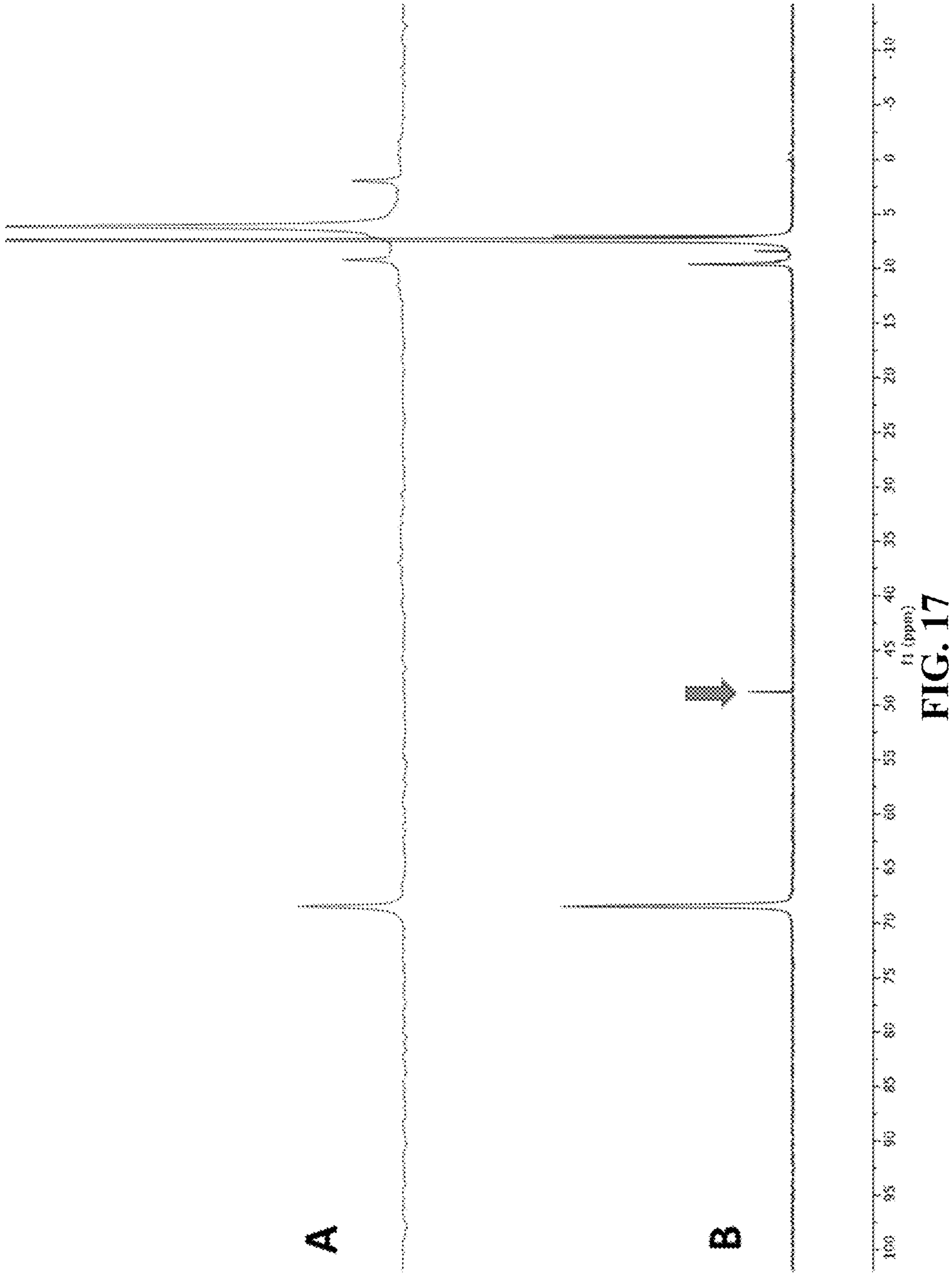
FIG. 17

The chemical stability of G1-B compounds in pre-formulations immobilized in a xanthan gel was evaluated by NMR in comparison with those of G1-B compounds alone at pH=4. The results show that the stability of compound G1-B in the TriCat 12/G1-X preformulation immobilized in a xanthan gel according to the invention is much higher than that of G1-B under the same conditions. 31P NMR spectroscopy shows a degradation of compound G1-B after 3 months of storage at pH=4 at 25° C. (spectrum B of [FIG. 17], signal attesting to acid hydrolysis at about 48 ppm symbolized by an arrow). Under the same conditions the compound G1-B in the TriCat 12/G1-X preformulation immobilized in a xanthan gel remains perfectly stable and no by-products are observed (spectrum A of [FIG. 17]).

Figure 18:
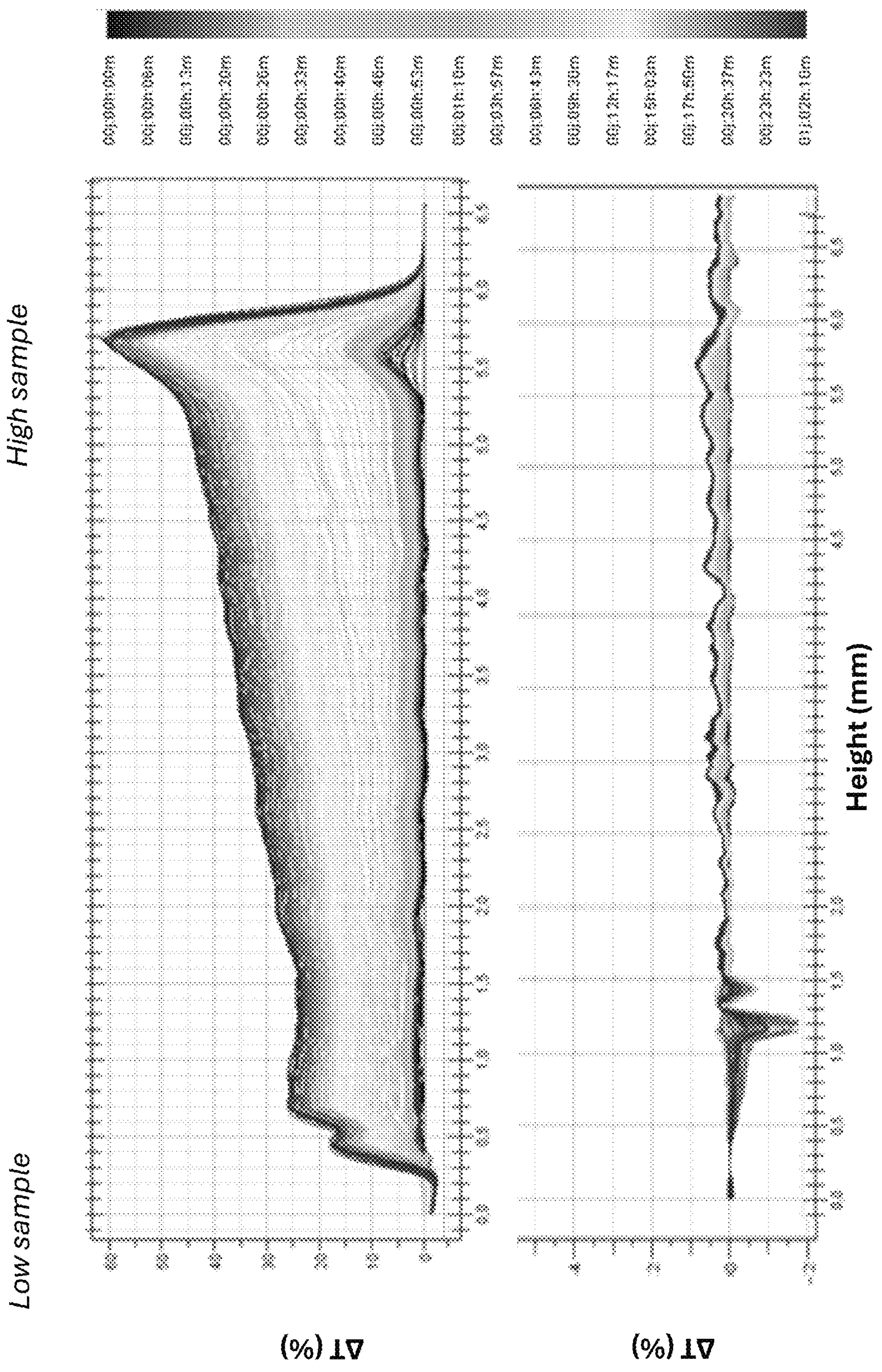
FIG. 18

The formulation of TriCat 12/G1-B vesicles in 1% Xanthan gel is stable in terms of physical stability of the sample even when stored at room temperature [FIG. 18]. For the formulation of TriCat 12/G1-B vesicles in a Xanthan gel no significant change in transmission through the sample is observed over the entire height of the sample after 24 h, whereas for TriCat 12/G1-B vesicles kept in water the transmission increases at the top of the volume showing a clarification of the solution due to a slight sedimentation of the vesicles. The pharmaceutical formulation of the vesicles in the xanthan gel allows for better preservation at room temperature.

3.4 Penetration of the Formulation into the Skin

Figure 19:
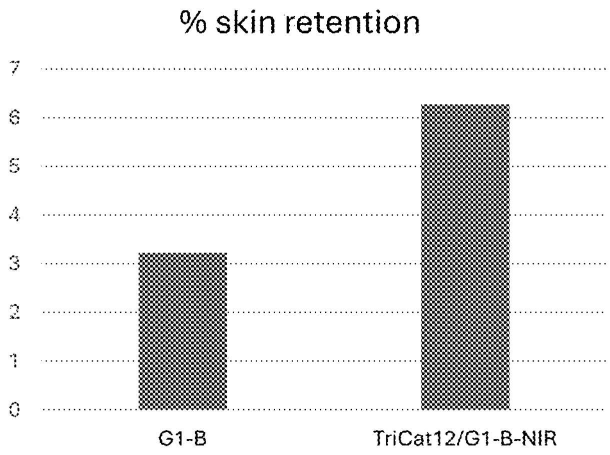
FIG. 19

The continuous-flow Franz cell diffusion method is used to study in vitro the skin penetration of the formulation over time. These experiments were done on pig ear skins, whose histological and physiological properties are similar to those of human skin. These experiments show that after 24 h, the amount of G1-B-NIR dendrimer that has penetrated the skin is significantly higherwhen formulated in TriCat 12/G1-B-NIR vesicles [FIG. 19]).

Figure 20:
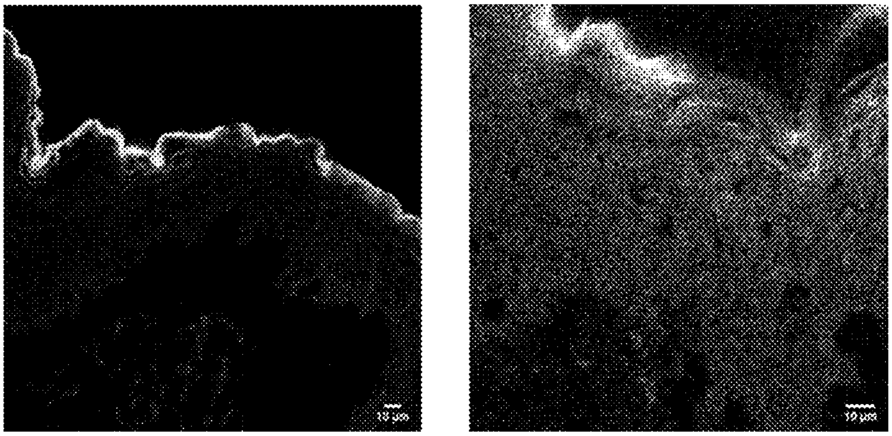
FIG. 20

Experiments on pig skin were also carried out to verify by confocal microscopy if the dendrimer could penetrate the deep layers of the skin. These pictures show that the dendrimer penetrates the epidermis better when it is formulated in the vesicles, otherwise it remains preferentially in the superficial layers of the skin (stratum corneum) [FIG. 20].

Figure 21:
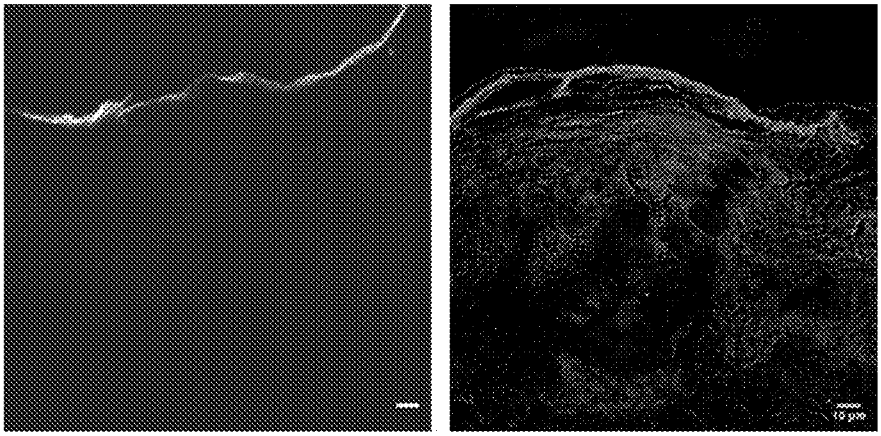
FIG. 21

Experiments on pig skin were carried out to verify by confocal microscopy whether the dendrimer formulated in vesicles and in 1% xanthan gel could penetrate into the deep layers of the skin. These pictures show that the dendrimer penetrates deeply into the epidermis and dermis when it is formulated in the vesicles included in the xanthan gel, otherwise it remains preferentially in the superficial layers of the skin (stratum corneum) [FIG. 21].

3.5 Monocyte Activation

Figure 22:
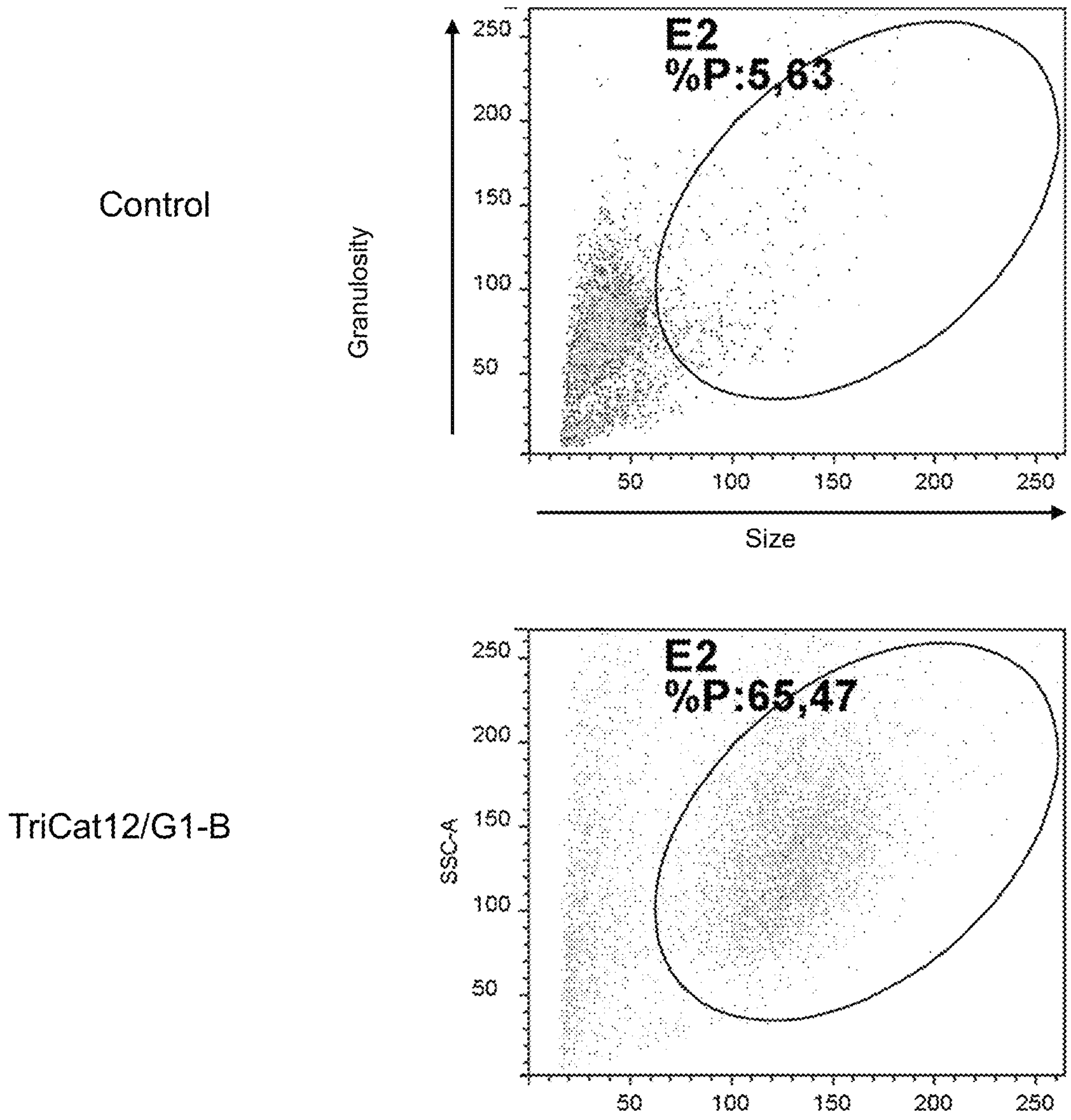
FIG. 22

A change in morphology (increased granularity and size) reflects activation of primary human monocytes. The results show that TriCat12 vesicles alone do not alter the morphology of human monocytes [FIG. 11], whereas TriCat12 vesicles loaded with the G1-B dendrimer result in increased granularity and size. Furthermore, we note that almost 2/3 of the cells are in the ellipse of activated monocytes [FIG. 22], 3.6 In Vivo Activity in Psoriatic Mice The results of the clinical score follow-up of the 3 groups of mice (control: IMQ mice not treated, IMQ mice treated with 13 mg/kg of free G1-B dendrimer, and mice treated with 13 mg/kg of G1-B dendrimer formulated in TriCat12 vesicles) show a decrease in clinical score in the 2 treated groups. For untreated control mice, the mean clinical score is 9.6 at D7. The clinical score falls to 7.8 and 6.4 for the free G1-B dendrimer and TriCat12/G1-B formulated dendrimer groups, respectively [FIG. 23, top graph].

Figure 23:
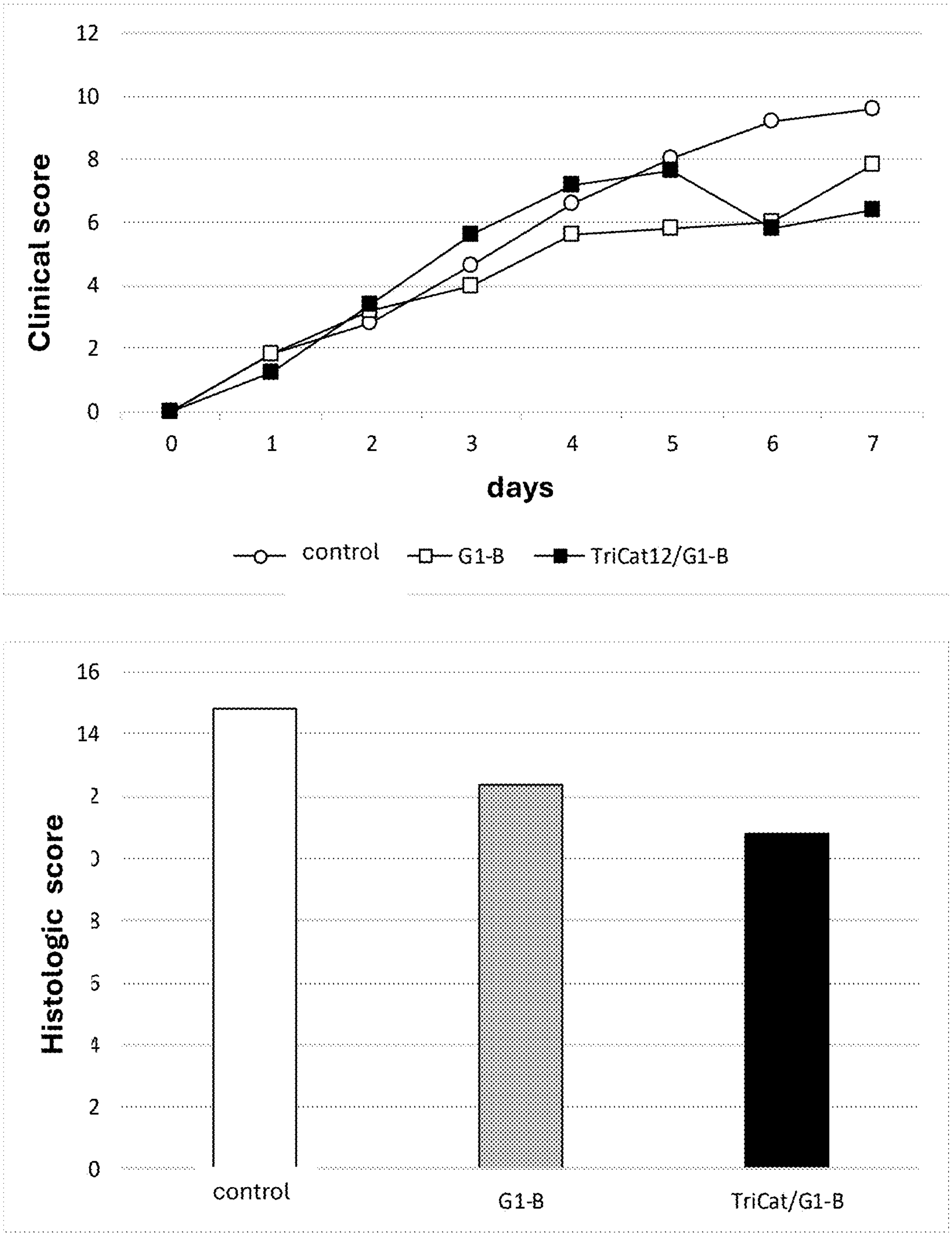
FIG. 23

The mean histologic score is also decreased from 14.8 for untreated control mice to 12.4 and 10.8 for the free G1-B dendrimer and formulated TriCat12/G1-B dendrimer groups, respectively [FIG. 23, bottom graph].

3.7. Keratinocyte Proliferation

Figure 24:
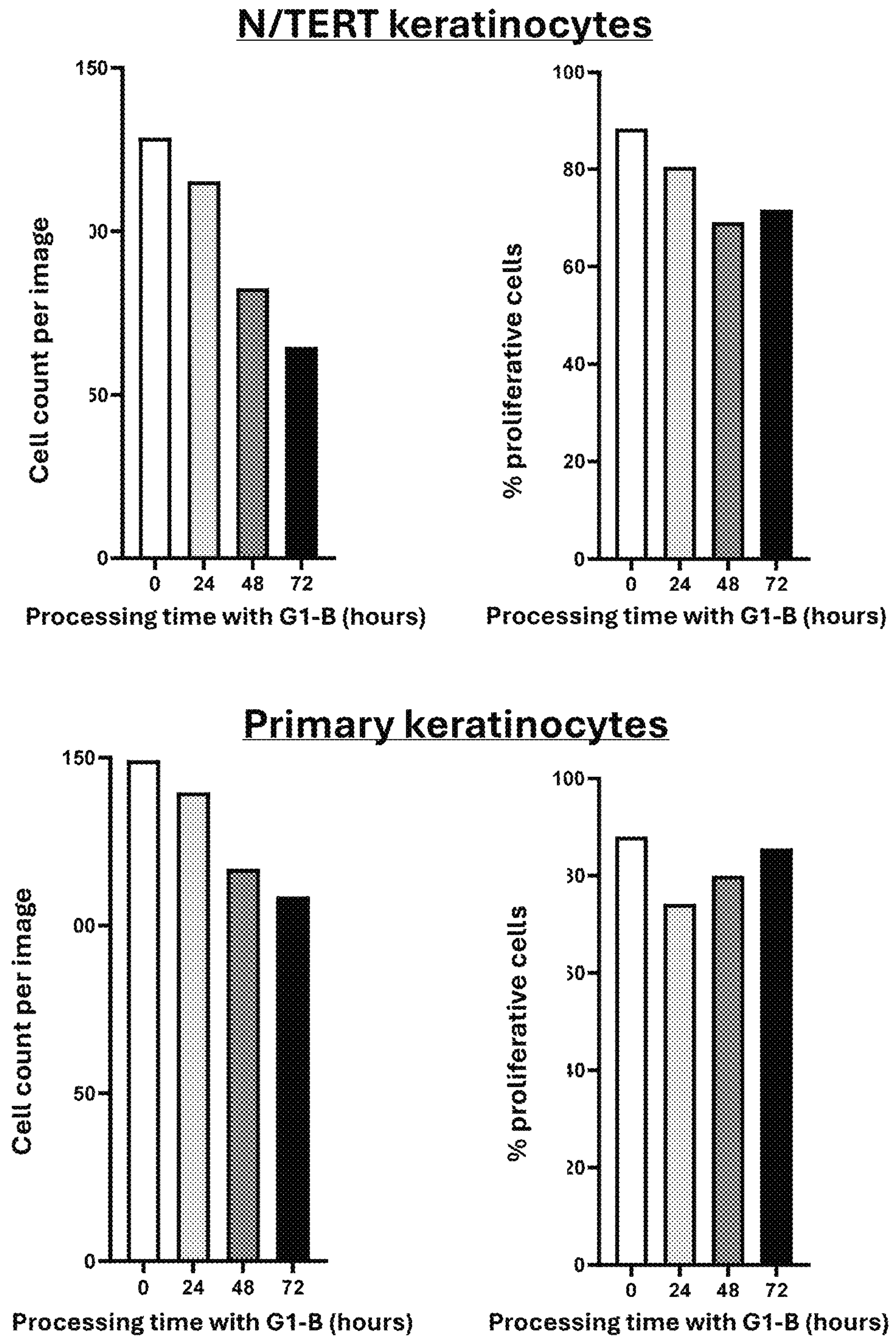
FIG. 24

FIG. 24 shows the antiproliferative effect of compound G1-B, as a function of treatment time, on the N-TERT keratinocyte line (top graphs) and on primary human keratinocytes (bottom graphs). A decrease in the total cell count and the percentage of proliferative cells is observed.

4. TriCat 12/G1-C Formulation 4.1 Characterization of the Vesicles

Figure 25:
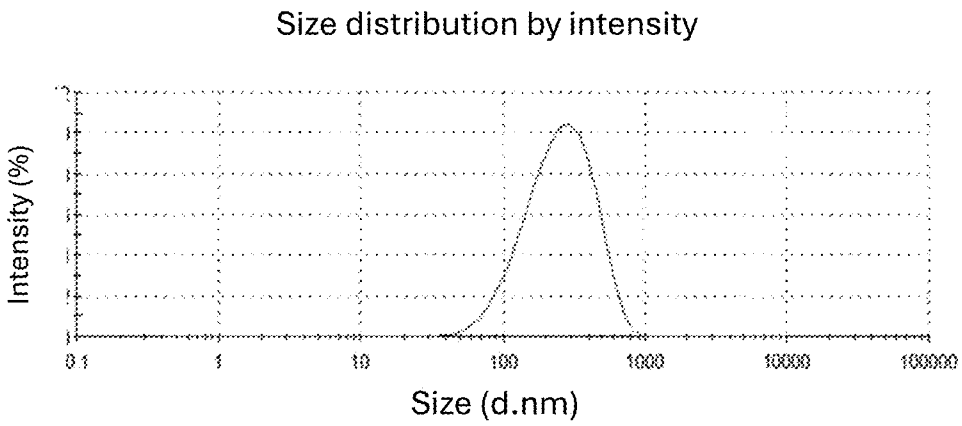
FIG. 25

The formulation of the G1-C dendrimer by TriCat-12 results in the formation of vesicles, with an average diameter around 300 nm [FIG. 25]. The average encapsulation rate is 80% for G1-C dendrimer.

Figure 26:
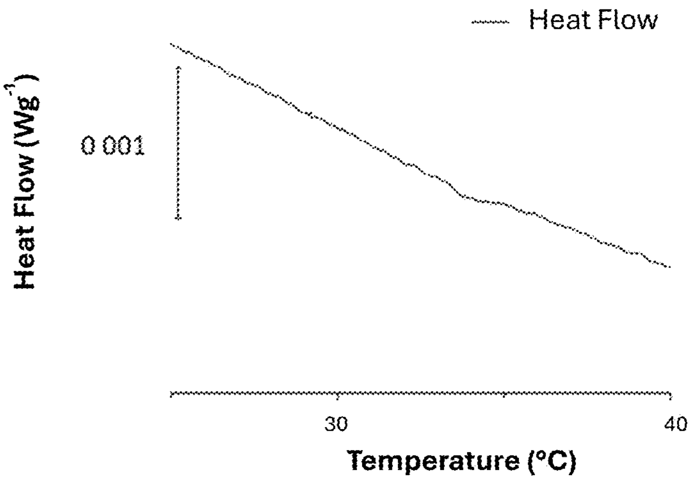
FIG. 26

Below 34° C. the membrane bilayer of the formulations is rigid and very stable. Above 34° C. (skin temperature oscillates between 3° and 35° C.), this membrane becomes fluid and its bio-adressing properties are increased (diffusion into the tissues, fusion with the cells, release of active ingredients) [FIG. 26].

4.2 Stability of the Formulation

Figure 27:
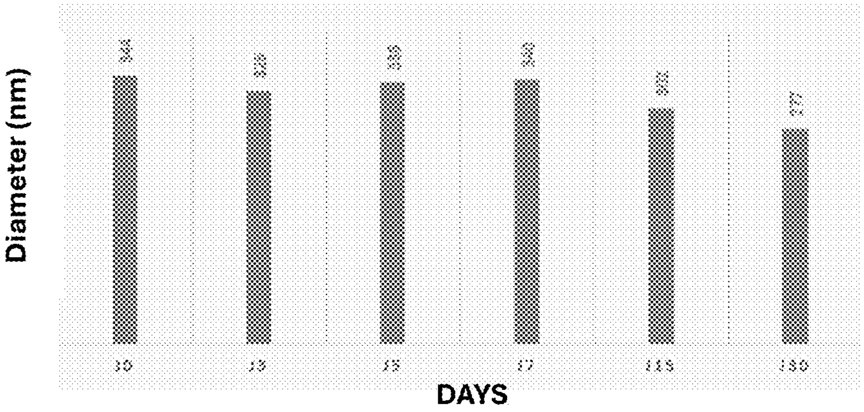
FIG. 27
Figure 28:
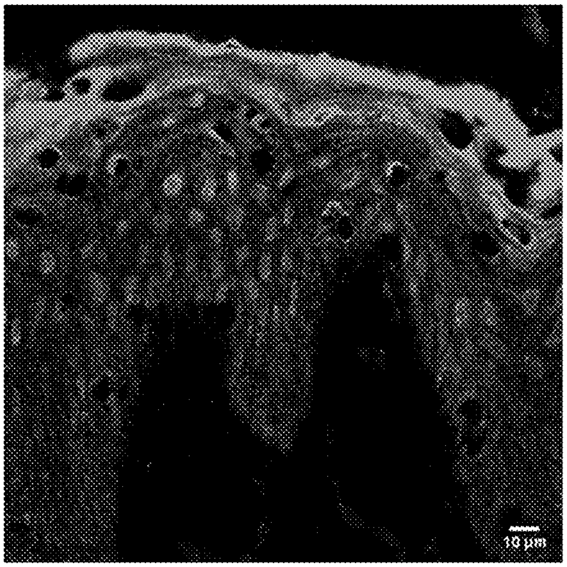
FIG. 28

The formulations are stable (in terms of diameter) for more than a month when stored at 4° C. in solution [FIG. 27], 4.3 Penetration of the Formulation into the Skin Experiments on pig skin were carried out to verify by confocal microscopy whether the dendrimer formulated in the vesicles could penetrate the deep layers of the skin. These pictures show that the dendrimer penetrates deep into the epidermis and dermis when formulated in TriCat12/G1-C vesicles [FIG. 28].

4.4 Monocyte Activation

Figure 29:
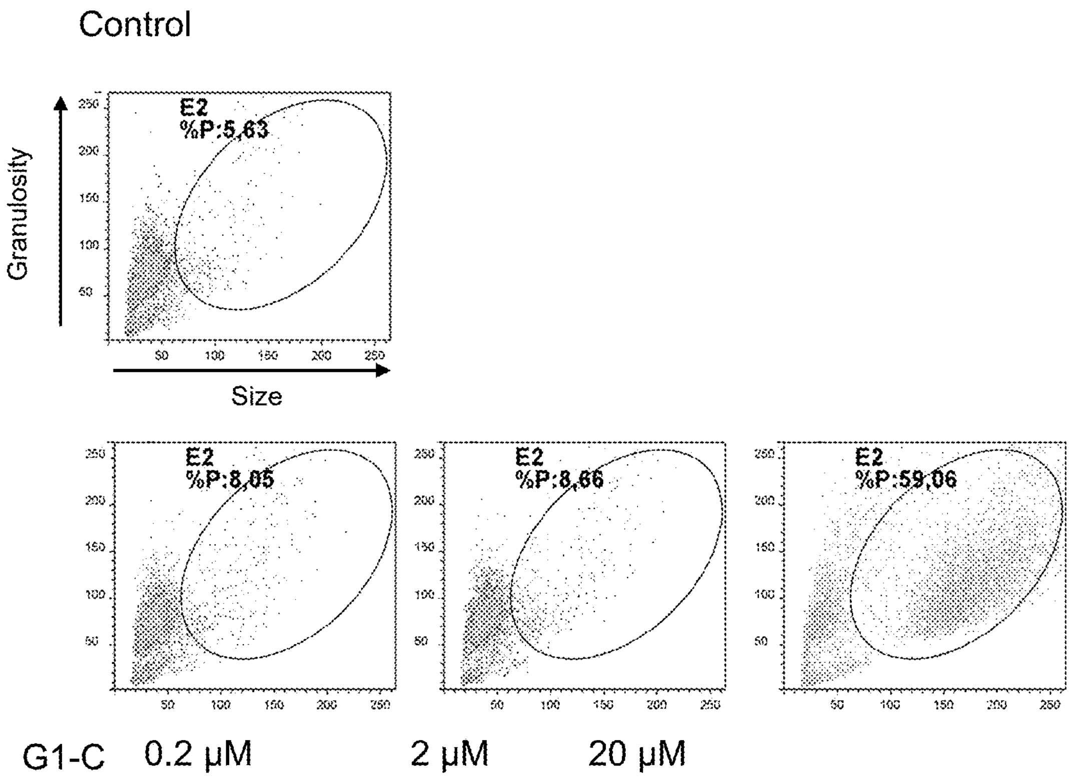
FIG. 29

A change in morphology (increased granularity and size) reflects activation of primary human monocytes. The results show that G1-C dendrimer at 20 μM leads to an increase in granularity and size. Furthermore, we note that almost half of the cells are in the ellipse of activated monocytes [FIG. 29].

5. TriCat 8/G1-B Formulation 5.1 Characterization of the Vesicles

Figure 30:
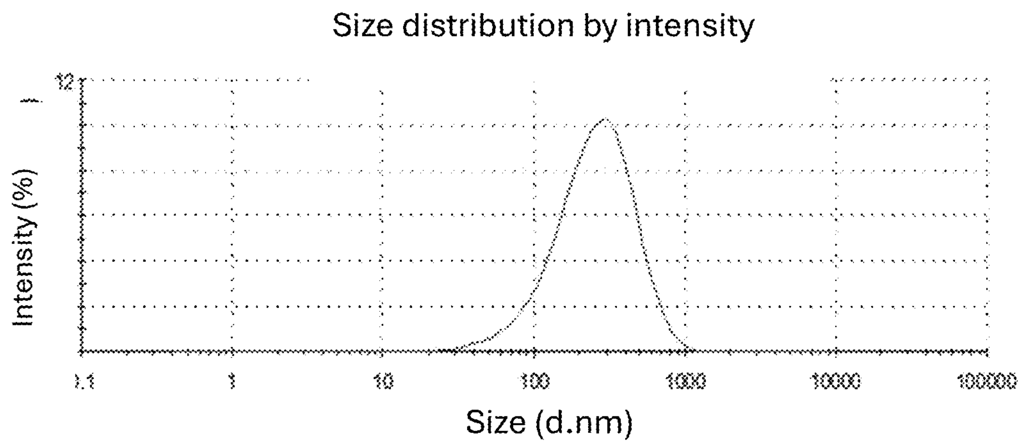
FIG. 30

The formulation of the G1-B dendrimer by TriCat-8 results in the formation of vesicles, with an average diameter around 300 nm [FIG. 30].

6. TriCat 16/G1-B Formulation 6.1 Characterization of the Vesicles

Figure 31:
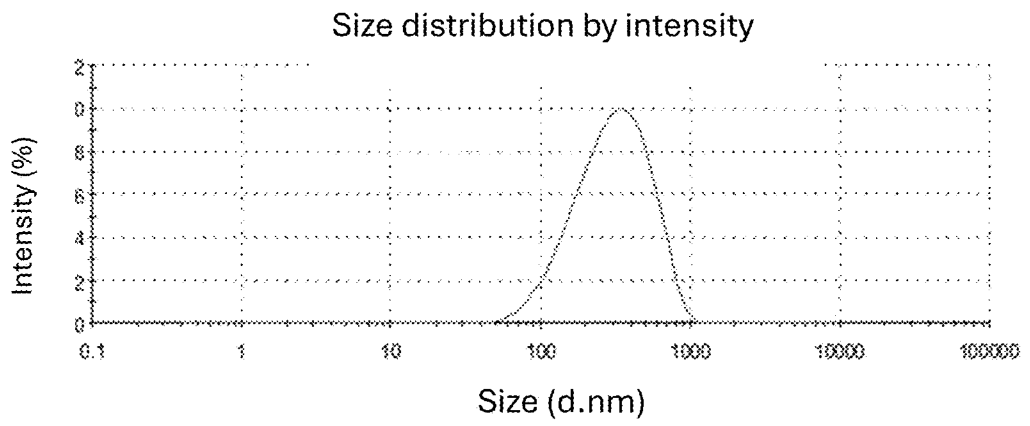
FIG. 31

The formulation of the G1-B dendrimer by TriCat-16 results in the formation of vesicles, with an average diameter around 300-400 nm [FIG. 31].

6.2 Stability of the Formulation

Figure 32:
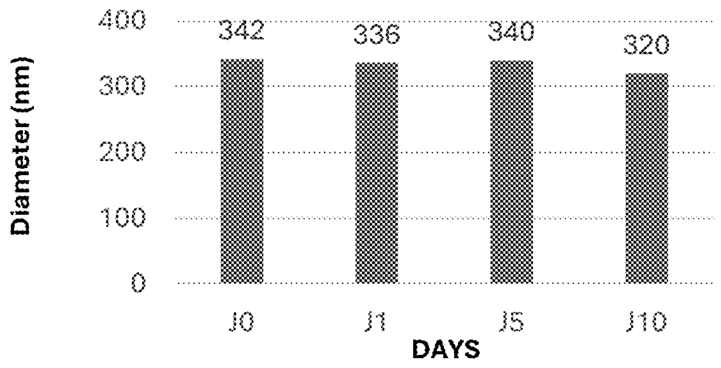
FIG. 32

TriCat-16/G1B formulations are stable (in terms of diameter) for over 10 days when stored at 4° C. in solution [FIG. 32].

The invention claimed is:

1. A vesicle comprising:

a catanionic surfactant of formula (I) or a mixture of catanionic surfactants of general formula (I):

(I)

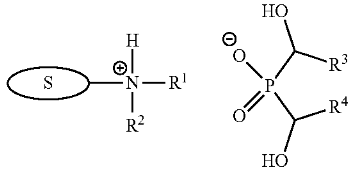

wherein

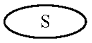

is a sugar, $R^1$ is selected from H and a linear or branched, saturated or unsaturated hydrocarbon chain of 1 to 20 carbon atoms, $R^2$ is a linear or branched, saturated or unsaturated hydrocarbon chain of 1 to 20 carbon atoms, $R^3$ and $R^4$ are independently of each other a linear or branched, saturated or unsaturated hydrocarbon chain, of 1 to 19 carbon atoms; and a dendrimer of formula (II):

(II)

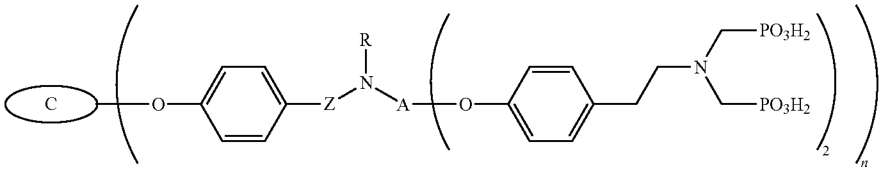

wherein

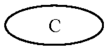

is selected from the pentoses, hexoses and groups of the following formulas:

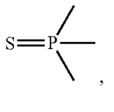 ,

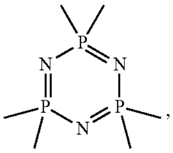 ,

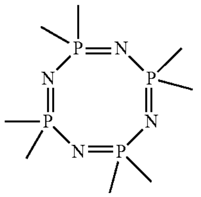

and

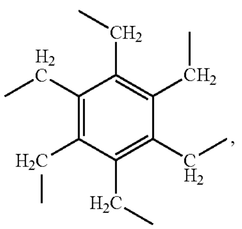 ,

Z is selected from —$CH_2$— and —CH=N—,

R is selected from H and C1-C12-alkyl

A is selected from

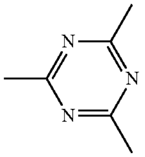

and

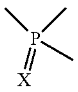

where X is selected from S and O, and n is an integer between 3 and 8.

2. The vesicle according to claim 1, wherein in the sugar-derived catanionic surfactant of formula (I),

is 1-lactitol.

3. The vesicle according to claim 1, wherein in the dendrimer of formula (II),

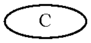

is

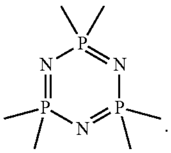

.

4. The vesicle according to claim 1, wherein the molar ratio of catanionic surfactant to dendrimer is between 50/1 and 1/1.

5. The vesicle according to claim 4, wherein the encapsulation rate of the dendrimer of formula (I) in the catanionic surfactant of formula (II) is greater than 50%.

6. The vesicle according to claim 1, wherein the average diameter is between 50 and 500 nm.

7. A pharmaceutical composition comprising at least one vesicle according to claim 1 and a pharmaceutically acceptable excipient.

8. A method of using the vesicle of claim 1 or as pharmaceutical composition comprising the vesicle, comprising providing the vesicle or composition to a subject as a medicament.

9. A method of treating psoriasis in a subject in need thereof comprising providing the vesicle of claim 1 or as pharmaceutical composition comprising the vesicle to a subject for treatment of psoriasis.

10. The method according to claim 9 wherein providing is performed by topical administration.

11. A method for preparing a vesicle according to claim 1 comprising the following steps in succession:

(a) mixing one or more N-alkylaminosugars of formula (I'):

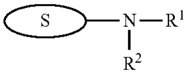

(I')

wherein

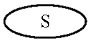

is a sugar, $R^1$ is selected from H and a linear or branched, saturated or unsaturated hyrdrocarbon change of 1 to 20 carbon atoms, $R^2$ is a linear or branched, saturated or unsaturated hydrocarbon chain of 1 to 20 carbon atoms;

and of a phosphinic acid of formula (I''):

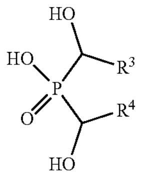

(I'')

wherein $R^3$ and $R^4$ are independently of each other a linear or branched, saturated or carbon atoms A unsaturated, hydrocarbon chain of 1 to 19 carbon atoms and of the dendrimer of formula (II) as defined in claim 1; and (b) optionally, separating the obtained vesicle from the unencapsulated dendrimer.

* * * * *